(12) United States Patent
Bosques et al.

(10) Patent No.: US 11,155,640 B2
(45) Date of Patent: Oct. 26, 2021

(54) COMPOSITIONS AND METHODS RELATED TO ENGINEERED FC CONSTRUCTS

(71) Applicant: Momenta Pharmaceuticals, Inc., Cambridge, MA (US)

(72) Inventors: Carlos J. Bosques, Arlington, MA (US); Jonathan C. Lansing, Reading, MA (US); Daniel Ortiz, Stoneham, MA (US); Laura Rutitzky, Somerville, MA (US); Nathaniel J. Washburn, Littleton, MA (US)

(73) Assignee: Janssen Biotech, Inc., Horsham, PA (US)

( * ) Notice: Subject to any disclaimer, the term of this patent is extended or adjusted under 35 U.S.C. 154(b) by 217 days.

(21) Appl. No.: 16/303,793

(22) PCT Filed: May 23, 2017

(86) PCT No.: PCT/US2017/034084
§ 371 (c)(1),
(2) Date: Nov. 21, 2018

(87) PCT Pub. No.: WO2017/205434
PCT Pub. Date: Nov. 30, 2017

(65) Prior Publication Data
US 2019/0284305 A1 Sep. 19, 2019

Related U.S. Application Data

(60) Provisional application No. 62/443,451, filed on Jan. 6, 2017, provisional application No. 62/340,322, filed on May 23, 2016.

(51) Int. Cl.
| | | |
|---|---|---|
| *C07K 1/00* | (2006.01) | |
| *A61K 39/395* | (2006.01) | |
| *C07K 16/00* | (2006.01) | |
| *C07K 16/46* | (2006.01) | |
| *A61P 37/06* | (2006.01) | |

(52) U.S. Cl.
CPC ............ *C07K 16/46* (2013.01); *A61K 39/395* (2013.01); *A61P 37/06* (2018.01); *C07K 16/00* (2013.01); *C07K 2317/526* (2013.01); *C07K 2317/53* (2013.01); *C07K 2317/60* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,719,107 A | 1/1988 | Carosella et al. | |
| 5,426,641 A | 6/1995 | Afrashteh et al. | |
| 5,731,168 A | 3/1998 | Carter et al. | |
| 6,737,056 B1 * | 5/2004 | Presta | C07K 16/4291 424/133.1 |
| 7,183,076 B2 | 2/2007 | Arathoon et al. | |
| 7,803,769 B2 | 9/2010 | Sullivan et al. | |
| 7,951,917 B1 * | 5/2011 | Arathoon | C07K 16/46 530/387.3 |
| 8,216,805 B2 | 7/2012 | Carter et al. | |
| 8,592,562 B2 | 11/2013 | Kannan et al. | |
| 8,680,237 B2 | 3/2014 | Strome et al. | |
| 9,238,080 B2 | 1/2016 | Nielsen et al. | |
| 10,239,944 B2 | 3/2019 | Bosques et al. | |
| 2003/0078385 A1 | 4/2003 | Arathoon | |
| 2009/0074839 A1 | 3/2009 | Milankovits | |
| 2009/0304696 A1 | 12/2009 | Lawson et al. | |
| 2010/0093979 A1 | 4/2010 | Lazar | |
| 2010/0143353 A1 | 6/2010 | Mosser et al. | |
| 2010/0216663 A1 | 8/2010 | Kolkman et al. | |
| 2010/0239633 A1 | 9/2010 | Strome et al. | |
| 2010/0286374 A1 | 11/2010 | Kannan | |
| 2011/0262477 A1 | 10/2011 | Cheng et al. | |
| 2011/0311535 A1 | 12/2011 | Dranoff et al. | |
| 2012/0149876 A1 | 6/2012 | Von Kreudenstein et al. | |
| 2012/0219551 A1 | 8/2012 | Johnson et al. | |
| 2012/0244578 A1 | 9/2012 | Kannan et al. | |
| 2013/0156765 A1 | 6/2013 | Block et al. | |
| 2013/0177555 A1 | 7/2013 | Wilkinson et al. | |
| 2014/0024111 A1 | 1/2014 | Kannan et al. | |
| 2014/0051834 A1 | 2/2014 | Hoffman et al. | |
| 2014/0066599 A2 | 3/2014 | Blein et al. | |
| 2014/0105913 A1 | 4/2014 | Strome et al. | |
| 2014/0187753 A1 | 7/2014 | Blein et al. | |
| 2014/0294817 A1 | 10/2014 | Mosser et al. | |
| 2014/0335075 A1 | 11/2014 | Strome et al. | |
| 2015/0056185 A1 | 2/2015 | Strome et al. | |
| 2015/0184142 A1 | 7/2015 | Hong et al. | |
| 2015/0218236 A1 | 8/2015 | Pleass | |
| 2016/0229913 A1 | 8/2016 | Bosques et al. | |

(Continued)

FOREIGN PATENT DOCUMENTS

| | | |
|---|---|---|
| BR | PI0620639-5 | 11/2011 |
| CN | 101835802 | 9/2010 |

(Continued)

OTHER PUBLICATIONS

Dick Jr. Biotechnology and Bioengineering 2008, 100(6):1132-1143. (Year: 2008).*
Anthony, "Identification of a receptor required for the anti-inflammatory activity of IVIG," Proc. Natl. Acad. Sci. U.S.A., Dec. 16, 2008, 105(50):19571-19578.
Atwell et al., "Stable heterodimers from remodeling the domain interface of a homodimer using a phage display library," Biol., Jul. 4, 1997, 270(1):26-35.
Boruchov AM et al., "Activating and inhibitory IgG Fc receptors on human DCs mediate opposing functions," J Clin Invest., Oct. 2005 115(10):2914-2923.

(Continued)

*Primary Examiner* — Chun W Dahle
(74) *Attorney, Agent, or Firm* — Fish & Richardson P.C.

(57) ABSTRACT

The present invention relates to engineered IgG Fc constructs and uses thereof.

2 Claims, 27 Drawing Sheets
Specification includes a Sequence Listing.

(56) References Cited

U.S. PATENT DOCUMENTS

| | | | |
|---|---|---|---|
| 2019/0225688 A1 | 7/2019 | Bosques et al. | |
| 2019/0345206 A1 | 11/2019 | Bosques et al. | |

FOREIGN PATENT DOCUMENTS

| | | |
|---|---|---|
| JP | 2007-289200 | 11/2007 |
| JP | 2010-529043 | 8/2010 |
| JP | 2011-508604 | 3/2011 |
| JP | 2014-510084 | 4/2014 |
| JP | 2015-527366 | 9/2015 |
| JP | 2015-536317 | 12/2015 |
| WO | WO 1997/047732 | 12/1997 |
| WO | WO 01/45746 | 6/2001 |
| WO | WO 2005/077981 | 8/2005 |
| WO | WO 2006/106905 | 10/2006 |
| WO | WO 2008/012543 | 1/2008 |
| WO | WO 2008/131242 | 10/2008 |
| WO | WO 2008/143954 | 11/2008 |
| WO | WO 2008/151088 | 12/2008 |
| WO | WO 2009/089004 | 7/2009 |
| WO | WO 2010/085682 | 7/2010 |
| WO | WO 2010/135521 | 11/2010 |
| WO | WO 2010/135534 | 11/2010 |
| WO | WO 2011/034605 | 3/2011 |
| WO | WO-2011/073692 | 6/2011 |
| WO | WO-2012/006635 | 1/2012 |
| WO | WO 2012/123949 | 9/2012 |
| WO | WO 2014/031646 | 2/2014 |
| WO | WO 2014/060712 | 4/2014 |
| WO | WO 2015/054958 | 4/2015 |
| WO | WO 2015/095684 | 6/2015 |
| WO | WO 2015/107025 | 7/2015 |
| WO | WO 2015/107026 | 7/2015 |
| WO | WO 2015/132364 | 9/2015 |
| WO | WO 2015/132365 | 9/2015 |
| WO | WO 2015/168643 | 11/2015 |
| WO | WO 2015/184207 | 12/2015 |
| WO | WO 2017/151971 | 9/2017 |
| WO | WO 2017/205434 | 11/2017 |

OTHER PUBLICATIONS

Chu et al., "Inhibition of B cell receptor-mediated activation of primary human B cells by coengagement of CD19 and FcgammaRIIb with Fc-engineered antibodies," Mol Immunol., Sep. 2008, 45(15):3926-3933.

Dall'Acqua et al., "Modulation of the Effector Functions of a Human IgG 1 through Engineering of Its Hinge Region," J. lmmunol, 2006, 177:1129-1138.

Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel., Apr. 2010, 2(4)3:195-202.

European Search Report in Application No. 15785583.4, dated Nov. 7, 2017, 12 pages.

European Search Report in Application No. 17760849.4, dated Sep. 24, 2019, 12 pages.

European Search Report in Application No. 17803465.8, dated Feb. 17, 2020, 12 pages.

Gunadekaran et al., "Enhancing antibody Fc heterodimer formation through electrostatic steering effects: applications to bispecific molecules and monovalent IgG.," J Biol Chem, Jun. 18, 2010, 285(25):19637-19646.

International Preliminary Report on Patentability in International Patent Application No. PCT/US2017/020519, dated Sep. 4 2018 (2 pages).

International Preliminary Report on Patentability in International Patent Application No. PCT/US2015/028926, dated Nov. 17, 2016, 12 pages.

International Preliminary Report on Patentability in International Patent Application No. PCT/US2017/034087, dated Nov. 27, 2018, 11 pages.

International Preliminary Report on Patentability in International Patent Application No. PCT/US2017/034084, dated Nov. 27, 2018, 10 pages.

International Search Report and Written Opinion in International Application No. PCT/US17/20519, dated Aug. 24, 2017, 17 pages.

International Search Report and Written Opinion in International Application No. PCT/US17/34084, dated Sep. 14, 2017, 19 pages.

International Search Report and Written Opinion in International Application No. PCT/US17/34087, dated Oct. 18, 2017, 20 pages.

International Search Report and Written Opinion in International Application No. PCT/US2015/028926, dated Oct. 28, 2015, 22 pages.

International Search Report and Written Opinion in International Application No. PCT/US2018/012488, dated May 25, 2018, 26 pages.

International Preliminary Report on Patentability in International Application No. PCT/US2018/012488, dated Jul. 9, 2019, 10 pages.

Kacskovics et al., "Fc receptors in livestock species," Veterinary Immunology and Immunopathology, 2004, 102:351-362.

Lund et al., "Multiple Interactions of Ig with Its Core Oligosac-chadde Can Modulate Recognition by Cornplernent and Human Fcy Receptor I and Influence the Synthesis of Its Oligosaccharide Chains," The Journal of Immunology, 1996, 157:4963-4969.

Martens et al., "A novel one-armed anti-c-Met antibody inhibits glioblastoma growth in vivo," Clin Cancer Res., 2006, 12(20):6144-6152.

Mekhaiel et al., "Polymeric human Fc-fusion proteins with modified effector functions," Scientific Reports, Aug. 2011, 1: 124 (11 pages).

Merchant et al., "An efficient route to human bispecific IgG,"*Nat Biotechnol*, Jul. 1998, 16(7):677-681.

Mimoto et al., "Novel asymmetrically engineered antibody Fc variant with superior FcyR binding affinity and specificity compared with afucosylated Fc variant," mAbs, Feb. 2013, 5:229-236.

Office Action in Israeli Application No. 247442, dated Jun. 3, 2018, 7 pages.

Ortiz et al., "Elucidating the interplay between IgG-Fc valency and FcgR acticaton for the design of immune complex inhibitors," Science Translational Medicine, Nov. 16, 2016, 8(365):1-13.

Ridgway et al., "'Knobs-into-holes' engineering of antibody CH3 domains for heavy chain heterodimerization," *Protein Eng.*, Jul. 1996, 9(7):617-612.

Salfeld, "Isotype selection in antibody engineering," Nature Biotech, 2007, 25(12): 1369-1372.

Shields et al., "High Resolution Mapping of the Binding Site on Human IgG1 for FcyRI, FcyRII, FcyRIII, and FcRn and Design of IgG1 Variants with Improved Binding to the FcyR," J. Biol. Chem., 2001, 276(9):6591-6604.

Stavenhagen et al., "Fc Optimization of Therapeutic Antibodies Enhances Their Ability to Kill Tumor Cells In vitro and Controls Tumor Expansion In vivo via Low-Affinity Activating Fcy Receptors," Cancer Res, 2007, 67: 8882-8890.

Wilson et al., "The structure of an antigenic determinant in a protein," Cell, Jul. 1984, 37(3):767-778.

Zeidler et al., "Simultaneous activation of T cells and accessory cells by a new class of intact bispecific antibody results in efficient tumor cell killing," J Immunol., Aug. 1999, 163(3):1246-1252.

Carter "Bispecific human IgG by design," J of Immunol Methods., Feb. 1, 2001, 248(1-2):7-15.

Crick et al., "A tracer study of the metabolism of p-iodophenyl urethane; the selective localization of radioactive material," Br J Pharmacol Chemother., Mar. 1952, 7(1):142-151.

European Search Report in Application No. 17803463.3, dated Jul. 15, 2020, 11 pages.

European Office Action in Application No. 15785583.4, dated Oct. 12, 2020, 4 pages.

Mestas et al., "Of Mice and Not Men: Differences between Mouse and Human Immunology," J Immunology., 2004, 172(5):2731-2738.

(56) References Cited

OTHER PUBLICATIONS

Sowdhamini et al., "Stereochemical modeling of disulfide bridges. Criteria for introduction into proteins by site-directed mutagenesis," Protein Eng., Nov. 1989, 3(2):95-103.
Chamow et al., "A humanized, bispecific immunoadhesin-antibody that retargets CD3+ effectors to kill HIV-1-infected cells," J. Immunol., 1994, 153:4268-4280 (Abstract Only).
European Search Report in Application No. 18736414.6, dated Nov. 16, 2020, 16 pages.
European Search Report in Application No. 17760849.4, dated Jan. 11, 2021, 4 pages.
European Office Action in Application No. 17803465.8, dated Jan. 20, 2021, 8 pages.
Grevys et al., "Open Access Fc Engineering of Human IgG1 for Altered Binding to the Neonatal Fc Receptor Affects Fc Effector Functions," The Journal of Immunology, 194(11):5497-5508.
Kinder et al., "Engineered protease-resistant antibodies with selectable cell-killing functions," J of Biol Chem., Oct. 25, 2013, 288(43):30843-30854.

\* cited by examiner (Fc constructs 1, 2, and 3)

(Fc construct 4)

SEQUENCE LISTING

```
<160> NUMBER OF SEQ ID NOS: 62

<210> SEQ ID NO 1
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 1

Gly Gly Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 2

Gly Gly Ser Gly
1

<210> SEQ ID NO 3
<211> LENGTH: 4
```

```
<212> TYPE: PRT
<213> ORGANISM: Artificial Sequence
<220> FEATURE:
<223> OTHER INFORMATION: synthetic polypeptide

<400> SEQUENCE: 3

Ser Gly Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 4

Gly Ser Gly Ser
1

<210> SEQ ID NO 5
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 5

Gly Ser Gly Ser Gly Ser
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 6

Gly Ser Gly Ser Gly Ser Gly Ser
1               5

<210> SEQ ID NO 7
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 7

Gly Ser Gly Ser Gly Ser Gly Ser Gly Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 8

Gly Ser Gly Ser Gly Ser Gly Ser Gly Ser Gly Ser
1               5                   10

<210> SEQ ID NO 9
<211> LENGTH: 6
<212> TYPE: PRT
```

```
<213> ORGANISM: Artificial Sequence
<220> FEATURE:
<223> OTHER INFORMATION: synthetic polypeptide

<400> SEQUENCE: 9

Gly Gly Ser Gly Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 10

Gly Gly Ser Gly Gly Ser Gly Gly Ser
1               5

<210> SEQ ID NO 11
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 11

Gly Gly Ser Gly Gly Ser Gly Gly Ser Gly Gly Ser
1               5                   10

<210> SEQ ID NO 12
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 12

Gly Gly Ser Gly Gly Gly Ser Gly
1               5

<210> SEQ ID NO 13
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 13

Gly Gly Ser Gly Gly Gly Ser Gly Gly Gly Ser Gly
1               5                   10

<210> SEQ ID NO 14
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 14

Gly Gly Ser Gly Gly Gly Ser Gly Gly Gly Ser Gly Gly Gly Ser Gly
1               5                   10                  15

<210> SEQ ID NO 15
<211> LENGTH: 20
<212> TYPE: PRT
<213> ORGANISM: Artificial Sequence
```

```
<220> FEATURE:
<223> OTHER INFORMATION: synthetic polypeptide

<400> SEQUENCE: 15

Gly Gly Ser Gly Gly Ser Gly Gly Ser Gly Gly Ser Gly
 1               5                  10                  15

Gly Gly Ser Gly
            20

<210> SEQ ID NO 16
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 16

Gly Gly Gly Gly Ser Gly Gly Gly Gly Ser
 1               5                  10

<210> SEQ ID NO 17
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 17

Gly Gly Gly Gly Ser Gly Gly Gly Ser Gly Gly Gly Gly Ser
 1               5                  10                  15

<210> SEQ ID NO 18
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 18

Ser Gly Gly Gly Ser Gly Gly Gly Ser Gly Gly Ser Gly Gly Gly
 1               5                  10                  15

Ser Gly Gly Gly
            20

<210> SEQ ID NO 19
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 19

Gly Gly Gly Gly
 1

<210> SEQ ID NO 20
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 20

Gly Gly Gly Gly Gly Gly Gly Gly
 1               5
```

<210> SEQ ID NO 21
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 21

Gly Gly Gly Gly Gly Gly Gly Gly Gly Gly Gly Gly
1               5                   10

<210> SEQ ID NO 22
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 22

Gly Gly Gly Gly Gly Gly Gly Gly Gly Gly Gly Gly Gly Gly Gly Gly
1               5                   10                  15

<210> SEQ ID NO 23
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 23

Gly Gly Gly Gly Gly Gly Gly Gly Gly Gly Gly Gly Gly Gly Gly Gly
1               5                   10                  15

Gly Gly Gly Gly
            20

<210> SEQ ID NO 24
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 24

Gly Gly Gly Gly Gly
1               5

<210> SEQ ID NO 25
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 25

Gly Gly Gly Gly Gly Gly Gly Gly Gly Gly
1               5                   10

<210> SEQ ID NO 26
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 26

Gly Gly Gly Gly Gly Gly Gly Gly Gly Gly Gly Gly Gly Gly Gly

```
<210> SEQ ID NO 27
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 27

Gly Gly Gly Gly Gly Gly Gly Gly Gly Gly Gly Gly Gly Gly Gly Gly
1               5                   10                  15
Gly Gly Gly Gly
            20

<210> SEQ ID NO 28
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 28

Gly Glu Asn Leu Tyr Phe Gln Ser Gly Gly
1               5                   10

<210> SEQ ID NO 29
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 29

Ser Ala Cys Tyr Cys Glu Leu Ser
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 30

Arg Ser Ile Ala Thr
1               5

<210> SEQ ID NO 31
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 31

Arg Pro Ala Cys Lys Ile Pro Asn Asp Leu Lys Gln Lys Val Met Asn
1               5                   10                  15
His

<210> SEQ ID NO 32
<211> LENGTH: 36
<212> TYPE: PRT
<213> ORGANISM: Artificial Sequence
<220> FEATURE:
<223> OTHER INFORMATION: synthetic polypeptide
```

<400> SEQUENCE: 32

Gly Gly Ser Ala Gly Gly Ser Gly Ser Gly Ser Gly Gly Ser Ser
1               5                   10                  15
Gly Ala Ser Gly Thr Gly Thr Ala Gly Gly Thr Gly Ser Gly Ser Gly
            20                  25                  30
Thr Gly Ser Gly
        35

<210> SEQ ID NO 33
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 33

Ala Ala Ala Asn Ser Ser Ile Asp Leu Ile Ser Val Pro Val Asp Ser
1               5                   10                  15
Arg

<210> SEQ ID NO 34
<211> LENGTH: 36
<212> TYPE: PRT
<213> ORGANISM: Artificial Sequence
<220> FEATURE:
<223> OTHER INFORMATION: synthetic polypeptide

<400> SEQUENCE: 34

Gly Gly Ser Gly Gly Gly Ser Glu Gly Gly Ser Glu Gly Gly Gly
1               5                   10                  15
Ser Glu Gly Gly Gly Ser Glu Gly Gly Gly Ser Glu Gly Gly Gly Ser
            20                  25                  30
Gly Gly Gly Ser
        35

<210> SEQ ID NO 35
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 35

Gly Gly Gly Ser Gly Gly Gly Ser Gly Gly Gly Ser
1               5                   10

<210> SEQ ID NO 36
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 36

Gly Gly Ser Gly Gly Gly Ser Gly Gly Gly Ser Gly Gly Gly Ser Gly
1               5                   10                  15
Gly Ser

<210> SEQ ID NO 37
<211> LENGTH: 11
<212> TYPE: PRT
<213> ORGANISM: Artificial Sequence

```
<220> FEATURE:
<223> OTHER INFORMATION: synthetic polypeptide

<400> SEQUENCE: 37

Asp Ile Cys Leu Pro Arg Trp Gly Cys Leu Trp
1               5                   10

<210> SEQ ID NO 38
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 38

His His His His His His
1               5

<210> SEQ ID NO 39
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 39

Asp Tyr Lys Asp Asp Asp Asp Lys
1               5

<210> SEQ ID NO 40
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 40

Glu Gln Lys Leu Ile Ser Glu Glu Asp Leu
1               5                   10

<210> SEQ ID NO 41
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 41

Tyr Pro Tyr Asp Val Pro Asp Tyr Ala
1               5

<210> SEQ ID NO 42
<211> LENGTH: 227
<212> TYPE: PRT
<213> ORGANISM: Homo sapiens

<400> SEQUENCE: 42

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 43
<211> LENGTH: 474
<212> TYPE: PRT
<213> ORGANISM: Artificial Sequence
<220> FEATURE:
<223> OTHER INFORMATION: synthetic polypeptide

<400> SEQUENCE: 43

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys Ser Gly Gly Gly Ser Gly Gly Gly Ser Gly Gly Gly Ser
225                 230                 235                 240

Gly Gly Gly Ser Gly Gly Asp Lys Thr His Thr Cys Pro Pro Cys Pro
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 44
<211> LENGTH: 227
<212> TYPE: PRT
<213> ORGANISM: Artificial Sequence
<220> FEATURE:
<223> OTHER INFORMATION: synthetic polypeptide

<400> SEQUENCE: 44

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 45
<211> LENGTH: 473
<212> TYPE: PRT
<213> ORGANISM: Artificial Sequence
<220> FEATURE:
<223> OTHER INFORMATION: synthetic polypeptide

<400> SEQUENCE: 45

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Ser Gly Gly Ser Gly Gly Ser Gly Gly Gly Ser
225                 230                 235                 240

Gly Gly Gly Ser Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
            370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
            435                 440                 445

Val Phe Ser Cys Ser Val Met His Glu Ala Leu His Asn His Tyr Thr
450                 455                 460

Gln Lys Ser Leu Ser Leu Ser Pro Gly
465                 470

<210> SEQ ID NO 46
<211> LENGTH: 226
<212> TYPE: PRT
<213> ORGANISM: Artificial Sequence
<220> FEATURE:
<223> OTHER INFORMATION: synthetic polypeptide

<400> SEQUENCE: 46

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 47
<211> LENGTH: 468
<212> TYPE: PRT
<213> ORGANISM: Artificial Sequence
<220> FEATURE:
<223> OTHER INFORMATION: synthetic polypeptide

<400> SEQUENCE: 47

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys Gly Gly Gly Gly Gly Gly Gly Gly Gly
225                 230                 235                 240

Gly Gly Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Lys Ser Asp Gly Ser Phe Phe Leu Tyr Ser Asp Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 48
<211> LENGTH: 226
<212> TYPE: PRT
<213> ORGANISM: Artificial Sequence
<220> FEATURE:
<223> OTHER INFORMATION: synthetic polypeptide

<400> SEQUENCE: 48

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
        130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly
225

<210> SEQ ID NO 49
<211> LENGTH: 473
<212> TYPE: PRT
<213> ORGANISM: Artificial Sequence
<220> FEATURE:
<223> OTHER INFORMATION: synthetic polypeptide

<400> SEQUENCE: 49

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys Gly Gly Gly Gly Gly Gly Gly Gly Gly Gly Gly Gly Gly
225                 230                 235                 240

```
Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
        260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470

<210> SEQ ID NO 50
<211> LENGTH: 227
<212> TYPE: PRT
<213> ORGANISM: Artificial Sequence
<220> FEATURE:
<223> OTHER INFORMATION: synthetic polypeptide

<400> SEQUENCE: 50

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 51
<211> LENGTH: 227
<212> TYPE: PRT
<213> ORGANISM: Artificial Sequence
<220> FEATURE:
<223> OTHER INFORMATION: synthetic polypeptide

<400> SEQUENCE: 51

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 52
```

-continued

```
<211> LENGTH: 226
<212> TYPE: PRT
<213> ORGANISM: Artificial Sequence
<220> FEATURE:
<223> OTHER INFORMATION: synthetic polypeptide

<400> SEQUENCE: 52

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 53
<211> LENGTH: 227
<212> TYPE: PRT
<213> ORGANISM: Artificial Sequence
<220> FEATURE:
<223> OTHER INFORMATION: synthetic polypeptide

<400> SEQUENCE: 53

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

```
                     85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
Tyr Thr Leu Pro Pro Cys Arg Asp Lys Leu Thr Lys Asn Gln Val Ser
        130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
            210                 215                 220
Pro Gly Lys
225

<210> SEQ ID NO 54
<211> LENGTH: 474
<212> TYPE: PRT
<213> ORGANISM: Artificial Sequence
<220> FEATURE:
<223> OTHER INFORMATION: synthetic polypeptide

<400> SEQUENCE: 54

Gln Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
Tyr Thr Leu Pro Pro Cys Arg Asp Glu Leu Thr Lys Asn Gln Val Ser
        130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
```

```
                210                 215                 220
Pro Gly Lys Ser Gly Gly Ser Gly Gly Ser Gly Gly Ser
225                 230                 235                 240

Gly Gly Gly Ser Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
                290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Asp Glu
                370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
                420                 425                 430

Leu Tyr Ser Asp Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460

Gln Lys Ser Leu Ser Leu Ser Pro Gly Lys
465                 470

<210> SEQ ID NO 55
<211> LENGTH: 227
<212> TYPE: PRT
<213> ORGANISM: Artificial Sequence
<220> FEATURE:
<223> OTHER INFORMATION: synthetic polypeptide

<400> SEQUENCE: 55

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
```

```
                    100                 105                 110
Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 56
<211> LENGTH: 473
<212> TYPE: PRT
<213> ORGANISM: Artificial Sequence
<220> FEATURE:
<223> OTHER INFORMATION: synthetic polypeptide

<400> SEQUENCE: 56

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Ser Gly Gly Gly Ser Gly Gly Gly Ser Gly Gly Gly Ser
```

-continued

```
            225                 230                 235                 240
    Gly Gly Gly Ser Gly Gly Asp Lys Thr His Thr Cys Pro Pro Cys
                    245                 250                 255

Pro Ala Pro Glu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
                290                 295                 300

Tyr Val Asp Gly Val Glu Val His Asn Ala Lys Thr Lys Pro Arg Glu
    305                 310                 315                 320

Glu Gln Tyr Asn Ser Thr Tyr Arg Val Val Ser Val Leu Thr Val Leu
                    325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Asp Glu
        370                 375                 380

Leu Thr Lys Asn Gln Val Ser Leu Thr Cys Leu Val Lys Gly Phe Tyr
    385                 390                 395                 400

Pro Ser Asp Ile Ala Val Glu Trp Glu Ser Asn Gly Gln Pro Glu Asn
                    405                 410                 415

Asn Tyr Lys Thr Thr Pro Pro Val Leu Lys Ser Asp Gly Ser Phe Phe
                420                 425                 430

Leu Tyr Ser Asp Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460

Gln Lys Ser Leu Ser Leu Ser Pro Gly
    465                 470

<210> SEQ ID NO 57
<211> LENGTH: 226
<212> TYPE: PRT
<213> ORGANISM: Artificial Sequence
<220> FEATURE:
<223> OTHER INFORMATION: synthetic polypeptide

<400> SEQUENCE: 57

Gln Lys Thr His Thr Cys Pro Pro Cys Pro Ala Pro Glu Leu Leu Gly
    1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
    65                  70                  75                  80

Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
```

```
            115                 120                 125
Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 58
<211> LENGTH: 468
<212> TYPE: PRT
<213> ORGANISM: Artificial Sequence
<220> FEATURE:
<223> OTHER INFORMATION: synthetic polypeptide

<400> SEQUENCE: 58

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Asp Lys Thr His Thr Cys Pro Pro Cys Pro Ala Pro Glu Leu
```

```
                    245                 250                 255
Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Lys Ser Asp Gly Ser Phe Phe Leu Tyr Ser Asp Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 59
<211> LENGTH: 226
<212> TYPE: PRT
<213> ORGANISM: Artificial Sequence
<220> FEATURE:
<223> OTHER INFORMATION: synthetic polypeptide

<400> SEQUENCE: 59

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
```

```
       130                 135                 140
Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 60
<211> LENGTH: 473
<212> TYPE: PRT
<213> ORGANISM: Artificial Sequence
<220> FEATURE:
<223> OTHER INFORMATION: synthetic polypeptide

<400> SEQUENCE: 60

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
```

```
                260                 265                 270
Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470

<210> SEQ ID NO 61
<211> LENGTH: 473
<212> TYPE: PRT
<213> ORGANISM: Artificial Sequence
<220> FEATURE:
<223> OTHER INFORMATION: synthetic polypeptide

<400> SEQUENCE: 61

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
```

```
            145                 150                 155                 160
Trp Glu Ser Asn Gly Gln Pro Glu Asn Tyr Lys Thr Thr Pro Pro
                165                 170                 175

Val Leu Lys Ser Asp Gly Ser Phe Phe Leu Tyr Ser Asp Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys Gly Gly Gly Gly Gly Gly Gly Gly Gly Gly Gly Gly
225                 230                 235                 240

Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
                290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Cys Arg Asp Lys
                370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460

Gln Lys Ser Leu Ser Leu Ser Pro Gly
465                 470

<210> SEQ ID NO 62
<211> LENGTH: 473
<212> TYPE: PRT
<213> ORGANISM: Artificial Sequence
<220> FEATURE:
<223> OTHER INFORMATION: synthetic polypeptide

<400> SEQUENCE: 62

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
```

-continued

```
                35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Lys Ser Asp Gly Ser Phe Phe Leu Tyr Ser Asp Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Gly Gly Gly Gly Gly Gly Gly Gly Gly Gly Gly
225                 230                 235                 240
Gly Gly Gly Gly Gly Gly Asp Lys Thr His Thr Cys Pro Pro Cys Pro
                245                 250                 255
Pro Ala Pro Glu Leu Leu Gly Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser His Glu Asp Pro Glu Val Lys Phe Asn Trp
    290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
        355                 360                 365
Gln Pro Arg Glu Pro Gln Val Tyr Thr Leu Pro Pro Cys Arg Asp Lys
    370                 375                 380
Leu Thr Lys Asn Gln Val Ser Leu Trp Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
        435                 440                 445
Val Phe Ser Cys Ser Val Met His Glu Ala Leu His Asn His Tyr Thr
    450                 455                 460
```

```
Gln Lys Ser Leu Ser Leu Ser Pro Gly
465                 470
```

COMPOSITIONS AND METHODS RELATED TO ENGINEERED FC CONSTRUCTS

CROSS-REFERENCE TO RELATED APPLICATIONS

This application is a national phase application under 35 U.S.C. § 371 of PCT Application No. PCT/US2017/034084, filed May 23, 2017, which claims the benefit of prior U.S. Provisional Application Ser. No. 62/340,322, filed May 23, 2016, and or prior U.S. Provisional Application Ser. No. 62/443,451, filed Jan. 6, 2017. The disclosures of the above applications are hereby incorporated by reference in their entirety.

BACKGROUND

Therapeutic proteins, e.g., therapeutic antibodies and Fc-fusion proteins, have rapidly become a clinically important drug class for patients with immunological and inflammatory diseases, cancers, and infections.

SUMMARY OF THE INVENTION

The present disclosure features biologically active Fc domain-containing therapeutic constructs. Such constructs may have desirable serum half-life and/or binding affinity and/or avidity for Fc receptors.

In general, the disclosure features Fc constructs having 2-10 Fc domains, e.g., Fc constructs having 2, 3, 4, 5, 6, 7, 8, 9, or 10 Fc domains. In some embodiments, the Fc construct includes 2-10 Fc domains, 2-5 Fc domains, 2-4 Fc domains, 2-3 Fc domains, 3-5 Fc domains, 2-8 Fc domains, or 2-6 Fc domains. In some embodiments, the Fc construct includes 2-4 Fc domains. In some embodiments, the Fc construct includes 5-10 Fc domains (e.g., 5-6, 5-7, 5-8, 5-9, or 5-10 Fc domains).

In some embodiments, constructs (e.g., Fc constructs having 2-4 Fc domains, e.g., 2, 3, or 4 Fc domains) and homogenous pharmaceutical compositions (e.g., those containing Fc constructs having 2-4 Fc domains, e.g., 2, 3, or 4 Fc domains) of the disclosure are useful, e.g., to reduce inflammation in a subject, to promote clearance of autoantibodies in a subject, to suppress antigen presentation in a subject, to block an immune response, e.g., block an immune complex-based activation of the immune response in a subject, and to treat immunological and inflammatory diseases (e.g., autoimmune diseases) in a subject. The Fc constructs described herein can be used to treat patients having immunological and inflammatory diseases without significant stimulation of immune cells. In some embodiments, constructs (e.g., Fc constructs having 5-10 Fc domains, e.g., 5, 6, 7, 8, 9, or 10 Fc domains) and homogenous pharmaceutical compositions (e.g., those containing Fc constructs having 5-10 Fc domains, e.g., 5, 6, 7, 8, 9, or 10 Fc domains) of the disclosure are useful, e.g., to induce immune cell activation of the immune response in a subject, to increase phagocytosis of a target cell (i.e., a cancer cell or an infected cell) in a subject, and to treat diseases such as cancers and infections in a subject.

The properties of these constructs allow for the efficient generation of substantially homogenous compositions. The degree of homogeneity of a composition influences the pharmacokinetics and in vivo performance of the composition. Such homogeneity in a composition is desirable in order to ensure the safety, efficacy, uniformity, and reliability of the composition. An Fc construct of the disclosure can be in a population or composition that is substantially homogenous (e.g., at least 85%, 90%, 95%, 98%, or 99% homogeneous).

As described in further detail herein, the disclosure features substantially homogenous compositions containing Fc constructs that all have the same number of Fc domains, as well as methods of preparing such substantially homogenous compositions.

In a first aspect, the disclosure features an Fc construct including: a) a first polypeptide having the formula A-L-B; wherein i) A includes a first Fc domain monomer; ii) L is a glycine spacer; and iii) B includes a second Fc domain monomer; b) a second polypeptide having the formula A'-L'-B'; wherein i) A' includes a third Fc domain monomer; ii) L' is a glycine spacer; and iii) B' includes a fourth Fc domain monomer; c) a third polypeptide that includes a fifth Fc domain monomer; and d) a fourth polypeptide that includes a sixth Fc domain monomer; wherein B and B' combine to form a first Fc domain, A and the fifth Fc domain monomer combine to form a second Fc domain, and A' and the sixth Fc domain monomer combine to form a third Fc domain.

In some embodiments of this aspect, each of B and B' includes the mutations D399K and K409D, each of A and A' includes the mutations S354C, T366W, and E357K, and each of the fifth and sixth Fc domain monomers includes the mutations Y349C, T366S, L368A, Y407V, and K370D.

In a second aspect, the disclosure features an Fc construct including: a) a first polypeptide having the formula A-L-B; wherein i) A includes a first Fc domain monomer; ii) L is a glycine spacer; and iii) B includes a second Fc domain monomer; b) a second polypeptide having the formula A'-L'-B'; wherein i) A' includes a third Fc domain monomer; ii) L' is a glycine spacer; and iii) B' includes a fourth Fc domain monomer; c) a third polypeptide that includes a fifth Fc domain monomer; and d) a fourth polypeptide that includes a sixth Fc domain monomer; wherein A and A' combine to form a first Fc domain, B and the fifth Fc domain monomer combine to form a second Fc domain, and B' and the sixth Fc domain monomer combine to form a third Fc domain.

In some embodiments of this aspect, each of A and A' includes the mutations D399K and K409D, each of B and B' includes the mutations S354C, T366W, and E357K, and each of the fifth and sixth Fc domain monomers includes the mutations Y349C, T366S, L368A, Y407V, and K370D.

In some embodiments of the previous two aspects of the disclosure, each of L and L' includes at least 4, 8, 12, 14, 16, 18, or 20 glycines. In some embodiments, each of L and L' includes 4-30, 8-30, or 12-30 glycines. In some embodiments, each of L and L' comprises, consists of, or consists essentially of GGGGGGGGGGGGGGGGGGGG (SEQ ID NO: 27).

In some embodiments of the previous two aspects of the disclosure, A consists of an Fc domain monomer. In some embodiments, B consists of an Fc domain monomer. In some embodiments, A' consists of an Fc domain monomer. In some embodiments, B' consists of an Fc domain monomer. In some embodiments, the third polypeptide consists of an Fc domain monomer. In some embodiments, the fourth polypeptide consists of an Fc domain monomer.

In some embodiments, one or more of the Fc domain monomers includes an IgG hinge domain, an IgG $C_H2$ antibody constant domain, and an IgG $C_H3$ antibody constant domain. In some embodiments, each of the Fc domain monomers includes an IgG hinge domain, an IgG $C_H2$ antibody constant domain, and an IgG $C_H3$ antibody constant domain. In some embodiments, each of the Fc domain monomers is an IgG1 Fc domain monomer.

In some embodiments of the previous two aspects of the disclosure, the N-terminal Asp in one or more of the first, second, third, and fourth polypeptides is mutated to Gln. In some embodiments, the N-terminal Asp in each of the first, second, third and fourth polypeptides is mutated to Gln.

In some embodiments, one or more of the first, second, third, and fourth polypeptides lack a C-terminal lysine. In some embodiments, each of the first, second, third, and fourth polypeptides lacks a C-terminal lysine.

In some embodiments of the previous two aspects of the disclosure, the first polypeptide and the second polypeptide have the same amino acid sequence and wherein the third polypeptide and the fourth polypeptide have the same amino acid sequence.

In some embodiments of the first aspect of the disclosure, each of the first and second polypeptides has at least 95% sequence identity (e.g., at least 97%, 99%, or 99.5% sequence identity) to the sequence of
DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVY TLPPCRDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGDKTHTCPPCPA PELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLKSDGSFFLYSDLTVDKSRWQQGNVFSCSVMHEALHNHYTQKSLSLSPG (SEQ ID NO: 49). In some embodiments, each of the first and second polypeptides comprises, consists of, or consists essentially of the sequence of (SEQ ID NO: 49)
DKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVYTLPPCRDKLTKNQVSLWCLV

KGFYPSDIAVEWESNGQPENNYKTTPPVLDSDGSFFLYSKLTVDKSRWQQ

GNVFSCSVMHEALHNHYTQKSLSLSPGKGGGGGGGGGGGGGGGGGGGDK

THTCPPCPAPELLGGPSVFLFPPKPKDTLMISRTPEVTCVVVDVSHEDPE

VKFNVVYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLKSDGSFFLYSDLTVDKSRWQQGN

VFSCSVMHEALHNHYTQKSLSLSPG.

In some embodiments of the disclosure, each of the first and second polypeptides comprises, consists of, or consists essentially of the sequence of
DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYTQKSLSLSPG (SEQ ID NO: 49) with up to 10 (9, 8, 7, 6, 5, 4, 3, 2, or 1) single amino acid modifications (e.g., substitutions, e.g., conservative substitutions).

In some embodiments of the first aspect of the disclosure, each of the third and fourth polypeptides has at least 95% sequence identity (e.g., at least 97%, 99%, or 99.5% sequence identity) to the sequence of
DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSDGSFFLVSKLTVDKSRWQQG NVFSCSVMHEALHNHYTQKSLSLSPG (SEQ ID NO: 48). In some embodiments, each of the third and fourth polypeptides comprises, consists of, or consists essentially of the sequence of (SEQ ID NO: 48)
DKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVCTLPPSRDELTKNQVSLSCAV

DGFYPSDIAVEWESNGQPENNYKTTPPVLDSDGSFFLVSKLTVDKSRWQQ

GNVFSCSVMHEALHNHYTQKSLSLSPG.

In some embodiments of the disclosure, each of the third and fourth polypeptides comprises, consists of, or consists essentially of the sequence of
DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSDGSFFLVSKLTVDKSRWQQG NVFSCSVMHEALHNHYTQKSLSLSPG (SEQ ID NO: 48) with up to 10 (9, 8, 7, 6, 5, 4, 3, 2, or 1) single amino acid modifications (e.g., substitutions, e.g., conservative substitutions).

In some embodiments of the first aspect of the disclosure, each of the first and second polypeptides comprises, consists of, or consists essentially of the sequence of (SEQ ID NO: 49)
DKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVYTLPPCRDKLTKNQVSLWCLV

KGFYPSDIAVEWESNGQPENNYKTTPPVLDSDGSFFLYSKLTVDKSRWQQ

-continued
GNVFSCSVMHEALHNHYTQKSLSLSPGKGGGGGGGGGGGGGGGGGGGGDK

THTCPPCPAPELLGGPSVFLFPPKPKDTLMISRTPEVTCVVVDVSHEDPE

VKFNVVYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLKSDGSFFLYSDLTVDKSRWQQGN

VFSCSVMHEALHNHYTQKSLSLSPG, and
each of the third and fourth polypeptides comprises, consists of, or consists essentially of the sequence of (SEQ ID NO: 48)
DKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVCTLPPSRDELTKNQVSLSCAV

DGFYPSDIAVEWESNGQPENNYKTTPPVLDSDGSFFLVSKLTVDKSRWQQ

GNVFSCSVMHEALHNHYTQKSLSLSPG.

In some embodiments of the first aspect of the disclosure, each of the first and second polypeptides comprises, consists of, or consists essentially of the sequence of
DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQG NVFSCSVMHEALHNHYTQKSLSLSPGKGGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYT QKSLSLSPG (SEQ ID NO: 49), with up to 10 (9, 8, 7, 6, 5, 4, 3, 2, or 1) single amino acid modifications (e.g., substitutions, e.g., conservative substitutions) and each of the third and fourth polypeptides comprises, consists of, or consists essentially of the sequence of
DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSDGSFFLVSKLTVDKSRWQQG NVFSCSVMHEALHNHYTQKSLSLSPG (SEQ ID NO: 48) with up to 10 (9, 8, 7, 6, 5, 4, 3, 2, or 1) single amino acid modifications (e.g., substitutions, e.g., conservative substitutions).

In some embodiments of the first aspect of the disclosure, each of the first and second polypeptides comprises, consists of, or consists essentially of the sequence of
QKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQG NVFSCSVMHEALHNHYTQKSLSLSPGKGGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYT QKSLSLSPG (SEQ ID NO: 60), and each of the third and fourth polypeptides comprises, consists of, or consists essentially of the sequence of (SEQ ID NO: 59)
QKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVCTLPPSRDELTKNQVSLSCAV

DGFYPSDIAVEWESNGQPENNYKTTPPVLDSDGSFFLVSKLTVDKSRWQQ

GNVFSCSVMHEALHNHYTQKSLSLSPG.

In some embodiments of the second aspect of the disclosure, each of the first and second polypeptides comprises, consists of, or consists essentially of at least 95% sequence identity (e.g., at least 97%, 99%, or 99.5% sequence identity) to the sequence of (SEQ ID NO: 61)
DKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLKSDGSFFLYSDLTVDKSRWQQ

GNVFSCSVMHEALHNHYTQKSLSLSPGKGGGGGGGGGGGGGGGGGGGGDK

THTCPPCPAPELLGGPSVFLFPPKPKDTLMISRTPEVTCVVVDVSHEDPE

VKFNVVYVDGVEVHNAKTKPREEQYNSTYRVVSVLTVLHQDWLNGKEYKC

KVSNKALPAPIEKTISKAKGQPREPQVYTLPPCRDKLTKNQVSLWCLVKG

FYPSDIAVEWESNGQPENNYKTTPPVLDSDGSFFLYSKLTVDKSRWQQGN

VFSCSVMHEALHNHYTQKSLSLSPG.

In some embodiments, each of the first and second polypeptides comprises, consists of, or consists essentially of the sequence of (SEQ ID NO: 61)
DKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLKSDGSFFLYSDLTVDKSRWQQ

GNVFSCSVMHEALHNHYTQKSLSLSPGKGGGGGGGGGGGGGGGGGGGGDK

THTCPPCPAPELLGGPSVFLFPPKPKDTLMISRTPEVTCVVVDVSHEDPE

VKFNVVYVDGVEVHNAKTKPREEQYNSTYRVVSVLTVLHQDWLNGKEYKC

-continued

KVSNKALPAPIEKTISKAKGQPREPQVYTLPPCRDKLTKNQVSLWCLVKG

FYPSDIAVEWESNGQPENNYKTTPPVLDSDGSFFLYSKLTVDKSRWQQGN

VFSCSVMHEALHNHYTQKSLSLSPG.

In some embodiments of the disclosure, each of the first and second polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYN-STYRVVSVLTVLHQDWLNGKEYKCKVSNKALPA-PIEKTISKAKGQPREPQVYTLPPS RDELTKNQVSLT-CLVKGFYPSDIAVEWESNGQPENNYKTTPPVLKSD GSFFLYSDLTVDKSRWQQG NVFSCSVMHEALHN-HYTQKSLSL-SPGKGGGGGGGGGGGGGGGGGGGGDKTH-TCPPCPAPELLG GPSVFLFPPKPKDTLMISRTPEVTCVVVDVSHEDPE-VKFNVVYVDGVEVHNAKTKPREEQYNSTYRVV SVLTVLHQDWLNGKEYKCKVSNKALPA-PIEKTISKAKGQPREPQVYTLPPCRDKLT-KNQVSLWCLVK GFYPSDIAVEWESNGQPEN-NYKTTPPVLDSDGSFFLYSKLTVDKSRWQQGNVFS CSVMHEALHNHY TQKSLSLSPG (SEQ ID NO: 61) with up to 10 (9, 8, 7, 6, 5, 4, 3, 2, or 1) single amino acid modifications (e.g., substitutions, e.g., conservative substitutions).

In some embodiments of the second aspect of the disclosure, each of the third and fourth polypeptides has at least 95% sequence identity (e.g., at least 97%, 99%, or 99.5% sequence identity) to the sequence of DKTHTCPPCPAPELLGGPSVFLFPPKPKDTLMISRTPEVTCVVVDVSHEDPEVKFNVVYVDGVEVHNAKTKPREEQYN-STYRVVSVLTVLHQDWLNGKEYKCKVSNKALPA-PIEKTISKAKGQPREPQVCTLPPS RDELTKNQVSLS-CAVDGFYPSDIAVEWESNGQPENNYKTTPPVLDSD GSFFLVSKLTVDKSRWQQG NVFSCSVMHEALHN-HYTQKSLSLSPG (SEQ ID NO: 48). In some embodiments, each of the third and fourth polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYN-STYRVVSVLTVLHQDWLNGKEYKCKVSNKALPA-PIEKTISKAKGQPREPQVCTLPPS RDELTKNQVSLS-CAVDGFYPSDIAVEWESNGQPENNYKTTPPVLDSD GSFFLVSKLTVDKSRWQQG NVFSCSVMHEALHN-HYTQKSLSLSPG (SEQ ID NO: 48). In some embodiments, each of the third and fourth polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYN-STYRVVSVLTVLHQDWLNGKEYKCKVSNKALPA-PIEKTISKAKGQPREPQVCTLPPS RDELTKNQVSLS-CAVDGFYPSDIAVEWESNGQPENNYKTTPPVLDSD GSFFLVSKLTVDKSRWQQG NVFSCSVMHEALHN-HYTQKSLSLSPG (SEQ ID NO: 48) with up to 10 (9, 8, 7, 6, 5, 4, 3, 2, or 1) single amino acid modifications (e.g., substitutions, e.g., conservative substitutions).

In some embodiments of the second aspect of the disclosure, each of the first and second polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYN-STYRVVSVLTVLHQDWLNGKEYKCKVSNKALPA-PIEKTISKAKGQPREPQVYTLPPS RDELTKNQVSLT-CLVKGFYPSDIAVEWESNGQPENNYKTTPPVLKSD GSFFLYSDLTVDKSRWQQG NVFSCSVMHEALHN-HYTQKSLSL-SPGKGGGGGGGGGGGGGGGGGGGGDKTH-TCPPCPAPELLG GPSVFLFPPKPKDTLMISRTPEVTCVVVDVSHEDPE-VKFNVVYVDGVEVHNAKTKPREEQYNSTYRVV SVLTVLHQDWLNGKEYKCKVSNKALPA-PIEKTISKAKGQPREPQVYTLPPCRDKLT-KNQVSLWCLVK GFYPSDIAVEWESNGQPEN-NYKTTPPVLDSDGSFFLYSKLTVDKSRWQQGNVFS CSVMHEALHNHY TQKSLSLSPG (SEQ ID NO: 61), and each of the third and fourth polypeptides comprises, consists of, or consists essentially of the sequence of (SEQ ID NO: 48)
DKTHTCPPCPAPELLGGPSVFLFPPKPKDTLMISRTPEVTCVVVDVSHED

PEVKFNVVYVDGVEVHNAKTKPREEQYNSTYRVVSVLTVLHQDWLNGKEY

KCKVSNKALPAPIEKTISKAKGQPREPQVCTLPPSRDELTKNQVSLSCAV

DGFYPSDIAVEWESNGQPENNYKTTPPVLDSDGSFFLVSKLTVDKSRWQQ

GNVFSCSVMHEALHNHYTQKSLSLSPG.

In some embodiments of the second aspect of the disclosure, each of the first and second polypeptides comprises, consists of, or consists essentially of the sequence of QKTHTCPPCPAPELLGGPSVFLFPPKPKDTLMISRTPEVTCVVVDVSHEDPEVKFNVVYVDGVEVHNAKTKPREEQYN-STYRVVSVLTVLHQDWLNGKEYKCKVSNKALPA-PIEKTISKAKGQPREPQVYTLPPS RDELTKNQVSLT-CLVKGFYPSDIAVEWESNGQPENNYKTTPPVLKSD GSFFLYSDLTVDKSRWQQG NVFSCSVMHEALHN-HYTQKSLSL-SPGKGGGGGGGGGGGGGGGGGGGGDKTH-TCPPCPAPELLG GPSVFLFPPKPKDTLMISRTPEVTCVVVDVSHEDPE-VKFNVVYVDGVEVHNAKTKPREEQYNSTYRVV SVLTVLHQDWLNGKEYKCKVSNKALPA-PIEKTISKAKGQPREPQVYTLPPCRDKLT-KNQVSLWCLVK GFYPSDIAVEWESNGQPEN-NYKTTPPVLDSDGSFFLYSKLTVDKSRWQQGNVFS CSVMHEALHNHY TQKSLSLSPG (SEQ ID NO: 62), and each of the third and fourth polypeptides comprises, consists of, or consists essentially of the sequence of (SEQ ID NO: 59)
QKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVCTLPPSRDELTKNQVSLSC

AVDGFYPSDIAVEWESNGQPENNYKTTPPVLDSDGSFFLVSKLTVDKSR

WQQGNVFSCSVMHEALHNHYTQKSLSLSPG.

In another aspect, the disclosure features an Fc construct including: a) a first polypeptide having the formula A-L-B; wherein i) A includes a first Fc domain monomer; ii) L is a linker; and iii) B includes a second Fc domain monomer; b) a second polypeptide having the formula A'-L'-B'; wherein i) A' includes a third Fc domain monomer; ii) L' is a linker; and iii) B' includes a fourth Fc domain monomer; c) a third polypeptide that includes a fifth Fc domain monomer; and d) a fourth polypeptide that includes a sixth Fc domain monomer; wherein B and B' combine to form a first Fc domain, A and the fifth Fc domain monomer combine to form a second Fc domain, and A' and the sixth Fc domain monomer combine to form a third Fc domain, and wherein the first polypeptide and the second polypeptide each comprises, consists of, or consists essentially of the sequence of SEQ ID NO: 49 and wherein the third polypeptide and the fourth polypeptide each comprises, consists of, or consists essentially of the sequence of SEQ ID NO: 48.

In another aspect, the disclosure features an Fc construct including: a) a first polypeptide having the formula A-L-B; wherein i) A includes a first Fc domain monomer; ii) L is a linker; and iii) B includes a second Fc domain monomer; b) a second polypeptide having the formula A'-L'-B'; wherein i) A' includes a third Fc domain monomer; ii) L' is a linker; and iii) B' includes a fourth Fc domain monomer; c) a third polypeptide that includes a fifth Fc domain monomer; and d) a fourth polypeptide that includes a sixth Fc domain monomer; wherein A and A' combine to form a first Fc domain, B and the fifth Fc domain monomer combine to form a second Fc domain, and B' and the sixth Fc domain monomer combine to form a third Fc domain, and wherein the first polypeptide and the second polypeptide each comprises, consists of, or consists essentially of the sequence of SEQ ID NO: 61 and wherein the third polypeptide and the fourth polypeptide each comprises, consists of, or consists essentially of the sequence of SEQ ID NO: 48.

In another aspect, the disclosure features an Fc construct including: a) a first polypeptide having the formula A-L-B; wherein i) A includes a first Fc domain monomer; ii) L is a glycine spacer; and iii) B includes a second Fc domain monomer; b) a second polypeptide including a third Fc domain monomer; and c) a third polypeptide including a fourth Fc domain monomer; wherein the first Fc domain monomer and the third Fc domain monomer combine to form a first Fc domain and the second Fc domain monomer and the fourth Fc domain monomer combine to form a second Fc domain.

In some embodiments of this aspect of the disclosure, each of the first and third Fc domain monomers includes a complementary dimerization selectivity module that promote dimerization between the first Fc domain monomer and the third Fc domain monomer, and each of the second and fourth Fc domain monomers includes a complementary dimerization selectivity module that promote dimerization between the second Fc domain monomer and the fourth Fc domain monomer. In some embodiments, the complementary dimerization selectivity module of each of the first and second Fc domain monomers includes an engineered protuberance, and the complementary dimerization selectivity module of each of the third and fourth Fc domain monomers includes an engineered cavity.

In some embodiments of this aspect of the disclosure, L includes at least 4, 8, or 12 glycines. In some embodiments, L includes 4-30, 8-30, or 12-30 glycines. In some embodiments, L comprises, consists of, or consists essentially of the sequence of GGGGGGGGGGGGGGGGGGGGG (SEQ ID NO: 27).

In some embodiments of this aspect of the disclosure, one or more of A, B, the second polypeptide, and the third polypeptide consists of an Fc domain monomer. In some embodiments, each of A, B, the second polypeptide, and the third polypeptide consists of an Fc domain monomer.

In some embodiments of this aspect of the disclosure, the N-terminal Asp in one or more of the first, second, and third polypeptides is mutated to Gln. In some embodiments, the N-terminal Asp in each of the first, second, and third polypeptides is mutated to Gln.

In some embodiments of this aspect of the disclosure, one or more of the first, second, and third polypeptides lacks a C-terminal lysine. In some embodiments, each of the first, second, and third polypeptides lacks a C-terminal lysine In some embodiments of this aspect of the disclosure, the second polypeptide and the third polypeptide have the same amino acid sequence.

In another aspect, the disclosure features an Fc construct including: a) a first polypeptide having the formula A-L1-B-L2-C; wherein i) A includes a first Fc domain monomer; ii) L1 is a glycine spacer; iii) B includes a second Fc domain monomer; iv) L2 is a glycine spacer; and v) C includes a third Fc domain monomer; b) a second polypeptide having the formula A'-L1'-B'-L2'-C'; wherein i) A' includes a fourth Fc domain monomer; ii) L1' is a glycine spacer; iii) B' includes a fifth Fc domain monomer; iv) L2' is a glycine spacer; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein A and the seventh Fc domain monomer combine to form a first Fc domain, B and B' combine to form a second Fc domain, C and the eighth Fc domain monomer combine to form a third Fc domain, A' and the ninth Fc domain monomer combine to form a fourth Fc domain, and C' and the tenth Fc domain monomer combine to form a fifth Fc domain.

In some embodiments of this aspect of the disclosure, each of the first and seventh Fc domain monomers includes a complementary dimerization selectivity module that promote dimerization between the first Fc domain monomer and the seventh Fc domain monomer, each of the second and fifth Fc domain monomers includes a complementary dimerization selectivity module that promote dimerization between the second Fc domain monomer and the fifth Fc domain monomer, each of the third and eighth Fc domain monomers includes a complementary dimerization selectivity module that promote dimerization between the third Fc domain monomer and the eighth Fc domain monomer; each of the fourth and ninth Fc domain monomers includes a complementary dimerization selectivity module that promote dimerization between the fourth Fc domain monomer and the ninth Fc domain monomer; and each of the sixth and tenth Fc domain monomers includes a complementary dimerization selectivity module that promote dimerization between the sixth Fc domain monomer and the tenth Fc domain monomer.

In some embodiments, the complementary dimerization selectivity module of the second Fc domain monomer includes a negatively-charged amino acid substitution, the complementary dimerization selectivity module of the fifth Fc domain monomer includes a positively-charged amino acid substitution, the complementary dimerization selectivity module of each of the first, third, fourth, and sixth Fc domain monomers includes an engineered protuberance, and complementary dimerization selectivity module of each of the seventh, eighth, ninth, and tenth Fc domain monomers includes an engineered cavity.

In another aspect, the disclosure features an Fc construct including: a) a first polypeptide having the formula A-L1-B-L2-C; wherein i) A includes a first Fc domain monomer; ii) L1 is a glycine spacer; iii) B includes a second Fc domain monomer; iv) L2 is a glycine spacer; and v) C includes a third Fc domain monomer; b) a second polypeptide having the formula A'-L1'-B'-L2'-C'; wherein i) A' includes a fourth Fc domain monomer; ii) L1' is a glycine spacer; iii) B' includes a fifth Fc domain monomer; iv) L2' is a glycine spacer; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein C and C' combine to form a first Fc domain, B and the seventh Fc domain monomer combine to form a second Fc domain, A and the eighth Fc domain monomer combine to form a third Fc domain, B' and the ninth Fc domain monomer combine to form a fourth Fc domain, and A' and the tenth Fc domain monomer combine to form a fifth Fc domain.

In some embodiments of this aspect of the disclosure, each of the third and sixth Fc domain monomers includes complementary dimerization selectivity modules that promote dimerization between the third Fc domain monomer and the sixth Fc domain monomer, each of the second and seventh Fc domain monomers includes complementary dimerization selectivity modules that promote dimerization between the second Fc domain monomer and the seventh Fc domain monomer, each of the first and eighth Fc domain monomers includes complementary dimerization selectivity modules that promote dimerization between the first Fc domain monomer and the eighth Fc domain monomer;

each of the fifth and ninth Fc domain monomers includes complementary dimerization selectivity modules that promote dimerization between the fifth Fc domain monomer and the ninth Fc domain monomer; and each of the fourth and tenth Fc domain monomers includes complementary dimerization selectivity modules that promote dimerization between the fourth Fc domain monomer and the tenth Fc domain monomer.

In some embodiments, the complementary dimerization selectivity module of the third Fc domain monomer includes a negatively-charged amino acid substitution, the complementary dimerization selectivity module of the sixth Fc domain monomer includes a positively-charged amino acid substitution, the complementary dimerization selectivity module of each of the first, second, fourth, and fifth Fc domain monomers includes an engineered protuberance, and complementary dimerization selectivity module of each of the seventh, eighth, ninth, and tenth Fc domain monomers includes an engineered cavity.

In another aspect, the disclosure features an Fc construct including: a) a first polypeptide having the formula A-L1-B-L2-C; wherein i) A includes a first Fc domain monomer; ii) L1 is a glycine spacer; iii) B includes a second Fc domain monomer; iv) L2 is a glycine spacer; and v) C includes a third Fc domain monomer; b) a second polypeptide having the formula A'-L1'-B'-L2'-C'; wherein i) A' includes a fourth Fc domain monomer; ii) L1' is a glycine spacer; iii) B' includes a fifth Fc domain monomer; iv) L2' is a glycine spacer; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein A and A' combine to form a first Fc domain, B and the seventh Fc domain monomer combine to form a second Fc domain, C and the eighth Fc domain monomer combine to form a third Fc domain, B' and the ninth Fc domain monomer combine to form a fourth Fc domain, and C' and the tenth Fc domain monomer combine to form a fifth Fc domain.

In some embodiments of this aspect of the disclosure, each of the first and fourth Fc domain monomers includes complementary dimerization selectivity modules that promote dimerization between the first Fc domain monomer and the fourth Fc domain monomer, each of the second and seventh Fc domain monomers includes complementary dimerization selectivity modules that promote dimerization between the second Fc domain monomer and the seventh Fc domain monomer, each of the third and eighth Fc domain monomers includes complementary dimerization selectivity modules that promote dimerization between the third Fc domain monomer and the eighth Fc domain monomer; each of the fifth and ninth Fc domain monomers includes complementary dimerization selectivity modules that promote dimerization between the fifth Fc domain monomer and the ninth Fc domain monomer; and each of the sixth and tenth Fc domain monomers includes complementary dimerization selectivity modules that promote dimerization between the sixth Fc domain monomer and the tenth Fc domain monomer.

In some embodiments, the complementary dimerization selectivity module of the first Fc domain monomer includes a negatively-charged amino acid substitution, the complementary dimerization selectivity module of the fourth Fc domain monomer includes a positively-charged amino acid substitution, the complementary dimerization selectivity module of each of the second, third, fifth, and sixth Fc domain monomers includes an engineered protuberance, and complementary dimerization selectivity module of each of the seventh, eighth, ninth, and tenth Fc domain monomers includes an engineered cavity.

In some embodiments of Fc constructs having five Fc domains as described herein, each of L1, L2, L1', and L2' includes at least 4, 8, or 12 glycines. In some embodiments, each of L1, L2, L1', and L2' includes 4-30, 8-30, or 12-30 glycines. In some embodiments, each of L1, L2, L1', and L2' comprises, consists of, or consists essentially of the sequence of GGGGGGGGGGGGGGGGGGGG (SEQ ID NO: 27).

In some embodiments of Fc constructs having five Fc domains as described herein, each of A, B, C, A', B', C', the third polypeptide, the fourth polypeptide, the fifth polypeptide, and the six polypeptide consists of an Fc domain monomer.

In some embodiments of Fc constructs having five Fc domains as described herein, the N-terminal Asp in one or more of the first, second, third, fourth, fifth, and sixth polypeptides is mutated to Gln. In some embodiments, the N-terminal Asp in each of the first, second, third, fourth, fifth, and sixth polypeptides is mutated to Gln.

In some embodiments, one or more of the first, second, third, fourth, fifth, and sixth polypeptides lacks a C-terminal lysine. In some embodiments, each of the first, second, third, fourth, fifth, and sixth polypeptides lacks a C-terminal lysine.

In some embodiments, the first polypeptide and the second polypeptide have the same amino acid sequence, and the third, fourth, fifth, and sixth polypeptides have the same amino acid sequence.

In another aspect, the disclosure features an Fc construct including: a) a first polypeptide having the formula A-L1-B-L2-C; wherein i) A includes a first Fc domain monomer; ii) L1 is a linker; iii) B includes a second Fc domain monomer; iv) L2 is a glycine spacer; v) C includes a third Fc domain monomer; and b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a glycine spacer; v) C' includes a sixth Fc domain monomer; wherein the first Fc domain monomer and the second Fc domain monomer combine to form a first Fc domain, the fourth Fc domain monomer and the fifth Fc domain monomer combine to form a second Fc domain, and the third Fc domain monomer and the sixth Fc domain monomer combine to form a third Fc domain.

In some embodiments of this aspect of the disclosure, each of the first and second Fc domain monomers includes complementary dimerization selectivity modules that promote dimerization between the first Fc domain monomer and the second Fc domain monomer, each of the fourth and fifth Fc domain monomers includes complementary dimerization selectivity modules that promote dimerization between the fourth Fc domain monomer and the fifth Fc domain monomer, and each of the third and sixth Fc domain monomers includes complementary dimerization selectivity modules that promote dimerization between the third Fc domain monomer and the sixth Fc domain monomer.

In some embodiments, the complementary dimerization selectivity module of each of the first and fourth Fc domain monomers includes an engineered protuberance, the complementary dimerization selectivity module of each of the second and fifth Fc domain monomer includes an engineered cavity, the complementary dimerization selectivity module of the third Fc domain monomer includes a negatively-charged amino acid substitution, and the complementary dimerization selectivity module of the sixth Fc domain monomer includes a positively-charged amino acid substitution, In some embodiments of this aspect of the disclosure, each of L2 and L2' includes at least 12 glycines. In some embodiments, each of L2 and L2' includes 4-30, 8-30, or 12-30 glycines. In some embodiments, each of L2 and L2' comprises, consists of, or consists essentially of the sequence of

GGGGGGGGGGGGGGGGGGGG. (SEQ ID NO: 27)

In some embodiments of this aspect of the disclosure, each of A, B, C, A', B', and C' consists of an Fc domain monomer.

In some embodiments of this aspect of the disclosure, the first polypeptide and the second polypeptide have the same amino acid sequence.

In another aspect, the disclosure features an Fc construct including: a) a first polypeptide having the formula A-L-B; wherein i) A includes a first Fc domain monomer; ii) L is a linker; iii) B includes a second Fc domain monomer; b) a second polypeptide having the formula A'-L'-B'; wherein i) A' includes a third Fc domain monomer; ii) L' is a linker; iii) B' includes a fourth Fc domain monomer; wherein the first Fc domain monomer and the third Fc domain monomer combine to form a first Fc domain, and the second Fc domain monomer and the fourth Fc domain monomer combine to form a second Fc domain, and wherein at least one of L and L' is a glycine spacer.

In some embodiments of this aspect, each of the first and third Fc domain monomers includes complementary dimerization selectivity modules that promote dimerization between the first Fc domain monomer and the third Fc domain monomer, and each of the second and fourth Fc domain monomers includes complementary dimerization selectivity modules that promote dimerization between the second Fc domain monomer and the fourth Fc domain monomer.

In some embodiments of this aspect, the complementary dimerization selectivity module of each of the first and second Fc domain monomers includes an engineered protuberance, and the complementary dimerization selectivity module of each of the third and fourth Fc domain monomer includes an engineered cavity.

In some embodiments of this aspect, at least one of L and L' includes at least 4, 8, or 12 glycines. In some embodiments, at least one of L and L' includes 4-30, 8-30, or 12-30 glycines. In some embodiments, at least one of L and L' comprises, consists of, or consists essentially of the sequence of GGGGGGGGGGGGGGGGGGGG (SEQ ID NO: 27). In some embodiments of this aspect, each of L and L' includes at least 4, 8, or 12 glycines. In some embodiments, each of L and L' includes 4-30, 8-30, or 12-30 glycines. In some embodiments, each of L and L' comprises, consists of, or consists essentially of the sequence of GGGGGGGGGGGGGGGGGGGG (SEQ ID NO: 27).

In some embodiments of this aspect, one or more of A, B, A', and B' consists of an Fc domain monomer. In some embodiments of this aspect, each of A, B, A', and B' consists of an Fc domain monomer.

In some embodiments of the previous two aspects of the disclosure, the N-terminal Asp in one or more of the first and second polypeptides is mutated to Gln. In some embodiments, the N-terminal Asp in each of the first and second polypeptides is mutated to Gln.

In some embodiments of the previous two aspects of the disclosure, one or more of the first and second polypeptides lacks a C-terminal lysine. In some embodiments, each of the first and second polypeptides lacks a C-terminal lysine.

In some embodiments, each of the Fc domain monomers in an Fc construct described herein includes an IgG hinge domain, an IgG $C_H2$ antibody constant domain, and an IgG $C_H3$ antibody constant domain. In some embodiments, each of the Fc domain monomers in an Fc construct described herein is an IgG1 Fc domain monomer.

In another aspect, the disclosure features a composition including a substantially homogenous population of an Fc construct including: a) a first polypeptide having the formula A-L-B; wherein i) A includes a first Fc domain monomer; ii) L is a glycine spacer; and iii) B includes a second Fc domain monomer; b) a second polypeptide having the formula A'-L'-B'; wherein i) A' includes a third Fc domain monomer; ii) L' is a glycine spacer; and iii) B' includes a fourth Fc domain monomer; c) a third polypeptide that includes a fifth Fc domain monomer; and d) a fourth polypeptide that includes a sixth Fc domain monomer; wherein B and B' combine to form a first Fc domain, A and the fifth Fc domain monomer combine to form a second Fc domain, and A' and the sixth Fc domain monomer combine to form a third Fc domain.

In some embodiments of this aspect, each of B and B' includes the mutations D399K and K409D, each of A and A' includes the mutations S354C, T366W, and E357K, and each of the fifth and sixth Fc domain monomers includes the mutations Y349C, T366S, L368A, Y407V, and K370D.

In some embodiments of this aspect, the first polypeptide and the second polypeptide have the same amino acid sequence and wherein the third polypeptide and the fourth polypeptide have the same amino acid sequence in the Fc construct in the composition.

In some embodiments, each of the first and second polypeptides has at least 95% sequence identity (e.g., at least 97%, 99%, or 99.5% sequence identity) to the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYT QKSLSLSPG (SEQ ID NO: 49). In some embodiments, each of the first and second polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYT QKSLSLSPG (SEQ ID NO: 49). In some embodiments, each of the first and second polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYT QKSLSLSPG (SEQ ID NO: 49) with up to 10 (9, 8, 7, 6, 5, 4, 3, 2, or 1) single amino acid modifications (e.g., substitutions, e.g., conservative substitutions).

In some embodiments, each of the third and fourth polypeptides has at least 95% sequence identity (e.g., at least 97%, 99%, or 99.5% sequence identity) to the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSDGSFFLVSKLTVDKSRWQQG NVFSCSVMHEALHNHYTQKSLSLSPG (SEQ ID NO: 48). In some embodiments, each of the third and fourth polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSDGSFFLVSKLTVDKSRWQQG NVFSCSVMHEALHNHYTQKSLSLSPG (SEQ ID NO: 48). In some embodiments of the disclosure, each of the third and fourth polypeptides comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSDGSFFLVSKLTVDKSRWQQG NVFSCSVMHEALHNHYTQKSLSLSPG (SEQ ID NO: 48) with up to 10 (9, 8, 7, 6, 5, 4, 3, 2, or 1) single amino acid modifications (e.g., substitutions, e.g., conservative substitutions).

In some embodiments of this aspect, each of the first and second polypeptides in the Fc construct in the composition comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYT QKSLSLSPG (SEQ ID NO: 49), and each of the third and fourth polypeptides in the Fc construct in the composition comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLS- CAVDGFYPSDIAVEWESNGQPENNYKTTPPVLDSD GSFFLVSKLTVDKSRWQQG NVFSCSVMHEALHNHYTQKSLSLSPG (SEQ ID NO: 48). In some embodiments, the Fc construct comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQG NVFSCSVMHEALHNHYTQKSLSLSPGKGGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFSCSVMHEALHNHYT QKSLSLSPG (SEQ ID NO: 49) with up to 10 (9, 8, 7, 6, 5, 4, 3, 2, or 1) single amino acid modifications (e.g., substitutions, e.g., conservative substitutions), and each of the third and fourth polypeptides in the Fc construct in the composition comprises, consists of, or consists essentially of the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSD GSFFLVSKLTVDKSRWQQG NVFSCSVMHEALHNHYTQKSLSLSPG (SEQ ID NO: 48) with up to 10 (9, 8, 7, 6, 5, 4, 3, 2, or 1) single amino acid modifications (e.g., substitutions, e.g., conservative substitutions). In some cases, any one of the Fc constructs described herein has anti-inflammatory activity.

In some embodiments of any of the Fc constructs described herein, one or more of the Fc domain monomers is an IgG Fc domain monomer (e.g., an IgG1, IgG2a, IgG2b. IgG3, or IgG4). In some cases, one or more of the Fc domain monomers is an IgG Fc domain monomer having up to ten amino acid modifications (e.g., up to 1, 2, 3, 4, 5, 6, 7, 8, 9, or 10 amino acid modifications). In some cases, each Fc domain monomer has no more than ten amino acid modifications (e.g., up to 1, 2, 3, 4, 5, 6, 7, 8, 9, or 10 amino acid modifications).

In another aspect, the disclosure features a composition including a substantially homogenous population of an Fc construct including: a) a first polypeptide having the formula A-L-B; wherein i) A includes a first Fc domain monomer; ii) Lisa glycine spacer; and iii) B includes a second Fc domain monomer; b) a second polypeptide having the formula A'-L'-B'; wherein i) A' includes a third Fc domain monomer; ii) L' is a glycine spacer; and iii) B' includes a fourth Fc domain monomer; c) a third polypeptide that includes a fifth Fc domain monomer; and d) a fourth polypeptide that includes a sixth Fc domain monomer; wherein A and A' combine to form a first Fc domain, B and the fifth Fc domain monomer combine to form a second Fc domain, and B' and the sixth Fc domain monomer combine to form a third Fc domain.

In some embodiments of this aspect, each of A and A' includes the mutations D399K and K409D, each of B and B' includes the mutations S354C, T366W, and E357K, and each of the fifth and sixth Fc domain monomers includes the mutations Y349C, T366S, L368A, Y407V, and K370D.

In some embodiments of this aspect, the first polypeptide and the second polypeptide have the same amino acid sequence and wherein the third polypeptide and the fourth polypeptide have the same amino acid sequence in the Fc construct in the composition. In some embodiments, the first polypeptide and the second polypeptide have the same amino acid sequence (e.g., SEQ ID NO: 49) and wherein the third polypeptide and the fourth polypeptide have the same amino acid sequence (e.g., SEQ ID NO: 48) in the Fc construct in the composition.

In some embodiments of this aspect, each of the first and second polypeptides has at least 95% sequence identity (e.g., at least 97%, 99%, or 99.5% sequence identity) to the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLKSDGSFFLYSDLTVDKSRWQQG NVFSCSVMHEALHNHYTQKSLSLSPGKGGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPCRDKLTKNQVSLWCLVK GFYPSDIAVEWESNGQPENNYKTTPPVLDSDGSFFLYSKLTVDKSRWQQGNVFS CSVMHEALHNHY TQKSLSLSPG (SEQ ID NO: 61). In some embodiments, each of the first and second polypeptides comprises, consists of, or consists essentially of the sequence of

```
                                    (SEQ ID NO: 61)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLKSDGSFFLYSDLTVDKSR

WQQGNVFSCSVMHEALHNHYTQKSLSLSPGKGGGGGGGGGGGGGGGGGGG

GGDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNG

KEYKCKVSNKALPAPIEKTISKAKGQPREPQVYTLPPCRDKLTKNQVSL

WCLVKGFYPSDIAVEWESNGQPENNYKTTPPVLDSDGSFFLYSKLTVDK

SRWQQGNVFSCSVMHEALHNHYTQKSLSLSPG.
```

In some embodiments of this aspect, each of the third and fourth polypeptides has at least 95% sequence identity (e.g., at least 97%, 99%, or 99.5% sequence identity) to the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSD GSFFLVSKLTVDKSRWQQG NVFSCSVMHEALHNHYTQKSLSLSPG (SEQ ID NO:

48). In some embodiments, each of the third and fourth polypeptides comprises, consists of, or consists essentially of the sequence of

```
                                           (SEQ ID NO: 48)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVCTLPPSRDELTKNQVSLSC

AVDGFYPSDIAVEWESNGQPENNYKTTPPVLDSDGSFFLVSKLTVDKSR

WQQGNVFSCSVMHEALHNHYTQKSLSLSPG.
```

In some embodiments of this aspect, each of the first and second polypeptides in the Fc construct in the composition comprises, consists of, or consists essentially of the sequence of DKTHTCPPCPAPELLGGPSVFLFPPKPKDTLMISRTPE-VTCVVVDVSHEDPEVKFNVVYVDGVEVHNA KTKPREEQYN-STYRVVSVLTVLHQDWLNGKEYKCKVSNKALPA-PIEKTISKAKGQPREPQVYTLPPS RDELTKNQVSLT-CLVKGFYPSDIAVEWESNGQPENNYKTTPPVLKSDG SFFLYSDLTVDKSRWQQG NVFSCSVMHEALHN-HYTQKSLSL-SPGKGGGGGGGGGGGGGGGGGGGGGGGDKTH-TCPPCPAPELLG GPSVFLFPPKPKDTLMISRTPEVTCVVVDVSHEDPE-VKFNVVYVDGVEVHNAKTKPREEQYNSTYRVV SVLTVLHQDWLNGKEYKCKVSNKALPA-PIEKTISKAKGQPREPQVYTLPPCRDKLT-KNQVSLWCLVK GFYPSDIAVEWESNGQPEN-NYKTTPPVLDSDGSFFLYSKLTVDKSRWQQGNVFS CSVMHEALHNHY TQKSLSLSPG (SEQ ID NO: 61), and each of the third and fourth polypeptides in the Fc construct in the composition comprises, consists of, or consists essentially of the sequence of

```
                                           (SEQ ID NO: 48)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVCTLPPSRDELTKNQVSLSC

AVDGFYPSDIAVEWESNGQPENNYKTTPPVLDSDGSFFLVSKLTVDKSR

WQQGNVFSCSVMHEALHNHYTQKSLSLSPG.
```

In another aspect, the disclosure features a composition including a substantially homogenous population of an Fc construct including: a) a first polypeptide having the formula A-L-B; wherein i) A includes a first Fc domain monomer; ii) L is a linker; and iii) B includes a second Fc domain monomer; b) a second polypeptide having the formula A'-L'-B'; wherein i) A' includes a third Fc domain monomer; ii) L' is a linker; and iii) B' includes a fourth Fc domain monomer; c) a third polypeptide that includes a fifth Fc domain monomer; and d) a fourth polypeptide that includes a sixth Fc domain monomer; wherein B and B' combine to form a first Fc domain, A and the fifth Fc domain monomer combine to form a second Fc domain, and A' and the sixth Fc domain monomer combine to form a third Fc domain, and wherein the first polypeptide and the second polypeptide each comprises, consists of, or consists essentially of the sequence of SEQ ID NO: 49 and wherein the third polypeptide and the fourth polypeptide each comprises, consists of, or consists essentially of the sequence of SEQ ID NO: 48.

In another aspect, the disclosure features a composition including a substantially homogenous population of an Fc construct including: a) a first polypeptide having the formula A-L-B; wherein i) A includes a first Fc domain monomer; ii) L is a linker; and iii) B includes a second Fc domain monomer; b) a second polypeptide having the formula A'-L'-B'; wherein i) A' includes a third Fc domain monomer; ii) L' is a linker; and iii) B' includes a fourth Fc domain monomer; c) a third polypeptide that includes a fifth Fc domain monomer; and d) a fourth polypeptide that includes a sixth Fc domain monomer; wherein A and A' combine to form a first Fc domain, B and the fifth Fc domain monomer combine to form a second Fc domain, and B' and the sixth Fc domain monomer combine to form a third Fc domain, and wherein the first polypeptide and the second polypeptide each comprises, consists of, or consists essentially of the sequence of SEQ ID NO: 61 and wherein the third polypeptide and the fourth polypeptide each comprises, consists of, or consists essentially of the sequence of SEQ ID NO: 48.

In another aspect, the disclosure features a composition including a substantially homogenous population of an Fc construct including: a) a first polypeptide having the formula A-L-B; wherein i) A includes a first Fc domain monomer; ii) L is a glycine spacer; and iii) B includes a second Fc domain monomer; b) a second polypeptide including a third Fc domain monomer; and c) a third polypeptide including a fourth Fc domain monomer; wherein the first Fc domain monomer and the third Fc domain monomer combine to form a first Fc domain and the second Fc domain monomer and the fourth Fc domain monomer combine to form a second Fc domain.

In some embodiments of this aspect, each of the first and third Fc domain monomers in the Fc construct in the composition includes a complementary dimerization selectivity module that promote dimerization between the first Fc domain monomer and the third Fc domain monomer, and each of the second and fourth Fc domain monomers in the Fc construct in the composition includes a complementary dimerization selectivity module that promote dimerization between the second Fc domain monomer and the fourth Fc domain monomer.

In some embodiments of this aspect, the complementary dimerization selectivity module of each of the first and second Fc domain monomers includes an engineered protuberance, and the complementary dimerization selectivity module of each of the third and fourth Fc domain monomers includes an engineered cavity.

In some embodiments of this aspect, the second polypeptide and the third polypeptide have the same amino acid sequence.

In another aspect, the disclosure features a composition including a substantially homogenous population of an Fc construct including: a) a first polypeptide having the formula A-L1-B-L2-C; wherein i) A includes a first Fc domain monomer; ii) L1 is a glycine spacer; iii) B includes a second Fc domain monomer; iv) L2 is a glycine spacer; and v) C includes a third Fc domain monomer; b) a second polypeptide having the formula A'-L1'-B'-L2'-C'; wherein i) A' includes a fourth Fc domain monomer; ii) L1' is a glycine spacer; iii) B' includes a fifth Fc domain monomer; iv) L2' is a glycine spacer; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein A and the seventh Fc domain monomer combine to form a first Fc domain, B and B' combine to form a second Fc domain, C and the eighth Fc domain monomer combine to form a third Fc domain, A' and the ninth Fc domain monomer combine to form a fourth Fc domain, and C' and the tenth Fc domain monomer combine to form a fifth Fc domain.

In some embodiments of this aspect, each of the first and seventh Fc domain monomers in the Fc construct in the composition includes a complementary dimerization selectivity module that promote dimerization between the first Fc domain monomer and the seventh Fc domain monomer; each of the second and fifth Fc domain monomers in the Fc construct in the composition includes a complementary dimerization selectivity module that promote dimerization between the second Fc domain monomer and the fifth Fc domain monomer; each of the third and eighth Fc domain monomers in the Fc construct in the composition includes a complementary dimerization selectivity module that promote dimerization between the third Fc domain monomer and the eighth Fc domain monomer; each of the fourth and ninth Fc domain monomers in the Fc construct in the composition includes a complementary dimerization selectivity module that promote dimerization between the fourth Fc domain monomer and the ninth Fc domain monomer; and each of the sixth and tenth Fc domain monomers in the Fc construct in the composition includes a complementary dimerization selectivity module that promote dimerization between the sixth Fc domain monomer and the tenth Fc domain monomer.

In some embodiments of this aspect, the complementary dimerization selectivity module of the second Fc domain monomer includes a negatively-charged amino acid substitution, the complementary dimerization selectivity module of the fifth Fc domain monomer includes a positively-charged amino acid substitution, the complementary dimerization selectivity module of each of the first, third, fourth, and sixth Fc domain monomers includes an engineered protuberance, and complementary dimerization selectivity module of each of the seventh, eighth, ninth, and tenth Fc domain monomers includes an engineered cavity.

In another aspect, the disclosure features a composition including a substantially homogenous population of an Fc construct including: a) a first polypeptide having the formula A-L1-B-L2-C; wherein i) A includes a first Fc domain monomer; ii) L1 is a glycine spacer; iii) B includes a second Fc domain monomer; iv) L2 is a glycine spacer; and v) C includes a third Fc domain monomer; b) a second polypeptide having the formula A'-L1'-B'-L2'-C'; wherein i) A' includes a fourth Fc domain monomer; ii) L1' is a glycine spacer; iii) B' includes a fifth Fc domain monomer; iv) L2' is a glycine spacer; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein C and C' combine to form a first Fc domain, B and the seventh Fc domain monomer combine to form a second Fc domain, A and the eighth Fc domain monomer combine to form a third Fc domain, B' and the ninth Fc domain monomer combine to form a fourth Fc domain, and A' and the tenth Fc domain monomer combine to form a fifth Fc domain.

In some embodiments of this aspect, each of the third and sixth Fc domain monomers in the Fc construct in the composition includes complementary dimerization selectivity modules that promote dimerization between the third Fc domain monomer and the sixth Fc domain monomer; each of the second and seventh Fc domain monomers in the Fc construct in the composition includes complementary dimerization selectivity modules that promote dimerization between the second Fc domain monomer and the seventh Fc domain monomer; each of the first and eighth Fc domain monomers in the Fc construct in the composition includes complementary dimerization selectivity modules that promote dimerization between the first Fc domain monomer and the eighth Fc domain monomer; each of the fifth and ninth Fc domain monomers in the Fc construct in the composition includes complementary dimerization selectivity modules that promote dimerization between the fifth Fc domain monomer and the ninth Fc domain monomer; and each of the fourth and tenth Fc domain monomers in the Fc construct in the composition includes complementary dimerization selectivity modules that promote dimerization between the fourth Fc domain monomer and the tenth Fc domain monomer.

In some embodiments of this aspect, the complementary dimerization selectivity module of the third Fc domain monomer includes a negatively-charged amino acid substitution, the complementary dimerization selectivity module of the sixth Fc domain monomer includes a positively-charged amino acid substitution, the complementary dimerization selectivity module of each of the first, second, fourth, and fifth Fc domain monomers includes an engineered protuberance, and complementary dimerization selectivity module of each of the seventh, eighth, ninth, and tenth Fc domain monomers includes an engineered cavity.

In another aspect, the disclosure features a composition including a substantially homogenous population of an Fc construct including: a) a first polypeptide having the formula A-L1-B-L2-C; wherein i) A includes a first Fc domain monomer; ii) L1 is a glycine spacer; iii) B includes a second Fc domain monomer; iv) L2 is a glycine spacer; and v) C includes a third Fc domain monomer; b) a second polypeptide having the formula A'-L1'-B'-L2'-C'; wherein i) A' includes a fourth Fc domain monomer; ii) L1' is a glycine spacer; iii) B' includes a fifth Fc domain monomer; iv) L2' is a glycine spacer; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein A and A' combine to form a first Fc domain, B and the seventh Fc domain monomer combine to form a second Fc domain, C and the eighth Fc domain monomer combine to form a third Fc domain, B' and the ninth Fc domain monomer combine to form a fourth Fc domain, and C' and the tenth Fc domain monomer combine to form a fifth Fc domain.

In some embodiments of this aspect, each of the first and fourth Fc domain monomers in the Fc construct in the composition includes complementary dimerization selectivity modules that promote dimerization between the first Fc domain monomer and the fourth Fc domain monomer; each of the second and seventh Fc domain monomers in the Fc construct in the composition includes complementary dimerization selectivity modules that promote dimerization between the second Fc domain monomer and the seventh Fc domain monomer; each of the third and eighth Fc domain monomers in the Fc construct in the composition includes complementary dimerization selectivity modules that promote dimerization between the third Fc domain monomer and the eighth Fc domain monomer; each of the fifth and ninth Fc domain monomers in the Fc construct in the composition includes complementary dimerization selectivity modules that promote dimerization between the fifth Fc domain monomer and the ninth Fc domain monomer; and each of the sixth and tenth Fc domain monomers in the Fc construct in the composition includes complementary dimerization selectivity modules that promote dimerization between the sixth Fc domain monomer and the tenth Fc domain monomer.

In some embodiments of this aspect, the complementary dimerization selectivity module of the first Fc domain monomer includes a negatively-charged amino acid substitution, the complementary dimerization selectivity module of the fourth Fc domain monomer includes a positively-charged amino acid substitution, the complementary dimerization selectivity module of each of the second, third, fifth, and sixth Fc domain monomers includes an engineered protuberance, and complementary dimerization selectivity module of each of the seventh, eighth, ninth, and tenth Fc domain monomers includes an engineered cavity.

In some embodiments of the composition including a substantially homogenous population of an Fc construct having five Fc domains described herein, the first polypeptide and the second polypeptide have the same amino acid sequence, and the third, fourth, fifth, and sixth polypeptides have the same amino acid sequence.

In another aspect, the disclosure features a composition including a substantially homogenous population of an Fc construct including: a) a first polypeptide having the formula A-L1-B-L2-C; wherein i) A includes a first Fc domain monomer; ii) L1 is a linker; iii) B includes a second Fc domain monomer; iv) L2 is a glycine spacer; v) C includes a third Fc domain monomer; and b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a glycine spacer; v) C' includes a sixth Fc domain monomer; wherein the first Fc domain monomer and the second Fc domain monomer combine to form a first Fc domain, the fourth Fc domain monomer and the fifth Fc domain monomer combine to form a second Fc domain, and the third Fc domain monomer and the sixth Fc domain monomer combine to form a third Fc domain.

In some embodiments of this aspect, each of the first and second Fc domain monomers in the Fc construct in the composition includes complementary dimerization selectivity modules that promote dimerization between the first Fc domain monomer and the second Fc domain monomer; each of the fourth and fifth Fc domain monomers in the Fc construct in the composition includes complementary dimerization selectivity modules that promote dimerization between the fourth Fc domain monomer and the fifth Fc domain monomer; and each of the third and sixth Fc domain monomers in the Fc construct in the composition includes complementary dimerization selectivity modules that promote dimerization between the third Fc domain monomer and the sixth Fc domain monomer.

In some embodiments of this aspect, the complementary dimerization selectivity module of each of the first and fourth Fc domain monomers includes an engineered protuberance, the complementary dimerization selectivity module of each of the second and fifth Fc domain monomer includes an engineered cavity, the complementary dimerization selectivity module of the third Fc domain monomer includes a negatively-charged amino acid substitution, and the complementary dimerization selectivity module of the sixth Fc domain monomer includes a positively-charged amino acid substitution.

In some embodiments of this aspect, the first polypeptide and the second polypeptide have the same amino acid sequence.

In another aspect, the disclosure features a composition including a substantially homogenous population of an Fc construct including: a) a first polypeptide having the formula A-L-B; wherein i) A includes a first Fc domain monomer; ii) L is a linker; iii) B includes a second Fc domain monomer; b) a second polypeptide having the formula A'-L'-B'; wherein i) A' includes a third Fc domain monomer; ii) L' is a linker; iii) B' includes a fourth Fc domain monomer; wherein the first Fc domain monomer and the third Fc domain monomer combine to form a first Fc domain, and the second Fc domain monomer and the fourth Fc domain monomer combine to form a second Fc domain, and wherein at least one of L and L' is a glycine spacer.

In some embodiments of this aspect, each of the first and third Fc domain monomers in the Fc construct in the composition includes complementary dimerization selectivity modules that promote dimerization between the first Fc domain monomer and the third Fc domain monomer, and each of the second and fourth Fc domain monomers in the Fc construct in the composition includes complementary dimerization selectivity modules that promote dimerization between the second Fc domain monomer and the fourth Fc domain monomer.

In some embodiments of this aspect, the complementary dimerization selectivity module of each of the first and second Fc domain monomers in the Fc construct in the composition includes an engineered protuberance, and the complementary dimerization selectivity module of each of the third and fourth Fc domain monomer in the Fc construct in the composition includes an engineered cavity.

In some embodiments of this aspect, at least one of L and L' in the Fc construct in the composition includes at least 4, 8, or 12 glycines. In some embodiments, at least one of L and L' includes 4-30, 8-30, or 12-30 glycines. In some embodiments, at least one of L and L' comprises, consists of, or consists essentially of the sequence of GGGGGGGGGGGGGGGGGGGG (SEQ ID NO: 27). In some embodiments of this aspect, each of L and L' in the Fc construct in the composition includes at least 4, 8, or 12 glycines. In some embodiments, each of L and L' includes 4-30, 8-30, or 12-30 glycines. In some embodiments, each of L and L' comprises, consists of, or consists essentially of the sequence of GGGGGGGGGGGGGGGGGGGG (SEQ ID NO: 27).

In some embodiments of this aspect, one or more of A, B, A', and B' in the Fc construct in the composition consists of an Fc domain monomer. In some embodiments of this aspect, each of A, B, A', and B' consists of an Fc domain monomer.

In some embodiments of a composition including a substantially homogenous population of an Fc construct described herein, one or more of L, L', L1, L2, L1', and L2' in the Fc construct in the composition includes at least 4, 8, or 12 glycines. In some embodiments, each of L, L', L1, L2, L1', and L2' includes at least 4, 8, or 12 glycines.

In some embodiments of a composition including a substantially homogenous population of an Fc construct described herein, one or more of L, L', L1, L2, L1', and L2' in the Fc construct in the composition includes 4-30, 8-30, or 12-30 glycines. In some embodiments, each of L, L', L1, L2, L1', and L2' includes 4-30, 8-30, or 12-30 glycines.

In some embodiments of a composition including a substantially homogenous population of an Fc construct described herein, one or more of L, L', L1, L2, L1', and L2' in the Fc construct in the composition comprises, consists of, or consists essentially of the sequence of GGGGGGGGGGGGGGGGGGGG (SEQ ID NO: 27). In some embodiments, each of L, L', L1, L2, L1', and L2' comprises, consists of, or consists essentially of the sequence of

```
                                            (SEQ ID NO: 27)
GGGGGGGGGGGGGGGGGGGG.
```

In some embodiments of a composition including a substantially homogenous population of an Fc construct described herein, one or more of A, B, C, A', B', C', the second polypeptide, the third polypeptide, the fourth polypeptide, the fifth polypeptide, and the six polypeptide in the Fc construct in the composition consists of an Fc domain monomer. In some embodiments of a composition including a substantially homogenous population of an Fc construct described herein, each of A, B, C, A', B', C', the second polypeptide, the third polypeptide, the fourth polypeptide, the fifth polypeptide, and the six polypeptide consists of an Fc domain monomer.

In some embodiments of a composition including a substantially homogenous population of an Fc construct described herein, one or more of the Fc domain monomers in the Fc construct in the composition includes an IgG hinge domain, an IgG $C_H2$ antibody constant domain, and an IgG $C_H3$ antibody constant domain. In some embodiments of a composition including a substantially homogenous population of an Fc construct described herein, each of the Fc domain monomers includes an IgG hinge domain, an IgG $C_H2$ antibody constant domain, and an IgG $C_H3$ antibody constant domain.

In some embodiments of a composition including a substantially homogenous population of an Fc construct described herein, one or more of the Fc domain monomers in the Fc construct in the composition is an IgG1 Fc domain monomer. In some embodiments of a composition including a substantially homogenous population of an Fc construct described herein, each of the Fc domain monomers is an IgG1 Fc domain monomer.

In some embodiments of a composition including a substantially homogenous population of an Fc construct described herein, the N-terminal Asp in one or more of the polypeptides in the Fc construct in the composition is mutated to Gln. In some embodiments of a composition including a substantially homogenous population of an Fc construct described herein, the N-terminal Asp in each of the polypeptides in the Fc construct in the composition is mutated to Gln.

In some embodiments of a composition including a substantially homogenous population of an Fc construct described herein, one or more of the polypeptides in the Fc construct in the composition lacks a C-terminal lysine. In some embodiments of a composition including a substantially homogenous population of an Fc construct described herein, each of the polypeptides in the Fc construct in the composition lacks a C-terminal lysine.

In another aspect, the disclosure features a composition including a substantially homogenous population of an Fc construct including: a) a first polypeptide having the formula A-L-B; wherein i) A includes a first Fc domain monomer; ii) L is a linker; and iii) B includes a second Fc domain monomer; b) a second polypeptide having the formula A'-L'-B'; wherein i) A' includes a third Fc domain monomer; ii) L' is a linker; and iii) B' includes a fourth Fc domain monomer; c) a third polypeptide that includes a fifth Fc domain monomer; and d) a fourth polypeptide that includes a sixth Fc domain monomer; wherein B and B' combine to form a first Fc domain, A and the fifth Fc domain monomer combine to form a second Fc domain, and A' and the sixth Fc domain monomer combine to form a third Fc domain, and wherein each of the first, second, third, and fourth polypeptides lacks a C-terminal lysine.

In another aspect, the disclosure features a host cell that expresses two polynucleotides both lacking the codon of C-terminal lysine, wherein the first polynucleotide encodes each of the first and second polypeptides of the previous aspect of the disclosure and the second polynucleotide encodes each of the third and fourth polypeptides of the previous aspect of the disclosure.

In another aspect, the disclosure features a composition including a substantially homogenous population of an Fc construct including: a) a first polypeptide having the formula A-L-B; wherein i) A includes a first Fc domain monomer; ii) L is a linker; and iii) B includes a second Fc domain monomer; b) a second polypeptide including a third Fc domain monomer; and c) a third polypeptide including a fourth Fc domain monomer; wherein the first Fc domain monomer and the third Fc domain monomer combine to form a first Fc domain and the second Fc domain monomer and the fourth Fc domain monomer combine to form a second Fc domain, and wherein each of the first, second, and third polypeptides lacks a C-terminal lysine.

In another aspect, the disclosure features a host cell that expresses two polynucleotides both lacking the codon of C-terminal lysine, wherein the first polynucleotide encodes the first polypeptide of the previous aspect of the disclosure and the second polynucleotide encodes each of the second and third polypeptides of the previous aspect of the disclosure.

In another aspect, the disclosure features a composition including a substantially homogenous population of an Fc construct including: a) a first polypeptide having the formula A-L1-B-L2-C; wherein i) A includes a first Fc domain monomer; ii) L1 is a linker; iii) B includes a second Fc domain monomer; iv) L2 is a linker; and v) C includes a third Fc domain monomer; b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein A and the seventh Fc domain monomer combine to form a first Fc domain, B and B' combine to form a second Fc domain, C and the eighth Fc domain monomer combine to form a third Fc domain, A' and the ninth Fc domain monomer combine to form a fourth Fc domain, and C' and the tenth Fc domain monomer combine to form a fifth Fc domain, and wherein each of the first, second, third, fourth, fifth, and sixth polypeptides lacks a C-terminal lysine.

In another aspect, the disclosure features a composition including a substantially homogenous population of an Fc construct including: a) a first polypeptide having the formula A-L1-B-L2-C; wherein i) A includes a first Fc domain monomer; ii) L1 is a linker; iii) B includes a second Fc domain monomer; iv) L2 is a linker; and v) C includes a third Fc domain monomer; b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein C and C' combine to form a first Fc domain, B and the seventh Fc domain monomer combine to form a second Fc domain, A and the eighth Fc domain monomer combine to form a third Fc domain, B' and the ninth Fc domain monomer combine to form a fourth Fc domain, and A' and the tenth Fc domain monomer combine to form a fifth Fc domain, wherein each of the first, second, third, fourth, fifth, and sixth polypeptides lacks a C-terminal lysine.

In another aspect, the disclosure features a composition including a substantially homogenous population of an Fc construct including: a) a first polypeptide having the formula A-L1-B-L2-C; wherein i) A includes a first Fc domain monomer; ii) L1 is a linker; iii) B includes a second Fc domain monomer; iv) L2 is a linker; and v) C includes a third Fc domain monomer; b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein A and A' combine to form a first Fc domain, B and the seventh Fc domain monomer combine to form a second Fc domain, C and the eighth Fc domain monomer combine to form a third Fc domain, B' and the ninth Fc domain monomer combine to form a fourth Fc domain, and C' and the tenth Fc domain monomer combine to form a fifth Fc domain, wherein each of the first, second, third, fourth, fifth, and sixth polypeptides lacks a C-terminal lysine.

In another aspect, the disclosure features a host cell that expresses two polynucleotides both lacking the codon of C-terminal lysine, wherein the first polynucleotide encodes each of the first and second polypeptides of any one of the previous three aspects of the disclosure and the second polynucleotide encodes each of the third, fourth, fifth, and sixth polypeptides of any one of the previous three aspects of the disclosure.

In another aspect, the disclosure features a composition including a substantially homogenous population of an Fc construct including: a) a first polypeptide having the formula A-L1-B-L2-C; wherein i) A includes a first Fc domain monomer; ii) L1 is a linker; iii) B includes a second Fc domain monomer; iv) L2 is a linker; v) C includes a third Fc domain monomer; and b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; v) C' includes a sixth Fc domain monomer; wherein the first Fc domain monomer and the second Fc domain monomer combine to form a first Fc domain, the fourth Fc domain monomer and the fifth Fc domain monomer combine to form a second Fc domain, and the third Fc domain monomer and the sixth Fc domain monomer combine to form a third Fc domain, wherein each of the first and second polypeptides lacks a C-terminal lysine.

In another aspect, the disclosure features a composition including a substantially homogenous population of an Fc construct including: a) a first polypeptide having the formula A-L-B; wherein i) A includes a first Fc domain monomer; ii) L is a linker; iii) B includes a second Fc domain monomer; b) a second polypeptide having the formula A'-L'-B'; wherein i) A' includes a third Fc domain monomer; ii) L' is a linker; iii) B' includes a fourth Fc domain monomer; wherein the first Fc domain monomer and the third Fc domain monomer combine to form a first Fc domain, and the second Fc domain monomer and the fourth Fc domain monomer combine to form a second Fc domain, and wherein each of the first and second polypeptides lacks a C-terminal lysine.

In another aspect, the disclosure features a host cell that expresses a polynucleotide lacking the codon of C-terminal lysine, wherein the polynucleotide encodes each of the first and second polypeptides of any of the previous two aspects of the disclosure.

In another aspect, the disclosure features a method of preparing an Fc construct described herein. The method includes: a) providing a host cell including polynucleotides encoding the polypeptides of the disclosure; b) expressing the polypeptides in the host cell under conditions that allow for the formation of the Fc construct; and c) recovering the Fc construct.

In another aspect, the disclosure features a host cell that expresses an Fc construct described herein. The host cell includes polynucleotides encoding the polypeptides of the disclosure, wherein the polynucleotides are expressed in the host cell.

In another aspect, the disclosure features a pharmaceutical composition including a substantially homogenous population of an Fc construct described herein (e.g., an Fc construct having three Fc domains) or a composition including a substantially homogenous population of an Fc construct described herein (e.g., a composition including a substantially homogenous population of an Fc construct having three Fc domains) and one or more pharmaceutically acceptable carriers or excipients. Such pharmaceutical compositions can be produced without substantial aggregation or unwanted multimerization of Fc constructs.

In another aspect, the disclosure features a method of reducing immune cell activation of the immune response in a subject, including administering to the subject an Fc construct described herein (e.g., an Fc construct having three Fc domains) or a composition including a substantially homogenous population of an Fc construct described herein (e.g., a composition including a substantially homogenous population of an Fc construct having three Fc domains). In some embodiments, the subject has an autoimmune disease.

In another aspect, the disclosure features a method of treating inflammation or an inflammatory disease in a subject, including administering to the subject an Fc construct described herein (e.g., an Fc construct having three Fc domains) or a composition including a substantially homogenous population of an Fc construct described herein (e.g., a composition including a substantially homogenous population of an Fc construct having three Fc domains).

In another aspect, the disclosure features a method of promoting clearance of autoantibodies and/or suppressing antigen presentation in a subject, including administering to the subject an Fc construct described herein (e.g., an Fc construct having three Fc domains) or a composition including a substantially homogenous population of an Fc construct described herein (e.g., a composition including a substantially homogenous population of an Fc construct having three Fc domains).

In some embodiments, exemplary diseases that may be treated by administering an Fc construct described herein (e.g., an Fc construct having three Fc domains) include: rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; clearance of anti-allo in transplant, anti-self in GVHD, anti-replacement, IgG therapeutics, IgG paraproteins; dermatomyositis; Goodpasture's Syndrome; organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease; idiopathic thrombocytopenia purpura; Myasthenia Gravis, neuromyelitis optica; pemphigus and other autoimmune blistering disorders; Sjogren's Syndrome; autoimmune cytopenias and other disorders mediated through antibody-dependent phagocytosis; other FcR-dependent inflammatory syndromes, e.g., synovitis, dermatomyositis, systemic vasculitis, glomerulitis and vasculitis.

In another aspect, the disclosure features a cell culture medium including a substantially homogenous population of an Fc construct including: a) a first polypeptide having the formula A-L-B; wherein i) A includes a first Fc domain monomer; ii) L is a glycine spacer; and iii) B includes a second Fc domain monomer; b) a second polypeptide having the formula A'-L'-B'; wherein i) A' includes a third Fc domain monomer; ii) L' is a glycine spacer; and iii) B' includes a fourth Fc domain monomer; c) a third polypeptide that includes a fifth Fc domain monomer; and d) a fourth polypeptide that includes a sixth Fc domain monomer; wherein each of the first and second polypeptides has at least 95% sequence identity to the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPC RDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGDKTHTCPPCPAPELLG GPSVFLFPPKPKDTLMISRTPEVTCVVVDVSHEDPEVKFNVVYVDGVEVHNAKTKPREEQYNSTYRVV SVLTVLHQDWLNGKEYKCKVSNKALPAPIEKTISKAKGQPREPQVYTLPPSRDELTKNQVSLTCLVKG FYPSDIAVEWESNGQPENNYKTTPPVLKSDGSFFLYSDLTVDKSRWQQGNVFS CSVMHEALHNHYT QKSLSLSPG (SEQ ID NO: 49), each of the third and fourth polypeptides has at least 95% sequence identity to the sequence of DKTHTCPPCPAPELLGGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVCTLPPS RDELTKNQVSLSCAVDGFYPSDIAVEWESNGQPENNYKTTPPVLDSDGSFFLVSKLTVDKSRWQQG NVFSCSVMHEALHNHYTQKSLSLSPG (SEQ ID NO: 48), B and B' combine to form a first Fc domain, A and the fifth Fc domain monomer combine to form a second Fc domain, and A' and the sixth Fc domain monomer combine to form a third Fc domain, each of B and B' includes the mutations D399K and K409D, each of A and A' includes the mutations S354C, T366W, and E357K, and each of the fifth and sixth Fc domain monomers includes the mutations Y349C, T366S, L368A, Y407V, and K370D, each of L and L' includes 12-30 glycines, and each of the first, second, third, and fourth polypeptides lack a C-terminal lysine.

In another aspect, the disclosure features a method of preparing a cell culture medium including a substantially homogenous population of an Fc construct described herein (e.g., the Fc construct of the first aspect of the disclosure. The method includes: a) providing host cells in a cell culture medium, wherein the cells include polynucleotides encoding each of the first, second, third, and fourth polypeptides of an Fc construct (e.g., the Fc construct of the first aspect of the disclosure); b) expressing the polypeptides in the host cells under conditions that allow for the formation of the Fc construct and secretion into the cell culture medium; and c) collecting the cell culture medium.

Additionally, the disclosure also features other cell culture medium including a substantially homogenous population of other Fc constructs of the disclosure and methods of preparing such cell culture medium.

In some embodiments, the Fc constructs described herein do not include an antigen-recognition region, e.g., a variable domain or a complementarity determining region (CDR). In some embodiments, the Fc construct (or an Fc domain within an Fc construct) is formed entirely or in part by association of Fc domain monomers that are present in different polypeptides. In some embodiments, the Fc constructs described herein include an antigen-recognition region, e.g., a variable domain or a CDR. In certain embodiments, the Fc construct does not include an additional domain (e.g., an IgM tailpiece or an IgA tailpiece) that promotes association of two polypeptides. In other embodiments, covalent linkages are present in the Fc construct only between two Fc domain monomers that join to form an Fc domain. In other embodiments, the Fc construct does not include covalent linkages between Fc domains. In still other embodiments, the Fc construct provides for sufficient structural flexibility such that all or substantially all of the Fc domains in the Fc construct are capable of simultaneously interacting with an Fc receptor on a cell surface. In one embodiment, the domain monomers are different in primary sequence from wild-type or from each other in that they have dimerization selectivity modules.

The Fc domain monomers of an Fc domain of the construct can have the same primary amino acid sequence. For example, both Fc domain monomers of an Fc domain may have the same dimerization selectivity module, e.g., both Fc domain monomers of an Fc domain may have identical reverse charge mutations in at least two positions within the ring of charged residues at the interface between $C_H3$ domains.

In any of the Fc constructs described herein, the Fc domain monomers of an Fc domain of a construct can have different sequences, e.g., sequences that differ by no more than 20 amino acids (e.g., no more than 15, 10 amino acids), e.g., no more than 20, 15, 10, 8, 7, 6, 5, 4, 3 or 2 amino acids, between two Fc domain monomers (i.e., between the Fc domain monomer and another monomer of the Fc construct). For example, Fc domain monomer sequences of a construct described herein may be different because complementary dimerization selectivity modules of any of the Fc constructs can include an engineered cavity in the $C_H3$ antibody constant domain of one of the domain monomers and an engineered protuberance in the $C_H3$ antibody constant domain of the other of the Fc domain monomers, wherein the engineered cavity and the engineered protuberance are positioned to form a protuberance-into-cavity pair of Fc domain monomers. Exemplary engineered cavities and protuberances are shown in Table 1. In other embodiments, the complementary dimerization selectivity modules include an engineered (substituted) negatively-charged amino acid in the $C_H3$ antibody constant domain of one of the domain monomers and an engineered (substituted) positively-charged amino acid in the $C_H3$ antibody constant domain of the other of the Fc domain monomers, wherein the negatively-charged amino acid and the positively-charged amino acid are positioned to promote formation of an Fc domain between complementary domain monomers. Exemplary complementary amino acid changes are shown in Tables 2A-2C.

The disclosure also features a pharmaceutical composition that includes a substantially homogenous population of any Fc construct described herein. In one embodiment, a sterile syringe or vial qualified for pharmaceutical use contains a pharmaceutical composition wherein the only or primary active ingredient is a substantially homogenous population of any one of the Fc constructs described herein. The pharmaceutical composition may include one or more inactive ingredients, e.g., selected from salts, detergents, surfactants, bulking agents, polymers, preservatives, and other pharmaceutical excipients.

In another aspect, this disclosure provides for a pharmaceutical composition that includes any of the Fc constructs described herein.

In some embodiments, the Fc construct is formed at least in part by association of Fc domain monomers that are present in different polypeptides. In certain embodiments, the Fc construct is formed by association of Fc domain monomers that are present in different polypeptides. In these embodiments, the Fc construct does not include an additional domain that promotes association of two polypeptides (e.g., an IgM tailpiece or an IgA tailpiece). In other embodiments, covalent linkages (e.g., disulfide bridges) are present only between two Fc domain monomers that join to form an Fc domain. In other embodiments, the Fc construct does not include covalent linkages (e.g., disulfide bridges) between Fc domains. In still other embodiments, the Fc construct provides for sufficient structural flexibility such that all or substantially all of the Fc domains in the Fc construct are capable of simultaneously interacting with an Fc receptor on a cell surface. In certain examples of any of these embodiments, the Fc construct includes at least two Fc domains joined through a linker (e.g., a flexible amino acid spacer).

In another aspect, the disclosure features compositions and methods for promoting selective dimerization of Fc domain monomers. The disclosure includes an Fc domain wherein the two Fc domain monomers of the Fc domain include identical mutations in at least two positions within the ring of charged residues at the interface between $C_H3$ antibody constant domains. The disclosure also includes a method of making such an Fc domain, including introducing complementary dimerization selectivity modules having identical mutations in two Fc domain monomer sequences in at least two positions within the ring of charged residues at the interface between $C_H3$ antibody constant domains. The interface between $C_H3$ antibody constant domains consists of a hydrophobic patch surrounded by a ring of charged residues. When one $C_H3$ antibody constant domain comes together with another, these charged residues pair with residues of the opposite charge. By reversing the charge of both members of two or more complementary pairs of residues, mutated Fc domain monomers remain complementary to Fc domain monomers of the same mutated sequence, but have a lower complementarity to Fc domain monomers without those mutations. In this embodiment, the identical dimerization selectivity modules promotes homodimerization. Such Fc domains include Fc domain monomers containing the double mutants K409D/D399K, K392D/D399K, E357K/K370E, D356K/K439D, K409E/D399K, K392E/D399K, E357K/K370D, or D356K/K439E. In another embodiment, an Fc domain includes Fc domain monomers including quadruple mutants combining any pair of the double mutants, e.g., K409D/D399K/E357K/K370E.

In another embodiment, in addition to the identical dimerization selectivity modules, the Fc domain monomers of the Fc domain include complementary dimerization selectivity modules having non-identical mutations that promote specific association (e.g., engineered cavity and protuberance). As a result, the two Fc domain monomers include two dimerization selectivity modules and remain complementary to each other, but have a decreased complementarity to other Fc domain monomers. This embodiment promotes heterodimerization between a cavity-containing Fc domain and a protuberance-containing Fc domain monomer. In one example, the complementary dimerization selectivity modules having non-identical mutations in charged pair residues of both Fc domain monomers are combined with a protuberance on one Fc domain monomer and a cavity on the other Fc domain monomer.

In any of the Fc constructs described herein, it is understood that the order of the Fc domain monomers is interchangeable. For example, in a polypeptide having the formula A-L-B, the carboxy terminus of A can be joined to the amino terminus of L, which in turn is joined at its carboxy terminus to the amino terminus of B. Alternatively, the carboxy terminus of B can be joined to the amino terminus of L, which in turn is joined at its carboxy terminus to the amino terminus of C. Both of these configurations are encompassed by the formula A-L-B.

Definitions

As used herein, the term "Fc domain monomer" refers to a polypeptide chain that includes at least a hinge domain and second and third antibody constant domains ($C_H2$ and $C_H3$) or functional fragments thereof (e.g., fragments that that capable of (i) dimerizing with another Fc domain monomer to form an Fc domain, and (ii) binding to an Fc receptor). The Fc domain monomer can be any immunoglobulin antibody isotype, including IgG, IgE, IgM, IgA, or IgD (e.g., IgG). Additionally, the Fc domain monomer can be an IgG subtype (e.g., IgG1, IgG2a, IgG2b, IgG3, or IgG4) (e.g., IgG1). An Fc domain monomer does not include any portion of an immunoglobulin that is capable of acting as an antigen-recognition region, e.g., a variable domain or a complementarity determining region (CDR). Fc domain monomers can contain as many as ten changes from a wild-type Fc domain monomer sequence (e.g., 1-10, 1-8, 1-6, 1-4 amino acid substitutions, additions, or deletions) that alter the interaction between an Fc domain and an Fc receptor. Examples of suitable changes are known in the art.

As used herein, the term "Fc domain" refers to a dimer of two Fc domain monomers that is capable of binding an Fc receptor. In the wild-type Fc domain, the two Fc domain monomers dimerize by the interaction between the two $C_H3$ antibody constant domains, as well as one or more disulfide bonds that form between the hinge domains of the two dimerizing Fc domain monomers.

In the present disclosure, the term "Fc construct" refers to associated polypeptide chains forming Fc domains as described herein (e.g., an Fc construct having three Fc domains). Fc constructs described herein can include Fc domain monomers that have the same or different sequences. For example, an Fc construct can have three Fc domains, two of which includes IgG1 or IgG1-derived Fc domain monomers, and a third which includes IgG2 or IgG2-derived Fc domain monomers. In another example, an Fc construct can have three Fc domains, two of which comprises a "protuberance-into-cavity pair" and a third which does not comprise a "protuberance-into-cavity pair." In the present disclosure, an Fc domain does not include a variable region of an antibody, e.g., $V_H$, $V_L$, CDR, or HVR. An Fc domain forms the minimum structure that binds to an Fc receptor, e.g., FcγRI, FcγRIIa, FcγRIIb, FcγRIIIa, FcγRIIIb, FcγRIV. In some embodiments, the Fc constructs described herein do not include an antigen-recognition region, e.g., a variable domain or a complementarity determining region (CDR). In some embodiments, the Fc constructs described herein include an antigen-recognition region, e.g., a variable domain or a CDR.

As used herein, the term "antibody constant domain" refers to a polypeptide that corresponds to a constant region domain of an antibody (e.g., a $C_L$ antibody constant domain, a $C_H1$ antibody constant domain, a $C_H2$ antibody constant domain, or a $C_H3$ antibody constant domain).

As used herein, the term "promote" means to encourage and to favor, e.g., to favor the formation of an Fc domain from two Fc domain monomers which have higher binding affinity for each other than for other, distinct Fc domain monomers. As is described herein, two Fc domain monomers that combine to form an Fc domain can have compatible amino acid modifications (e.g., engineered protuberances and engineered cavities) at the interface of their respective $C_H3$ antibody constant domains. The compatible amino acid modifications promote or favor the selective interaction of such Fc domain monomers with each other relative to with other Fc domain monomers which lack such amino acid modifications or with incompatible amino acid modifications. This occurs because, due to the amino acid modifications at the interface of the two interacting $C_H3$ antibody constant domains, the Fc domain monomers to have a higher affinity toward each other than to other Fc domain monomers lacking amino acid modifications.

As used herein, the term "a dimerization selectivity module" refers to a sequence of the Fc domain monomer that facilitates the favored pairing between two Fc domain monomers. "Complementary" dimerization selectivity modules are dimerization selectivity modules that promote or favor the selective interaction of two Fc domain monomers with each other. Complementary dimerization selectivity modules can have the same or different sequences. Exemplary complementary dimerization selectivity modules are described herein.

As used herein, the term "engineered cavity" refers to the substitution of at least one of the original amino acid residues in the $C_H3$ antibody constant domain with a different amino acid residue having a smaller side chain volume than the original amino acid residue, thus creating a three dimensional cavity in the $C_H3$ antibody constant domain. The term "original amino acid residue" refers to a naturally occurring amino acid residue encoded by the genetic code of a wild-type $C_H3$ antibody constant domain.

As used herein, the term "engineered protuberance" refers to the substitution of at least one of the original amino acid residues in the $C_H3$ antibody constant domain with a different amino acid residue having a larger side chain volume than the original amino acid residue, thus creating a three dimensional protuberance in the $C_H3$ antibody constant domain. The term "original amino acid residues" refers to naturally occurring amino acid residues encoded by the genetic code of a wild-type $C_H3$ antibody constant domain.

As used herein, the term "protuberance-into-cavity pair" describes an Fc domain including two Fc domain monomers, wherein the first Fc domain monomer includes an engineered cavity in its $C_H3$ antibody constant domain, while the second Fc domain monomer includes an engineered protuberance in its $C_H3$ antibody constant domain. In a protuberance-into-cavity pair, the engineered protuberance in the $C_H3$ antibody constant domain of the first Fc domain monomer is positioned such that it interacts with the engineered cavity of the $C_H3$ antibody constant domain of the second Fc domain monomer without significantly perturbing the normal association of the dimer at the inter-$C_H3$ antibody constant domain interface.

As used herein, the term "heterodimer Fc domain" refers to an Fc domain that is formed by the heterodimerization of two Fc domain monomers, wherein the two Fc domain monomers contain different reverse charge mutations (see, e.g., mutations in Table 2A) that promote the favorable formation of these two Fc domain monomers. As shown in FIGS. 1 and 2, in an Fc construct having three Fc domains—one carboxyl terminal "stem" Fc domain and two amino terminal "branch" Fc domains—each of the amino terminal "branch" Fc domains may be a heterodimeric Fc domain (also called a "branch heterodimeric Fc domain") (e.g., a heterodimeric Fc domain formed by Fc domain monomers 106 and 114 or Fc domain monomers 112 and 116 in FIG. 1; a heterodimeric Fc domain formed by Fc domain monomers 206 and 214 or Fc domain monomers 212 and 216 in FIG. 2).

As used herein, the term "homodimeric Fc domain" refers to an Fc domain that is formed by the homodimerization of two Fc domain monomers, wherein the two Fc domain monomers contain the same reverse charge mutations (see, e.g., mutations in Tables 2B and 2C). As shown in FIGS. 1 and 2, in an Fc construct having three Fc domains—one carboxyl terminal "stem" Fc domain and two amino terminal "branch" Fc domains—the carboxy terminal "stem" Fc domain may be a homodimeric Fc domain (also called a "stem homodimeric Fc domain") (e.g., a homodimeric Fc domain formed by Fc domain monomers 104 and 110 in FIG. 1; a homodimeric Fc domain formed by Fc domain monomers 204 and 210 in FIG. 2).

As used herein, the term "heterodimerizing selectivity module" refers to engineered protuberances, engineered cavities, and certain reverse charge amino acid substitutions that can be made in the $C_H3$ antibody constant domains of Fc domain monomers in order to promote favorable heterodimerization of two Fc domain monomers that have compatible heterodimerizing selectivity modules. Fc domain monomers containing heterodimerizing selectivity modules may combine to form a heterodimeric Fc domain. Examples of heterodimerizing selectivity modules are shown in Table 1 and 2A.

As used herein, the term "homodimerizing selectivity module" refers to reverse charge mutations in an Fc domain monomer in at least two positions within the ring of charged residues at the interface between $C_H3$ domains that promote homodimerization of the Fc domain monomer to form a homodimeric Fc domain. Examples of homodimerizing selectivity modules are shown in Tables 2A and 2B.

As used herein, the term "joined" is used to describe the combination or attachment of two or more elements, components, or protein domains, e.g., polypeptides, by means including chemical conjugation, recombinant means, and chemical bonds, e.g., disulfide bonds and amide bonds. For example, two single polypeptides can be joined to form one contiguous protein structure through chemical conjugation, a chemical bond, a peptide linker, or any other means of covalent linkage. In some embodiments, a first Fc domain monomer is joined to a second Fc domain monomer by way of a peptide linker, wherein the N-terminus of the peptide linker is joined to the C-terminus of the first Fc domain monomer through a chemical bond, e.g., a peptide bond, and the C-terminus of the peptide linker is joined to the N-terminus of the second Fc domain monomer through a chemical bond, e.g., a peptide bond. In other embodiments, the N-terminus of an albumin-binding peptide is joined to the C-terminus of the $C_H3$ antibody constant domain of an Fc domain monomer by way of a linker in the same fashion as mentioned above.

As used herein, the term "associated" is used to describe the interaction, e.g., hydrogen bonding, hydrophobic interaction, or ionic interaction, between polypeptides (or sequences within one single polypeptide) such that the polypeptides (or sequences within one single polypeptide) are positioned to form an Fc construct described herein (e.g., an Fc construct having three Fc domains). For example, in some embodiments, four polypeptides, e.g., two polypeptides each including two Fc domain monomers and two polypeptides each including one Fc domain monomer, associate to form an Fc construct that has three Fc domains (e.g., as depicted in FIGS. 1 and 2). The four polypeptides can associate through their respective Fc domain monomers. The association between polypeptides does not include covalent interactions.

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 3-200 amino acid, 3-150 amino acid, 3-100 amino acid, 3-60 amino acid, 3-50 amino acid, 3-40 amino acid, 3-30 amino acid, 3-20 amino acid, 3-10 amino acid, 3-8 amino acid, 3-5 amino acid, 4-30 amino acid, 5-30 amino acid, 6-30 amino acid, 8-30 amino acid, 10-20 amino acid, 10-30 amino acid, 12-30 amino acid, 14-30 amino acid, 20-30 amino acid, 15-25 amino acid, 15-30 amino acid, 18-22 amino acid, and 20-30 amino acid sequence) occurring between two polypeptides or polypeptide domains to provide space and/or flexibility between the two polypeptides or polypeptide domains. An amino acid spacer is part of the primary sequence of a polypeptide (e.g., joined to the spaced polypeptides or polypeptide domains via the polypeptide backbone). The formation of disulfide bonds, e.g., between two hinge regions or two Fc domain monomers that form an Fc domain, is not considered a linker.

As used herein, the term "glycine spacer" refers to a linker containing only glycines that joins two Fc domain monomers in tandem series. A glycine spacer may contain at least 4, 8, 10, 12, 14, 16, 18, or 20 glycines (e.g., 4-30, 8-30, 12-30, 12-50, 12-100, or 12-200 glycines; e.g., 12-30, 4, 5, 6, 7, 8, 9, 10, 11, 12, 13, 14, 15, 16, 17, 18, 19, 20, 21, 22, 23, 24, 25, 26, 27, 28, 29, or 30 glycines). In some embodiments, a glycine spacer comprises, consists of, or consists essentially of the sequence of GGGGGGGGGGGGGGGGGGGGG (SEQ ID NO: 27).

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments of the present disclosure, an albumin-binding peptide is fused to the C-terminus of an Fc domain monomer to increase the serum half-life of the Fc construct. An albumin-binding peptide can be fused, either directly or through a linker, to the N- or C-terminus of an Fc domain monomer.

As used herein, the term "purification peptide" refers to a peptide of any length that can be used for purification, isolation, or identification of a polypeptide. A purification peptide may be joined to a polypeptide to aid in purifying the polypeptide and/or isolating the polypeptide from, e.g., a cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be joined to an Fc construct are described in further detail herein.

As used herein, the term "multimer" refers to a molecule including at least two associated Fc constructs described herein.

As used herein, the term "antigen-recognition region" refers to the portions of the light and heavy chains of an antibody that are responsible for the recognition and binding of an antibody to an antigen. The antigen-recognition region includes the variable domains of the light and heavy chains (Fab), which include the complementary determining regions (CDRs, e.g., CDR L1, CDR L2, CDR L3, CDR H1, CDR H2, and CDR H3) and framework regions (FRs).

As used herein, the phrase "immune cell activation of the immune response" refers to an immune response that is induced or activated by the binding of an immune complex or an Fc construct to an Fcγ receptor (FcγR) (e.g., an activating FcγR, e.g., FcγRI, FcγRIIa, FcγRIIc, FcγRIIIa, or FcγRIIIb) on a cell (e.g., an immune cell (e.g., a monocyte)). An immune complex is an antigen-antibody complex formed from the binding of an antibody to an antigen. An immune complex often has multiple Fc domains, which aggregate FcγRs and inhibit or activate cellular processes that play critical roles in inflammation, infection, and other diseases. In some embodiments, Fc constructs of the disclosure are able to bind to FcγRs and induce activating FcγR (e.g., FcγRI, FcγRIIa, FcγRIIc, FcγRIIIa, or FcγRIIIb) signaling on immune cells (e.g., a monocyte). Measurement of certain downstream signaling events, such as kinase phosphorylation (e.g., Syk phosphorylation) and calcium influx in the FcγR-expressing cell may be used to detect immune cell activation of an immune response caused by the binding of an immune complex or an Fc construct. For example, immune cell activation of the immune response is induced if the level of kinase phosphorylation (e.g., Syk phosphorylation) or the level of calcium influx of the cell is at least 5 fold, e.g., 5-100 fold (e.g., 5-100, 10-95, 15-90, 20-85, 25-80, 30-75, 35-70, 40-65, 45-60, or 50-55 fold; e.g., 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, or 100-fold) higher than the level of kinase phosphorylation (e.g., Syk phosphorylation) or calcium influx of the cell without any activation by the immune complex or the Fc construct.

As used herein, the term "phagocytosis" refers a form of endocytosis, in which a cell, often a phagocyte (e.g., a monocyte), engulfs another cell, a particle, or a pathogen (e.g., a microbe or a parasite) to form a phagosome. In the immune system, phagocytosis is a major mechanism used to remove diseased cells (e.g., a cancer cell, an infected cell, or a dead cell), pathogens, and cell debris. A cell that is targeted to be phagocytosed by another cell (e.g., a phagocyte (e.g., a monocyte)) is referred to as a target cell. For example, an immune cell (e.g., a monocyte) activated by the binding of an Fc construct of the disclosure to the FcγRs (e.g., FcγRI, FcγRIIa, FcγRIIc, FcγRIIIa, or FcγRIIIb) on the immune cell may phagocytose a target cell, which may be a cancer cell or an infected cell in a subject.

As used herein, "increase" or "increasing" phagocytosis of a target cell refers to the increase in phagocytosis induced by the binding of an Fc construct of the disclosure to FcγRs (e.g., FcγRI, FcγRIIa, FcγRIIc, FcγRIIIa, or FcγRIIIb) on an immune cell (e.g., a monocyte) relative the level of phagocytosis that occur without Fc construct induction. For example, phagocytosis of a target cell is increased if the level of phagocytosis is at least 10%, e.g., 10-100% (e.g., 10-100%, 15-95%, 20-90%, 25-85%, 30-80%, 35-75%, 40-70%, 45-65%, or 50-60%; e.g., 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) higher than the level of phagocytosis that occur without Fc construct induction.

As used herein, the term "treating cancer" refers to a therapeutic treatment of cancer in a subject. A therapeutic treatment slows the progression of cancer, improves the subject's outcome, and/or eliminates the cancer.

As used herein, the term "treating an infection" refers to a therapeutic treatment of an infection in a subject. A therapeutic treatment slows the progression of the infection, improves the subject's outcome, and/or eliminates the infection.

As used herein, the term "infection" refers to the invasion of a subject's cells, tissues, and/or organs by a pathogen, such as bacteria, viruses, fungi, helminths, protozoans, arthropods, and other microbes, parasites, and worms. In some embodiments, the pathogen may grow, multiply, and/or produce toxins in the subject's cells, tissues, and/or organs. In some embodiments, the subject may develop a negative reaction (i.e., an allergic reaction or an immune response) to the pathogen. Examples of infections include, but are not limited to, a bacterial infection, a viral infection, a fungal infection, a helmintic infection, and a protozoal infection.

As used herein, the term "bacterial infection" refers to an infection caused by one or more bacteria. Examples of infection-causing bacteria are well-known in the art and include, but are not limited to, bacteria in the genus *Streptococcus* (e.g., *Streptococcus pyogenes*), bacteria in the genus *Escherichia* (e.g., *Escherichia coli*), bacteria in the genus *Vibrio* (e.g., *Vibrio cholerae*), bacteria in the genus Enteritis (e.g., Enteritis *salmonella*), and bacteria in the genus *Salmonella* (e.g., *Salmonella typhi*).

As used herein, the term "viral infection" refers to an infection caused by one or more viruses. Examples of infection-causing viruses are well-known in the art and include, but are not limited to, viruses in the family Retroviridae (e.g., human immunodeficiency virus (HIV)), viruses in the family Adenoviridae (e.g., adenovirus), viruses in the family Herpesviridae (e.g., herpes simplex virus types 1 and 2), viruses in the family Papillomaviridae (e.g., human papillomavirus (HPV)), viruses in the family Poxviridae (e.g., smallpox), viruses in the family Picornaviridae (e.g., hepatitis A virus, poliovirus, rhinovirus), viruses in the family Hepadnaviridae (e.g., hepatitis B virus), viruses in the family Flaviviridae virus (e.g., hepatitus C virus, yellow fever virus, West Nile virus), viruses in the family Togaviridae (e.g., rubella virus), viruses in the family Orthomyxoviridae (e.g., influenza virus), viruses in the family Filoviridae (e.g., ebola virus, marburg virus), and viruses in the family Paramyxoviridae (e.g., measles virus, mumps virus).

As used herein, the term "fungal infection" refers to an infection caused one or more fungi. Examples of infection-causing fungi are well-known in the art and include, but are not limited to, fungi in the genus *Aspergillus* (e.g., *Aspergillus fumigatus, A. flavus, A. terreus. A. niger, A. candidus, A. clavatus, A. ochraceus*), fungi in the genus *Candida* (e.g., *Candida albicans, C. parapsilosis, C. glabrata, C. guilliermondii, C. krusei, C. lusitaniae, C. tropicalis*), fungi in the genus *Cryptococcus* (e.g., *Cryptococcus neoformans*), and fungi in the genus *Fusarium* (e.g., *Fusarium solani, F. verticillioides, F. oxysporum*).

As used herein, the term "helmintic infection" refers to an infection caused by one or more helminths. Examples of helminths include, but are not limited to, tapeworms (cestodes), roundworms (nematodes), flukes (trematodes), and monogeneans.

As used herein, the term "protozoal infection" refers to an infection caused by one or more protozoans. Examples of protozoans include, but are not limited to, protozoans in the genus *Entamoeba* (e.g., *Entamoeba histolytica*), protozoans in the genus *Plasmodium* (e.g., *Plasmodium falciparum, P. malariae*), protozoans in the genus *Giardia* (e.g., *Giardia lamblia*), and protozoans in the genus *Trypanosoma* (e.g., *Trypanosoma brucei*).

As used herein, the term "polynucleotide" refers to an oligonucleotide, or nucleotide, and fragments or portions thereof, and to DNA or RNA of genomic or synthetic origin, which may be single- or double-stranded, and represent the sense or anti-sense strand. A single polynucleotide is translated into a single polypeptide.

As used herein, the term "polypeptide" describes a single polymer in which the monomers are amino acid residues which are joined together through amide bonds. A polypeptide is intended to encompass any amino acid sequence, either naturally occurring, recombinant, or synthetically produced.

As used herein, the term "amino acid positions" refers to the position numbers of amino acids in a protein or protein domain. The amino acid positions for antibody or Fc constructs are numbered using the Kabat numbering system (Kabat et al., Sequences of Proteins of Immunological Interest, National Institutes of Health, Bethesda, Md., ed 5, 1991).

As used herein, the term "amino acid modification" or refers to an alteration of an Fc domain polypeptide sequence that, compared with a reference sequence (e.g., a wild-type, unmutated, or unmodified Fc sequence) may have an effect on the pharmacokinetics (PK) and/or pharmacodynamics (PD) properties, serum half-life, effector functions (e.g., cell lysis (e.g., antibody-dependent cell-mediated toxicity (ADCC) and/or complement dependent cytotoxicity activity (CDC)), phagocytosis (e.g., antibody dependent cellular phagocytosis (ADCP) and/or complement-dependent cellular cytotoxicity (CDCC)), immune activation, and T-cell activation), affinity for Fc receptors (e.g., Fc-gamma receptors (FcγR) (e.g., FcγRI (CD64), FcγRIIa (CD32), FcγRIIb (CD32), FcγRIIIa (CD16a), and/or FcγRIIIb (CD16b)), Fc-alpha receptors (FcαR), Fc-epsilon receptors (FcεR), and/or to the neonatal Fc receptor (FcRn)), affinity for proteins involved in the compliment cascade (e.g., C1q), post-translational modifications (e.g., glycosylation, sialylation), aggregation properties (e.g., the ability to form dimers (e.g., homo- and/or heterodimers) and/or multimers), and the biophysical properties (e.g., alters the interaction between $C_H1$ and $C_L$, alters stability, and/or alters sensitivity to temperature and/or pH) of an Fc construct, and may promote improved efficacy of treatment of immunological and inflammatory diseases, cancers, and infections. An amino acid modification includes amino acid substitutions, deletions, and/or insertions. In some embodiments, an amino acid modification is the modification of a single amino acid. In other embodiment, the amino acid modification is the modification of multiple (e.g., more than one) amino acids. The amino acid modification may comprise a combination of amino acid substitutions, deletions, and/or insertions. Included in the description of amino acid modifications, are genetic (i.e., DNA and RNA) alterations such as point mutations (e.g., the exchange of a single nucleotide for another), insertions and deletions (e.g., the addition and/or removal of one or more nucleotides) of the nucleotide sequence that codes for an Fc polypeptide.

In certain embodiments, at least one (e.g., one, two, or three) Fc domain within an Fc construct includes an amino acid modification. In some instances the at least one Fc domain includes one or more (e.g., two, three, four, five, six, seven, eight, nine, ten, or twenty or more) amino acid modifications. In some instances, the at least one Fc domain includes no more than sixteen amino acid modifications (e.g., no more than one, two, three, four, five, six, seven, eight, nine, ten, eleven, twelve, thirteen, fourteen, fifteen, or sixteen amino acid modifications). In some cases, the Fc domain monomer includes no more than ten amino acid modifications. In some cases, the Fc domain monomer includes no more than 12 amino acid modifications. In some cases, the Fc domain monomer includes no more than 14 amino acid modifications.

As used herein, the term "percent (%) identity" refers to the percentage of amino acid (or nucleic acid) residues of a candidate sequence, e.g., the sequence of an Fc domain monomer in an Fc construct described herein, that are identical to the amino acid (or nucleic acid) residues of a reference sequence, e.g., the sequence of a wild-type Fc domain monomer, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity (e.g., 50% to 100%, 60% to 100%, 70% to 100%, 80% to 100%, 90% to 100%, 92% to 100%, 95% to 100%, 97% to 100%, 99% to 100%, or 99.5% to 100% identity), across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

In some embodiments, an Fc domain monomer in an Fc construct described herein (e.g., an Fc construct having three Fc domains) may have a sequence that is at least 95% identical (e.g., at least 97%, 99%, or 99.5% identical) to the sequence of a wild-type Fc domain monomer (e.g., SEQ ID NO: 42). In some embodiments, an Fc domain monomer in an Fc construct described herein (e.g., an Fc construct having three Fc domains) may have a sequence that is at least 95% identical (e.g., at least 97%, 99%, or 99.5% identical) to the sequence of any one of SEQ ID NOs: 44, 46, 48, and 50-53. In certain embodiments, an Fc domain monomer in the Fc construct may have a sequence that is at least 95% identical (e.g., at least 97%, 99%, or 99.5% identical) to the sequence of SEQ ID NO: 48, 52, and 53.

In some embodiments, the Fc domain monomer in an Fc construct described herein (e.g., an Fc construct having multiple Fc domains) may have a sequence with up to 10 (e.g., 9, 8, 7, 6, 5, 4, 3, 2, or 1) single amino acid modifications (e.g., substitutions, e.g., conservative substitutions). In some instances, the at least one Fc domain includes no more than sixteen amino acid modifications (e.g., no more than one, two, three, four, five, six, seven, eight, nine, ten, eleven, twelve, thirteen, fourteen, fifteen, or sixteen amino acid modifications).

In some embodiments, a polypeptide having two Fc domain monomers in an Fc construct described herein (e.g., polypeptides 102 and 108 in FIG. 1; polypeptides 202 and 208 in FIG. 2) may have a sequence that is at least 95% identical (e.g., at least 97%, 99%, or 99.5% identical) to the sequence of any one of SEQ ID NOs: 43, 45, 47, and 49. In certain embodiments, a polypeptide having two Fc domain monomers in an Fc construct described herein may have a sequence that is at least 95% identical (e.g., at least 97%, 99%, or 99.5% identical) to the sequence of SEQ ID NO: 49.

In some embodiments, a spacer between two Fc domain monomers may have a sequence that is at least 75% identical (e.g., 75%, 77%, 79%, 81%, 83%, 85%, 87%, 89%, 91%, 93%, 95%, 97%, 99%, 99.5%, or 100% identical) to the sequence of any one of SEQ ID NOs: 1-36 (e.g., SEQ ID NOs: 17, 18, 26, and 27) described further herein.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express one or more polypeptides encoding desired domains which can then combine to form a desired Fc construct.

As used herein, the term "pharmaceutical composition" refers to a medicinal or pharmaceutical formulation that contains an active ingredient as well as one or more excipients and diluents to enable the active ingredient to be suitable for the method of administration. The pharmaceutical composition of the present disclosure includes pharmaceutically acceptable components that are compatible with the Fc construct. The pharmaceutical composition is typically in aqueous form for intravenous or subcutaneous administration.

As used herein, a "substantially homogenous population" of polypeptides or of an Fc construct is one in which at least 50% of the polypeptides or Fc constructs in a composition (e.g., a cell culture medium or a pharmaceutical composition) have the same number of Fc domains, as determined by non-reducing SDS gel electrophoresis or size exclusion chromatography. A substantially homogenous population (e.g., a population that is at least 85%, 90%, or 95% homogenous) of polypeptides or of an Fc construct may be obtained prior to purification, or after Protein A or Protein G purification, or after any Fab or Fc-specific affinity chromatography only. In various embodiments, at least 55%, 60%, 65%, 70%, 75%, 80%, or 85% of the polypeptides or Fc constructs in the composition have the same number of Fc domains. In other embodiments, up to 85%, 90%, 92%, or 95% of the polypeptides or Fc constructs in the composition have the same number of Fc domains.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present disclosure, the pharmaceutically acceptable carrier must provide adequate pharmaceutical stability to the Fc construct. The nature of the carrier differs with the mode of administration. For example, for oral administration, a solid carrier is preferred; for intravenous administration, an aqueous solution carrier (e.g., WFI, and/or a buffered solution) is generally used.

As used herein, "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

DETAILED DESCRIPTION OF THE INVENTION

Figure 1:
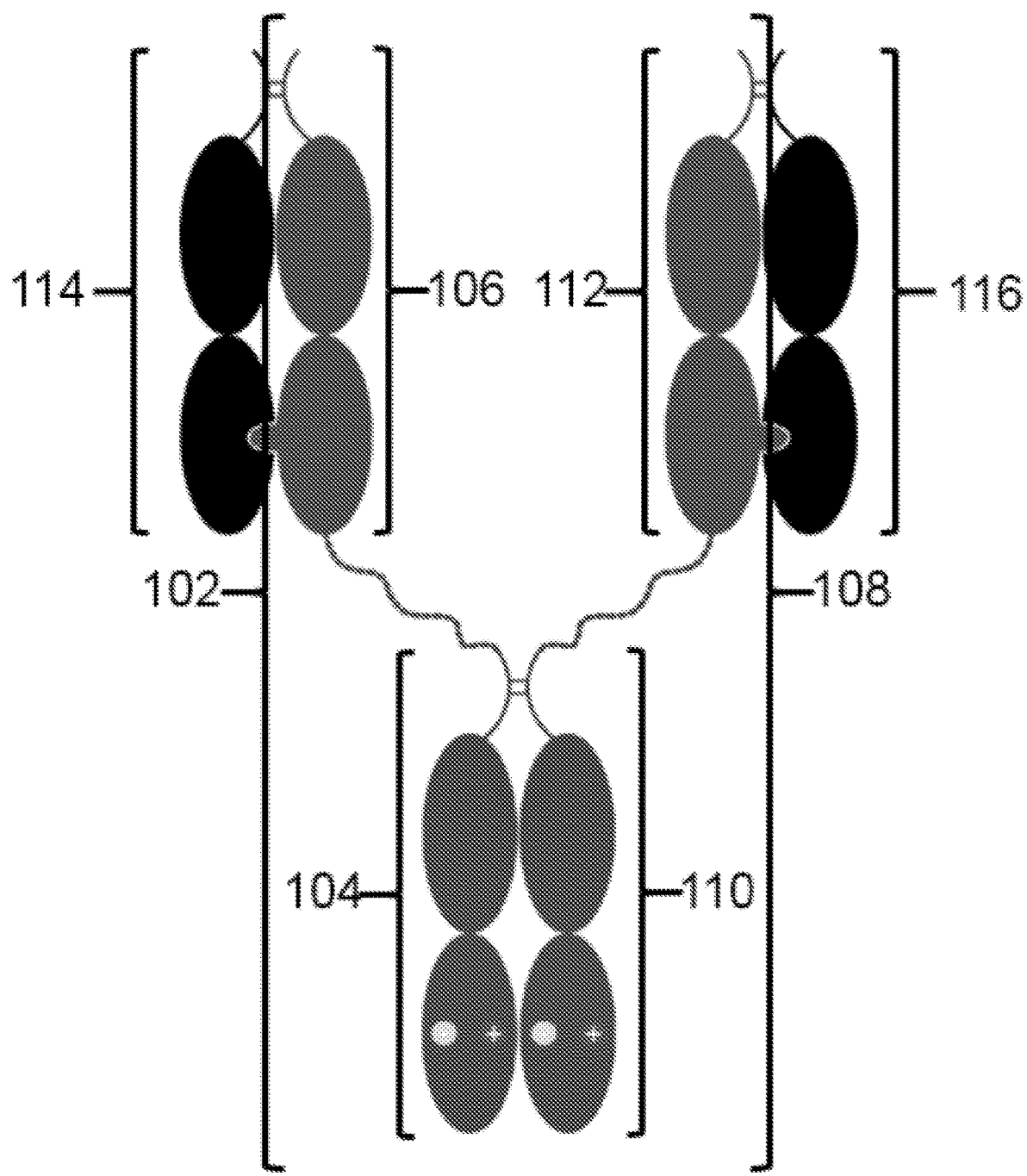
FIG. 1 is an illustration of Fc constructs (Fc construct 1, Fc construct 2, or Fc construct 3) containing three Fc domains formed from four polypeptides. The first polypeptide (102) contains one Fc domain monomer (104) containing different charged amino acids at the $C_H3$-$C_H3$ interface than the wild-type Fc domain monomer sequence joined in a tandem series with a protuberance-containing Fc domain monomer (106). The second polypeptide (108) contains an Fc domain monomer (110) containing different charged amino acids at the $C_H3$-$C_H3$ interface than the wild-type Fc domain monomer sequence joined in a tandem series with another protuberance-containing Fc domain monomer (112). The third and fourth polypeptides (114 and 116, respectively) each contain a cavity-containing Fc domain monomer.

Therapeutic proteins that include Fc domains of IgG can be used to treat inflammation and immunological and inflammatory diseases, cancers, and infections. The present disclosure features compositions and methods for preparing Fc constructs containing Fc domains (e.g., Fc constructs having 2-10 Fc domains, e.g., Fc constructs having 2, 3, 4, 5, 6, 7, 8, 9, or 10 Fc domains). The Fc constructs described herein facilitate the preparation of homogenous pharmaceutical compositions by incorporating structural features (for example, glycine spacers) that significantly improve manufacturing outcome.

Accordingly, the disclosure features pharmaceutical compositions that include a substantially homogenous population of an Fc construct described herein (e.g., an Fc construct having three Fc domains). Homogeneity is an important aspect of a pharmaceutical composition as it influences the pharmacokinetics and in vivo performance of the composition. Traditionally, in the manufacture of pharmaceutical products, there exists the problem of product heterogeneity that may be caused by several factors depending on how the product is produced. For example, the pharmaceutical product may undergo random product cleavage, proteolysis, degradation, and/or aggregation, off-target association of subunits, and/or inefficient protein folding. Different organisms having different biosynthetic processes or cellular machineries that are used to produce the pharmaceutical product may also cause heterogeneity in the product. Often, the initial culture containing the desired pharmaceutical product needs to undergo a rigorous purification process to produce a less heterogenous composition containing the pharmaceutical product.

The disclosure features, in one aspect, Fc constructs having structural features that significantly improve the folding efficiency of the Fc constructs and minimize off-target association of the subunits, thus, leading to pharmaceutical compositions containing these Fc constructs with high homogeneity. Having a high degree of homogeneity ensures the safety, efficacy, uniformity, and reliability of the pharmaceutical composition. Having a high degree of homogeneity also minimizes potential aggregation or degradation of the pharmaceutical product caused by unwanted materials (e.g., degradation products and/or aggregated products or multimers, as well as limiting off-target and adverse side effects caused by the unwanted materials.

As described in detail herein, the disclosure features substantially homogenous containing Fc constructs that all have the same number of Fc domains, as well as methods of preparing such substantially homogenous compositions.

The Fc constructs described herein include glycine spacers between Fc domains. As is well-known in the art, linkers containing both serines and glycines provide structural flexibility in a protein and are commonly used for joining two polypeptides. We have observed through experimentation (see Example 4) that linkers containing both serines and glycines undergo 0-glycosylation (e.g., O-xylosylation) at multiple serines in the linker and proteolysis at the N-terminal side of serine. We aimed to optimize the linker sequence and length to further improve the homogeneity of the Fc constructs. We made Fc constructs in which all the linkers within the constructs are glycine spacers having only glycines (e.g., at least 12 glycines, e.g., 12-30 glycines; e.g., 20 glycines, SEQ ID NO: 27). Having all glycine spacers in the Fc constructs further improved the homogeneity of the Fc constructs by removing O-glycosylation at serines and also decreasing the rate of proteolysis of the constructs (see Example 4). Consequently, we were able to achieve a more substantially homogenous population of Fc constructs by using all glycine spacers in the Fc constructs.

Homogeneity is the result of Fc construct components. For example, in a first approach ("approach (a)"), incorporation of linkers containing only glycines to join Fc domain monomers may be utilized. As we observed through experimentation, all-glycine spacers (e.g., at least 12 glycines, e.g., 12-30 glycines; SEQ ID NO: 27) in an Fc construct do not undergo O-glycosylation and are less susceptible to proteolysis as compared to traditional linkers that include serines and glycines (see Example 4).

In addition, in another approach ("approach (b)"), homogeneity of a composition containing an Fc construct described herein (e.g., an Fc construct having three Fc domains) is improved by removal of C-terminal lysines. Such C-terminal lysine residue are highly conserved in immunoglobulins across many species and may be fully or partially removed by the cellular machinery during protein production. Removal of the C-terminal lysines in the Fc constructs of the disclosure improves uniformity of the resulting composition and achieves a more homogenous Fc construct preparation (see Example 8). For example, in some embodiments of Fc constructs described herein (e.g., an Fc construct having three Fc domains), the codon of the C-terminal lysine is removed, thus, generating Fc constructs having polypeptides without C-terminal lysine residues and a resultant homogenous population.

A further approach ("approach (c)") to improve the homogeneity of a composition containing an Fc construct described herein (e.g., an Fc construct having three Fc domains), two sets of heterodimerizing selectivity modules were utilized: (i) heterodimerizing selectivity modules having different reverse charge mutations and (ii) heterodimerizing selectivity modules having engineered cavities and protuberances. We have observed through experimentation, e.g., see Example 6, that when trying to form a heterodimeric Fc domain in an Fc construct, having both (i) and (ii) further improved the homogeneity of the pharmaceutical composition produced by reducing uncontrolled association of Fc domain monomers, and therefore undesirable oligomers and multimers. In particular examples, an Fc domain monomer containing (i) at least one reverse charge mutation and (ii) at least one engineered cavity or at least one engineered protuberance may be produced and will selectively combine with another Fc domain monomer containing (i) at least one reverse charge mutation and (ii) at least one engineered protuberance or at least one engineered cavity to form an Fc domain. In another example, an Fc domain monomer containing reversed charge mutation K370D and engineered cavities Y349C, T366S, L368A, and Y407V and another Fc domain monomer containing reversed charge mutation E357K and engineered protuberances S354C and T366W may be produced and will selectively combine to form an Fc domain.

As described in detail herein, a substantially homogenous composition containing an Fc construct of the disclosure (e.g., an Fc construct having three Fc domains) may be achieved by using all-glycine spacers between two Fc domain monomers in the Fc construct (approach (a)), by using polypeptides that lack C-terminal lysines in the Fc construct (approach (b)), and/or by using two sets of heterodimerizing selectivity modules ((i) heterodimerizing selectivity modules having different reverse charge mutations and (ii) heterodimerizing selectivity modules having engineered cavities and protuberances) to promote heterodimeric Fc domain formation by some Fc domain monomers in the Fc construct (approach (c)).

In some embodiments, a substantially homogenous composition containing an Fc construct described herein (e.g., an Fc construct having three Fc domains) may be achieved through approach (a).

In some embodiments, a substantially homogenous composition containing an Fc construct described herein (e.g., an Fc construct having three Fc domains) may be achieved through approach (b).

In some embodiments, a substantially homogenous composition containing an Fc construct described herein (e.g., an Fc construct having three Fc domains) may be achieved through approach (c).

In some embodiments, a substantially homogenous composition containing an Fc construct described herein (e.g., an Fc construct having three Fc domains) may be achieved through a combination of approaches (a) and (b).

In some embodiments, a substantially homogenous composition containing an Fc construct described herein (e.g., an Fc construct having three Fc domains) may be achieved through a combination of approaches (a) and (c).

In some embodiments, a substantially homogenous composition containing an Fc construct described herein (e.g., an Fc construct having three Fc domains) may be achieved through a combination of approaches (b) and (c).

In some embodiments, a substantially homogenous composition containing an Fc construct described herein (e.g., an Fc construct having three Fc domains) may be achieved through a combination of approaches (a), (b), and (c).

In some embodiments, to further improve the homogeneity of the pharmaceutical composition containing an Fc construct described herein, the N-terminal Asp in one or more of the polypeptides in the Fc construct in the composition is mutated to Gln. In some embodiments of a composition including a substantially homogenous population of an Fc construct described herein, the N-terminal Asp in each of the polypeptides in the Fc construct in the composition is mutated to Gln.

Furthermore, in Fc constructs of the disclosure (e.g., an Fc construct having three Fc domains), the length of the linkers that join Fc domain monomers influences the folding efficiency of the Fc constructs. In some embodiments, a linker having at least 4, 8, or 12 glycines (e.g., 4-30, 8-30, 12-30 glycines; SEQ ID NOs: 26 and 27) may be used to join Fc domain monomers in Fc constructs of the disclosure.

I. Fc Domain Monomers

An Fc domain monomer includes a hinge domain, a $C_H2$ antibody constant domain, and a $C_H3$ antibody constant domain. The Fc domain monomer can be of immunoglobulin antibody isotype IgG, IgE, IgM, IgA, or IgD. The Fc domain monomer may also be of any immunoglobulin antibody isotype (e.g., IgG1, IgG2a, IgG2b, IgG3, or IgG4). The Fc domain monomers may also be hybrids, e.g., with the hinge and $C_H2$ from IgG1 and the $C_H3$ from IgA, or with the hinge and $C_H2$ from IgG1 but the $C_H3$ from IgG3. A dimer of Fc domain monomers is an Fc domain (further defined herein) that can bind to an Fc receptor, e.g., FcγRIIIa, which is a receptor located on the surface of leukocytes. In the present disclosure, the $C_H3$ antibody constant domain of an Fc domain monomer may contain amino acid substitutions at the interface of the $C_H3$-$C_H3$ antibody constant domains to promote their association with each other. In other embodiments, an Fc domain monomer includes an additional moiety, e.g., an albumin-binding peptide or a purification peptide, attached to the N- or C-terminus. In the present disclosure, an Fc domain monomer does not contain any type of antibody variable region, e.g., $V_H$, $V_L$, a complementarity determining region (CDR), or a hypervariable region (HVR). The Fc domain monomer can be of different origins, e.g., human, mouse, or rat.

In some embodiments, an Fc domain monomer in an Fc construct described herein (e.g., an Fc construct having three Fc domains) may have a sequence that is at least 95% identical (e.g., at least 97%, 99%, or 99.5% identical) to the sequence of a wild-type Fc domain monomer (SEQ ID NO: 42). In some embodiments, an Fc domain monomer in an Fc construct described herein (e.g., an Fc construct having three Fc domains) may comprise, consist of, or consist essentially of a sequence that is the sequence of a wild-type Fc domain monomer (SEQ ID NO: 42) with up to 10 (9, 8, 7, 6, 5, 4, 3, 2, or 1) single amino acid modifications (e.g., substitutions, e.g., conservative substitutions). In some embodiments, an Fc domain monomer in an Fc construct described herein (e.g., an Fc construct having three Fc domains) may have a sequence that is at least 95% identical (e.g., at least 97%, 99%, or 99.5% identical) to the sequence of any one of SEQ ID NOs: 44, 46, 48, and 50-53 (see Example 1, Tables 4 and 5). In some embodiments, an Fc domain monomer in an Fc construct described herein (e.g., an Fc construct having three Fc domains) may have a sequence that is the sequence of any one of SEQ ID NOs: 44, 46, 48, and 50-53 (see Example 1, Tables 4 and 5) with up to 10 (9, 8, 7, 6, 5, 4, 3, 2, or 1) single amino acid modifications (e.g., substitutions, e.g., conservative substitutions). In certain embodiments, an Fc domain monomer in the Fc construct may have a sequence that is at least 95% identical (e.g., at least 97%, 99%, or 99.5% identical) to the sequence of any one of SEQ ID NOs: 48, 52, and 53. In certain embodiments, an Fc domain monomer in the Fc construct may have a sequence that is the sequence of any one of SEQ ID NOs: 48, 52, and 53 with up to 10 (e.g., 9, 8, 7, 6, 5, 4, 3, 2, or 1) single amino acid modifications (e.g., substitutions, e.g., conservative substitutions).

SEQ ID NO: 42: wild-type human IgG1 Fc domain monomer amino acid sequence
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

SEQ ID NO: 44
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK

SEQ ID NO: 46
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPG

SEQ ID NO: 48
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVD

GFYPSDIAVEWESNGQPENNYKTTPPVLDSDGSFFLVSKLTVDKSRWQQG

NVFSCSVMHEALHNHYTQKSLSLSPG

SEQ ID NO: 50
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK

SEQ ID NO: 51
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLKSDGSFFLYSDLTVDKSRWQQG

NVFSCSVMHEALHNHYTQKSLSLSPGK

SEQ ID NO: 52
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLKSDGSFFLYSDLTVDKSRWQQG

NVFSCSVMHEALHNHYTQKSLSLSPG

SEQ ID NO: 53
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDKLTKNQVSLWCLVK

GFYPSDIAVEWESNGQPENNYKTTPPVLDSDGSFFLYSKLTVDKSRWQQG

NVFSCSVMHEALHNHYTQKSLSLSPGK

II. Fc Domains

As defined herein, an Fc domain includes two Fc domain monomers that are dimerized by the interaction between the $C_H3$ antibody constant domains. In the present disclosure, an Fc domain does not include a variable region of an antibody, e.g., $V_H$, $V_L$, CDR, or HVR. An Fc domain forms the minimum structure that binds to an Fc receptor, e.g., Fc-gamma receptors (i.e., Fcγ receptors (FcγR)), Fc-alpha receptors (i.e., Fcα receptors (FcαR)), Fc-epsilon receptors (i.e., Fcε receptors (FcεR)), and/or the neonatal Fc receptor (FcRn). In some embodiments, an Fc domain of the present disclosure binds to an Fcγ receptor (e.g., FcγRI (CD64), FcγRIIa (CD32), FcγRIIb (CD32), FcγRIIIa (CD16a), FcγRIIIb (CD16b)), and/or FcγRIV and/or the neonatal Fc receptor (FcRn).

In any of the Fc constructs described herein, the amino acid modification may alter binding affinity to one or more Fc receptors. In some embodiments the amino acid modification is S267E/L328F. In some embodiments, the Fc receptor is FcγRIIb. In some cases, the modification described herein increases affinity to the FcγRIIb receptor. In some cases, the S267E/L328F modification increases binding affinity to FcγRIIb.

III. Dimerization Selectivity Modules

In the present disclosure, a dimerization selectivity module is the part of the Fc domain monomer that facilitates the preferred pairing of two Fc domain monomers to form an Fc domain. Specifically, a dimerization selectivity module is that part of the $C_H3$ antibody constant domain of an Fc domain monomer which includes amino acid substitutions positioned at the interface between interacting $C_H3$ antibody constant domains of two Fc domain monomers. In a dimerization selectivity module, the amino acid substitutions make favorable the dimerization of the two $C_H3$ antibody constant domains as a result of the compatibility of amino acids chosen for those substitutions. The ultimate formation of the favored Fc domain is selective over other Fc domains which form from Fc domain monomers lacking dimerization selectivity modules or with incompatible amino acid substitutions in the dimerization selectivity modules. This type of amino acid substitution can be made using conventional molecular cloning techniques well-known in the art, such as QuikChange® mutagenesis.

In some embodiments, a dimerization selectivity module includes an engineered cavity (described further herein) in the $C_H3$ antibody constant domain. In other embodiments, a dimerization selectivity module includes an engineered protuberance (described further herein) in the $C_H3$ antibody constant domain. To selectively form an Fc domain, two Fc domain monomers with compatible dimerization selectivity modules, e.g., one $C_H3$ antibody constant domain containing an engineered cavity and the other $C_H3$ antibody constant domain containing an engineered protuberance, combine to form a protuberance-into-cavity pair of Fc domain monomers. Engineered protuberances and engineered cavities are examples of heterodimerizing selectivity modules, which can be made in the $C_H3$ antibody constant domains of Fc domain monomers in order to promote favorable heterodimerization of two Fc domain monomers that have compatible heterodimerizing selectivity modules.

In other embodiments, an Fc domain monomer with a dimerization selectivity module containing positively-charged amino acid substitutions and an Fc domain monomer with a dimerization selectivity module containing negatively-charged amino acid substitutions may selectively combine to form an Fc domain through the favorable electrostatic steering (described further herein) of the charged amino acids. In some embodiments, an Fc domain monomer may include one of the following positively-charged and negatively-charged amino acid substitutions: K392D, K392E, D399K, K409D, K409E, K439D, and K439E. In one example, an Fc domain monomer containing a positively-charged amino acid substitution, e.g., D356K or E357K, and an Fc domain monomer containing a negatively-charged amino acid substitution, e.g., K370D or K370E, may selectively combine to form an Fc domain through favorable electrostatic steering of the charged amino acids. In another example, an Fc domain monomer containing E357K and an Fc domain monomer containing K370D may selectively combine to form an Fc domain through favorable electrostatic steering of the charged amino acids. In some embodiments, reverse charge amino acid substitutions may be used as heterodimerizing selectivity modules, wherein two Fc domain monomers containing different, but compatible, reverse charge amino acid substitutions combine to form a heterodimeric Fc domain. Specific dimerization selectivity modules are further listed, without limitation, in Tables 1 and 2A described further below.

In other embodiments, two Fc domain monomers include homodimerizing selectivity modules containing identical reverse charge mutations in at least two positions within the ring of charged residues at the interface between $C_H3$ domains. Homodimerizing selectivity modules are reverse charge amino acid substitutions that promote the homodimerization of Fc domain monomers to form a homodimeric Fc domain. By reversing the charge of both members of two or more complementary pairs of residues in the two Fc domain monomers, mutated Fc domain monomers remain complementary to Fc domain monomers of the same mutated sequence, but have a lower complementarity to Fc domain monomers without those mutations. In one embodiment, an Fc domain includes Fc domain monomers including the double mutants K409D/D399K, K392D/D399K, E357K/K370E, D356K/K439D, K409E/D399K, K392E/D399K, E357K/K370D, or D356K/K439E. In another embodiment, an Fc domain includes Fc domain monomers including quadruple mutants combining any pair of the double mutants, e.g., K409D/D399K/E357K/K370E. Examples of homodimerizing selectivity modules are further shown in Tables 2B and 2C.

An unmodified Fc domain monomer can be a naturally occurring human Fc domain monomer or a WT human Fc domain monomer. An Fc domain monomer can be a naturally occurring human Fc domain monomer comprising a hinge, a CH2 domain, and a CH3 domain; or a variant thereof having up to 16 (e.g., up to 2, 3, 4, 5, 6, 7, 8, 9, 10, 11, 12, 13, 14, 15, or 16) amino acid modifications (e.g., single amino acid modifications) to accommodate or promote directed dimerization. In some cases, the Fc domain includes at least one amino acid modification, wherein the amino acid modifications alter one or more of (i) binding affinity to one or more Fc receptors, (ii) effector functions, (iii) the level of Fc domain sulfation, (iv) half-life, (v) protease resistance, (vi) Fc domain stability, and/or (vii) susceptibility to degradation (e.g., when compared to the unmodified Fc domain). In further embodiments, an Fc domain monomer containing (i) at least one reverse charge mutation and (ii) at least one engineered cavity or at least one engineered protuberance may selectively combine with another Fc domain monomer containing (i) at least one reverse charge mutation and (ii) at least one engineered protuberance or at least one engineered cavity to form an Fc domain. For example, an Fc domain monomer containing reversed charge mutation K370D and engineered cavities Y349C, T366S, L368A, and Y407V and another Fc domain monomer containing reversed charge mutation E357K and engineered protuberances S354C and T366W may selectively combine to form an Fc domain. In some cases, the Fc domain includes no more than 16 amino acid modifications (e.g., no more than 2, 3, 4, 5, 6, 7, 8, 9, 10, 11, 12, 13, 14, 15, or 16 amino acid modifications in the CH3 domain).

The formation of such Fc domains is promoted by the compatible amino acid substitutions in the $C_H3$ antibody constant domains. Two dimerization selectivity modules containing incompatible amino acid substitutions, e.g., both containing engineered cavities, both containing engineered protuberances, or both containing the same charged amino acids at the $C_H3$-$C_H3$ interface, will not promote the formation of a heterodimeric Fc domain.

Furthermore, other methods used to promote the formation of Fc domains with defined Fc domain monomers include, without limitation, the LUZ-Y approach (U.S. Patent Application Publication No. WO2011034605) which includes C-terminal fusion of a monomer α-helices of a leucine zipper to each of the Fc domain monomers to allow heterodimer formation, as well as strand-exchange engineered domain (SEED) body approach (Davis et al., *Protein Eng Des Sel.* 23:195-202, 2010) that generates Fc domain with heterodimeric Fc domain monomers each including alternating segments of IgA and IgG $C_H3$ sequences.

IV. Engineered Cavities and Engineered Protuberances

The use of engineered cavities and engineered protuberances (or the "knob-into-hole" strategy) is described by Carter and co-workers (Ridgway et al., Protein Eng. 9:617-612, 1996; Atwell et al., J Mol Biol. 270:26-35, 1997; Merchant et al., Nat Biotechnol. 16:677-681, 1998). The knob and hole interaction favors heterodimer formation, whereas the knob-knob and the hole-hole interaction hinder homodimer formation due to steric clash and deletion of favorable interactions. The "knob-into-hole" technique is also disclosed in U.S. Pat. No. 5,731,168.

In the present disclosure, engineered cavities and engineered protuberances are used in the preparation of the Fc constructs described herein. An engineered cavity is a void that is created when an original amino acid in a protein is replaced with a different amino acid having a smaller side-chain volume. An engineered protuberance is a bump that is created when an original amino acid in a protein is replaced with a different amino acid having a larger side-chain volume. Specifically, the amino acid being replaced is in the $C_H3$ antibody constant domain of an Fc domain monomer and is involved in the dimerization of two Fc domain monomers. In some embodiments, an engineered cavity in one $C_H3$ antibody constant domain is created to accommodate an engineered protuberance in another $C_H3$ antibody constant domain, such that both $C_H3$ antibody constant domains act as dimerization selectivity modules (e.g., heterodimerizing selectivity modules) (described above) that promote or favor the dimerization of the two Fc domain monomers. In other embodiments, an engineered cavity in one $C_H3$ antibody constant domain is created to better accommodate an original amino acid in another $C_H3$ antibody constant domain. In yet other embodiments, an engineered protuberance in one $C_H3$ antibody constant domain is created to form additional interactions with original amino acids in another $C_H3$ antibody constant domain.

An engineered cavity can be constructed by replacing amino acids containing larger side chains such as tyrosine or tryptophan with amino acids containing smaller side chains such as alanine, valine, or threonine. Specifically, some dimerization selectivity modules (e.g., heterodimerizing selectivity modules) (described further above) contain engineered cavities such as Y407V mutation in the $C_H3$ antibody constant domain. Similarly, an engineered protuberance can be constructed by replacing amino acids containing smaller side chains with amino acids containing larger side chains. Specifically, some dimerization selectivity modules (e.g., heterodimerizing selectivity modules) (described further above) contain engineered protuberances such as T366W mutation in the $C_H3$ antibody constant domain. In the present disclosure, engineered cavities and engineered protuberances are also combined with inter-$C_H3$ domain disulfide bond engineering to enhance heterodimer formation. In one example, an Fc domain monomer containing engineered cavities Y349C, T366S, L368A, and Y407V may selectively combine with another Fc domain monomer containing engineered protuberances S354C and T366W to form an Fc domain. In another example, an Fc domain monomer containing engineered cavity Y349C and an Fc domain monomer containing engineered protuberance S354C may selectively combine to form an Fc domain. Other engineered cavities and engineered protuberances, in combination with either disulfide bond engineering or structural calculations (mixed HA-TF) are included, without limitation, in Table 1.

TABLE 1

| Strategy | $CH_3$ antibody constant domain of Fc domain monomer 1 | $CH_3$ antibody constant domain of Fc domain monomer 2 | Reference |
| --- | --- | --- | --- |
| Engineered cavities and protuberances ("knob-into-hole") | Y407T | T366Y | U.S. Pat. No. 8,216,805 |
| | Y407A | T366W | U.S. Pat. No. 8,216,805 |
| | F405A | T394W | U.S. Pat. No. 8,216,805 |
| | Y407T | T366Y | U.S. Pat. No. 8,216,805 |
| | T394S | F405W | U.S. Pat. No. 8,216,805 |
| | T394W:Y407T | T366Y:F405A | U.S. Pat. No. 8,216,805 |
| | T394S:Y407A | T366W:F405W | U.S. Pat. No. 8,216,805 |
| | T366W:T394S | F406W:Y407A | U.S. Pat. No. 8,216,805 |
| Engineered cavities and protuberances ("knob-into-hole"), S-S engineering | T366S:L368A:Y407V:Y349C | T366W:S354C | Zeidler et al., J Immunol. 163: 1246-52, 1999 |
| MixedHA-TF | S364H:F405A | Y349T:T394F | WO2006106905 |

Replacing an original amino acid residue in the $C_H3$ antibody constant domain with a different amino acid residue can be achieved by altering the nucleic acid encoding the original amino acid residue. The upper limit for the number of original amino acid residues that can be replaced is the total number of residues in the interface of the $C_H3$ antibody constant domains, given that sufficient interaction at the interface is still maintained.

V. Electrostatic Steering

Electrostatic steering is the utilization of favorable electrostatic interactions between oppositely charged amino acids in peptides, protein domains, and proteins to control the formation of higher ordered protein molecules. A method of using electrostatic steering effects to alter the interaction of antibody domains to reduce for formation of homodimer in favor of heterodimer formation in the generation of bi-specific antibodies is disclosed in U.S. Patent Application Publication No. 2014-0024111.

In the present disclosure, electrostatic steering is used to control the dimerization of Fc domain monomers and the formation of Fc constructs. In particular, to control the dimerization of Fc domain monomers using electrostatic steering, one or more amino acid residues that make up the $C_H3$-$C_H3$ interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In other embodiments, a negatively-charged amino acid in the interface is replaced with a positively-charged amino acid. The charged amino acids may be introduced to one of the interacting $C_H3$ antibody constant domains, or both. By introducing charged amino acids to the interacting $C_H3$ antibody constant domains, dimerization selectivity modules (described further above) are created that can selectively form dimers of Fc domain monomers as controlled by the electrostatic steering effects resulting from the interaction between charged amino acids.

In some embodiments, to create a dimerization selectivity module including reversed charges that can selectively form dimers of Fc domain monomers as controlled by the electrostatic steering effects, the two Fc domain monomers may be selectively formed through heterodimerization or homodimerization.

Heterodimerization of Fc Domain Monomers

Heterodimerization of Fc domain monomers can be promoted by introducing different, but compatible, mutations in the two Fc domain monomers, such as the charge residue pairs included, without limitation, in Table 2A. In some embodiments, an Fc domain monomer may include one of the following positively-charged and negatively-charged amino acid substitutions: D356K, D356R, E357K, E357R, K370D, K370E, K392D, K392E, D399K, K409D, K409E, K439D, and K439E. In one example, an Fc domain monomer containing a positively-charged amino acid substitution, e.g., D356K or E357K, and an Fc domain monomer containing a negatively-charged amino acid substitution, e.g., K370D or K370E, may selectively combine to form an Fc domain through favorable electrostatic steering of the charged amino acids. In another example, an Fc domain monomer containing E357K and an Fc domain monomer containing K370D may selectively combine to form an Fc domain through favorable electrostatic steering of the charged amino acids.

Figure 2:
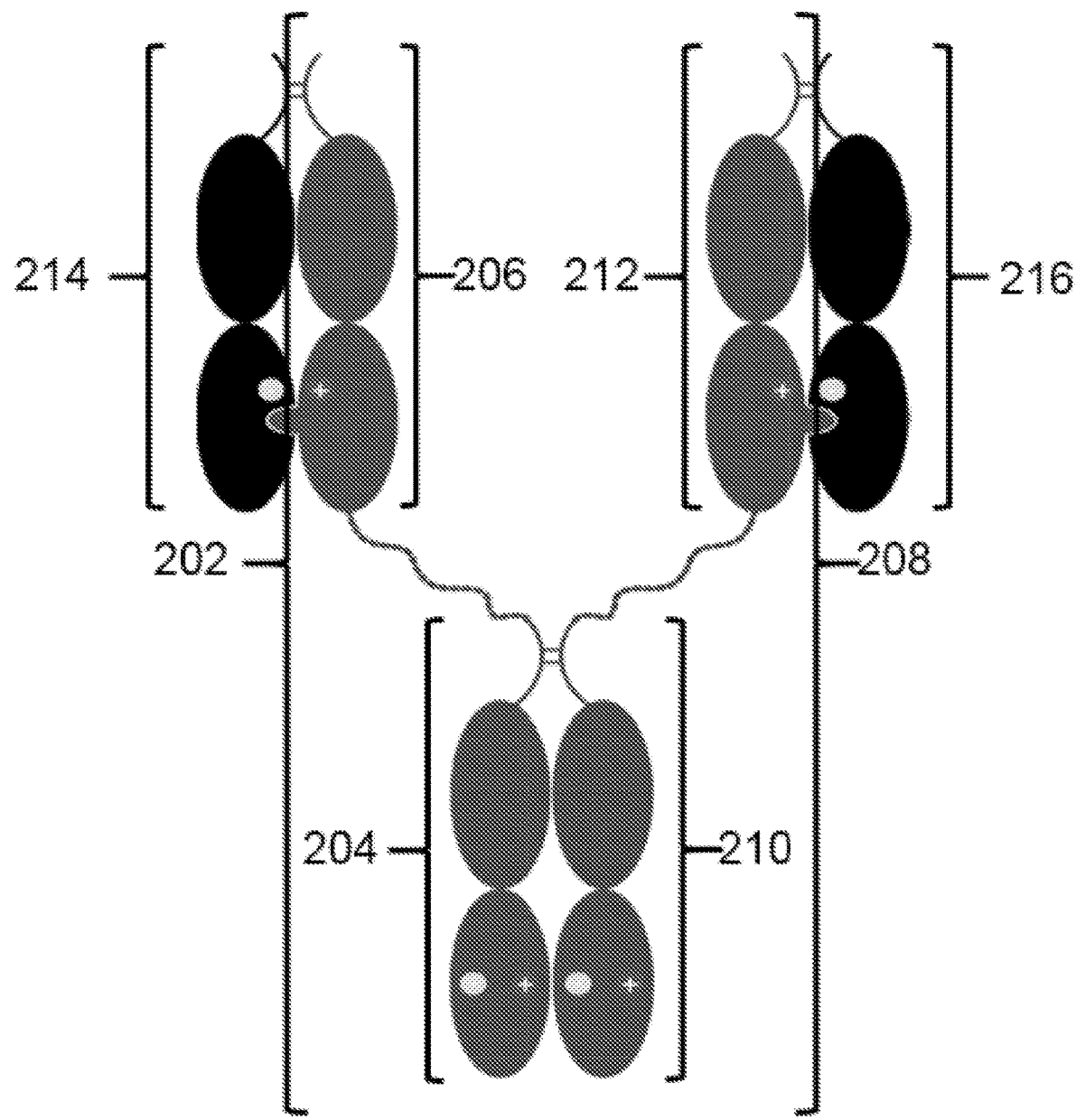
FIG. 2 is an illustration of an Fc construct (Fc construct 4) containing three Fc domains formed from four polypeptides. The first polypeptide (202) contains one Fc domain monomer (204) containing different charged amino acids at the $C_H3$-$C_H3$ interface than the wild-type Fc domain monomer sequence joined in a tandem series with another Fc domain monomer (206) containing different charged amino acids and a protuberance. The second polypeptide (208) contains an Fc domain monomer (210) containing different charged amino acids at the $C_H3$-$C_H3$ interface than the wild-type Fc domain monomer sequence joined in a tandem series with another Fc domain monomer (212) containing different charged amino acids and a protuberance. The third and fourth polypeptides (214 and 216, respectively) each contain an Fc domain monomer containing different charged amino acids and a cavity.

For example, in an Fc construct having three Fc domains, two of the three Fc domains may be formed by the heterodimerization of two Fc domain monomers, as promoted by the electrostatic steering effects. A "heterodimeric Fc domain" refers to an Fc domain that is formed by the heterodimerization of two Fc domain monomers, wherein the two Fc domain monomers contain different reverse charge mutations (heterodimerizing selectivity modules) (see, e.g., mutations in Table 2A) that promote the favorable formation of these two Fc domain monomers. As shown in FIGS. 1 and 2, in an Fc construct having three Fc domains—one carboxyl terminal "stem" Fc domain and two amino terminal "branch" Fc domains—each of the amino terminal "branch" Fc domains may be a heterodimeric Fc domain (also called a "branch heterodimeric Fc domain") (e.g., a heterodimeric Fc domain formed by Fc domain monomers 106 and 114 or Fc domain monomers 112 and 116 in FIG. 1; a heterodimeric Fc domain formed by Fc domain monomers 206 and 214 or Fc domain monomers 212 and 216 in FIG. 2). A branch heterodimeric Fc domain may be formed by an Fc domain monomer containing E357K and another Fc domain monomer containing K370D.

TABLE 2A

| Reverse charge mutation(s) in $C_H3$ antibody constant domain of Fc domain monomer 1 | Reverse charge mutation(s) in $C_H3$ antibody constant domain of Fc domain monomer 2 |
|---|---|
| K409D | D399K |
| K409D | D399R |
| K409E | D399K |
| K409E | D399R |
| K392D | D399K |
| K392D | D399R |
| K392E | D399K |
| K392E | D399R |

TABLE 2A-continued

| Reverse charge mutation(s) in $C_H3$ antibody constant domain of Fc domain monomer 1 | Reverse charge mutation(s) in $C_H3$ antibody constant domain of Fc domain monomer 2 |
|---|---|
| K370D | E357K |
| K370D | E357R |
| K370E | E357K |
| K370E | E357R |
| K370D | D356K |
| K370D | D356R |
| K370E | D356K |
| K370E | D356R |
| K409D, K392D | D399K, E356K |
| K370E, K409D, K439E | E356K, E357K, D399K |

Homodimerization of Fc Domain Monomers

Homodimerization of Fc domain monomers can be promoted by introducing the same electrostatic steering mutations (homodimerizing selectivity modules) in both Fc domain monomers in a symmetric fashion. In some embodiments, two Fc domain monomers include homodimerizing selectivity modules containing identical reverse charge mutations in at least two positions within the ring of charged residues at the interface between $C_H3$ domains. By reversing the charge of both members of two or more complementary pairs of residues in the two Fc domain monomers, mutated Fc domain monomers remain complementary to Fc domain monomers of the same mutated sequence, but have a lower complementarity to Fc domain monomers without those mutations. Electrostatic steering mutations that may be introduced into an Fc domain monomer to promote its homodimerization are shown, without limitation, in Tables 2B and 2C. In one embodiment, an Fc domain includes two Fc domain monomers each including the double reverse charge mutants (Table 2B), e.g., K409D/D399K. In another embodiment, an Fc domain includes two Fc domain monomers each including quadruple reverse mutants (Table 2C), e.g., K409D/D399K/K370D/E357K.

For example, in an Fc construct having three Fc domains, one of the three Fc domains may be formed by the homodimerization of two Fc domain monomers, as promoted by the electrostatic steering effects. A "homodimeric Fc domain" refers to an Fc domain that is formed by the homodimerization of two Fc domain monomers, wherein the two Fc domain monomers contain the same reverse charge mutations (see, e.g., mutations in Tables 2B and 2C). As shown in FIGS. 1 and 2, in an Fc construct having three Fc domains—one carboxyl terminal "stem" Fc domain and two amino terminal "branch" Fc domains—the carboxy terminal "stem" Fc domain may be a homodimeric Fc domain (also called a "stem homodimeric Fc domain") (e.g., a homodimeric Fc domain formed by Fc domain monomers 104 and 110 in FIG. 1; a homodimeric Fc domain formed by Fc domain monomers 204 and 210 in FIG. 2). A stem homodimeric Fc domain may be formed by two Fc domain monomers each containing the double mutants K409D/D399K.

TABLE 2B

| Reverse charge mutation(s) in $C_H3$ antibody constant domain of each of the two Fc domain monomers in a homodimeric Fc domain |
|---|
| K409D/D399K |
| K409D/D399R |
| K409E/D399K |
| K409E/D399R |
| K392D/D399K |

TABLE 2B-continued

Reverse charge mutation(s) in $C_H3$ antibody constant domain of each of the two Fc domain monomers in a homodimeric Fc domain K392D/D399R
K392E/D399K
K392E/D399R
K370D/E357K
K370D/E357R
K370E/E357K
K370E/E357R
K370D/D356K
K370D/D356R
K370E/D356K
K370E/D356R

TABLE 2C

| Reverse charge mutation(s) in $C_H3$ constant domain of each of the two Fc domain monomers in a homodimeric Fc domain | Reverse charge mutation(s) in $C_H3$ antibody constant domain of each of the two Fc domain monomers in a homodimeric Fc domain |
|---|---|
| K409D/D399K/K370D/E357K | K392D/D399K/K370D/E357K |
| K409D/D399K/K370D/E357R | K392D/D399K/K370D/E357R |
| K409D/D399K/K370E/E357K | K392D/D399K/K370E/E357K |
| K409D/D399K/K370E/E357R | K392D/D399K/K370E/E357R |
| K409D/D399K/K370D/D356K | K392D/D399K/K370D/D356K |
| K409D/D399K/K370D/D356R | K392D/D399K/K370D/D356R |
| K409D/D399K/K370E/D356K | K392D/D399K/K370E/D356K |
| K409D/D399K/K370E/D356R | K392D/D399K/K370E/D356R |
| K409D/D399R/K370D/E357K | K392D/D399R/K370D/E357K |
| K409D/D399R/K370D/E357R | K392D/D399R/K370D/E357R |
| K409D/D399R/K370E/E357K | K392D/D399R/K370E/E357K |
| K409D/D399R/K370E/E357R | K392D/D399R/K370E/E357R |
| K409D/D399R/K370D/D356K | K392D/D399R/K370D/D356K |
| K409D/D399R/K370D/D356R | K392D/D399R/K370D/D356R |
| K409D/D399R/K370E/D356K | K392D/D399R/K370E/D356K |
| K409D/D399R/K370E/D356R | K392D/D399R/K370E/D356R |
| K409E/D399K/K370D/E357K | K392E/D399K/K370D/E357K |
| K409E/D399K/K370D/E357R | K392E/D399K/K370D/E357R |
| K409E/D399K/K370E/E357K | K392E/D399K/K370E/E357K |
| K409E/D399K/K370E/E357R | K392E/D399K/K370E/E357R |
| K409E/D399K/K370D/D356K | K392E/D399K/K370D/D356K |
| K409E/D399K/K370D/D356R | K392E/D399K/K370D/D356R |
| K409E/D399K/K370E/D356K | K392E/D399K/K370E/D356K |
| K409E/D399K/K370E/D356R | K392E/D399K/K370E/D356R |
| K409E/D399R/K370D/E357K | K392E/D399R/K370D/E357K |
| K409E/D399R/K370D/E357R | K392E/D399R/K370D/E357R |
| K409E/D399R/K370E/E357K | K392E/D399R/K370E/E357K |
| K409E/D399R/K370E/E357R | K392E/D399R/K370E/E357R |
| K409E/D399R/K370D/D356K | K392E/D399R/K370D/D356K |
| K409E/D399R/K370D/D356R | K392E/D399R/K370D/D356R |
| K409E/D399R/K370E/D356K | K392E/D399R/K370E/D356K |
| K409E/D399R/K370E/D356R | K392E/D399R/K370E/D356R |

VI. Linkers

In the present disclosure, a linker is used to describe a linkage or connection between polypeptides or protein domains and/or associated non-protein moieties. In some embodiments, a linker is a linkage or connection between at least two Fc domain monomers, for which the linker connects the C-terminus of the $C_H3$ antibody constant domain of a first Fc domain monomer to the N-terminus of the hinge domain of a second Fc domain monomer, such that the two Fc domain monomers are joined to each other in tandem series. In other embodiments, a linker is a linkage between an Fc domain monomer and any other protein domains that are attached to it. For example, a linker can attach the C-terminus of the $C_H3$ antibody constant domain of an Fc domain monomer to the N-terminus of an albumin-binding peptide.

A linker can be a simple covalent bond, e.g., a peptide bond, a synthetic polymer, e.g., a polyethylene glycol (PEG) polymer, or any kind of bond created from a chemical reaction, e.g., chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a polynucleotide sequence encoding the DNA sequences of both proteins, e.g., two Fc domain monomer, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two proteins together. Such chemical conjugation procedures are routine for those skilled in the art.

Spacer

In the present disclosure, a linker between two Fc domain monomers can be an amino acid spacer including 3-200 amino acids (e.g., 3-200, 3-180, 3-160, 3-140, 3-120, 3-100, 3-90, 3-80, 3-70, 3-60, 3-50, 3-45, 3-40, 3-35, 3-30, 3-25, 3-20, 3-15, 3-10, 3-9, 3-8, 3-7, 3-6, 3-5, 3-4, 4-200, 5-200, 6-200, 7-200, 8-200, 9-200, 10-200, 15-200, 20-200, 25-200, 30-200, 35-200, 40-200, 45-200, 50-200, 60-200, 70-200, 80-200, 90-200, 100-200, 120-200, 140-200, 160-200, or 180-200 amino acids)(e.g., 3-150, 3-100, 3-60, 3-50, 3-40, 3-30, 3-20, 3-10, 3-8, 3-5, 4-30, 5-30, 6-30, 8-30, 10-20, 10-30, 12-30, 14-30, 20-30, 15-25, 15-30, 18-22, and 20-30 amino acids). In some embodiments, a linker between two Fc domain monomers is an amino acid spacer containing at least 12 amino acids, such as 12-200 amino acids (e.g., 12-200, 12-180, 12-160, 12-140, 12-120, 12-100, 12-90, 12-80, 12-70, 12-60, 12-50, 12-40, 12-30, 12-20, 12-19, 12-18, 12-17, 12-16, 12-15, 12-14, or 12-13 amino acids) (e.g., 14-200, 16-200, 18-200, 20-200, 30-200, 40-200, 50-200, 60-200, 70-200, 80-200, 90-200, 100-200, 120-200, 140-200, 160-200, 180-200, or 190-200 amino acids)(e.g., 3-150, 3-100, 3-60, 3-50, 3-40, 3-30, 3-20, 3-10, 3-8, 3-5, 4-30, 5-30, 6-30, 8-30, 10-20, 10-30, 12-30, 14-30, 20-30, 15-25, 15-30, 18-22, and 20-30 amino acids). In some embodiments, a linker between two Fc domain monomers is an amino acid spacer containing 12-30 amino acids (e.g., 12, 13, 14, 15, 16, 17, 18, 19, 20, 21, 22, 23, 24, 25, 26, 27, 28, 29, or 30 amino acids). Suitable peptide spacers are known in the art, and include, for example, peptide linkers containing flexible amino acid residues such as glycine and serine. In certain embodiments, a spacer can contain motifs, e.g., multiple or repeating motifs, of GS, GGS, GGGGS (SEQ ID NO: 1), GGSG (SEQ ID NO: 2), or SGGG (SEQ ID NO: 3). In certain embodiments, a spacer can contain 2 to 12 amino acids including motifs of GS, e.g., GS, GSGS (SEQ ID NO: 4), GSGSGS (SEQ ID NO: 5), GSGSGSGS (SEQ ID NO: 6), GSGSGSGSGS (SEQ ID NO: 7), or GSGSGSGSGSGS (SEQ ID NO: 8). In certain other embodiments, a spacer can contain 3 to 12 amino acids including motifs of GGS, e.g., GGS, GGSGGS (SEQ ID NO: 9), GGSGGSGGS (SEQ ID NO: 10), and GGSGGSGGSGGS (SEQ ID NO: 11). In yet other embodiments, a spacer can contain 4 to 20 amino acids including motifs of GGSG (SEQ ID NO: 2), e.g., GGSGGGSG (SEQ ID NO: 12), GGSGGGSGGGSG (SEQ ID NO: 13), GGSGGGSGGGSGGGSG (SEQ ID NO: 14), or GGSGGGSGGGSGGGSGGGSG (SEQ ID NO: 15). In other embodiments, a spacer can contain motifs of GGGGS (SEQ ID NO: 1), e.g., GGGGSGGGGS (SEQ ID NO: 16) or GGGGSGGGGSGGGGS (SEQ ID NO: 17). In certain embodiments, a spacer is SGGGSGGGSGGGSGGGSGGG (SEQ ID NO: 18).

In some embodiments, a spacer between two Fc domain monomers contains only glycine residues, e.g., at least 4 glycine residues (e.g., 4-200, 4-180, 4-160, 4-140, 4-40, 4-100, 4-90, 4-80, 4-70, 4-60, 4-50, 4-40, 4-30, 4-20, 4-19, 4-18, 4-17, 4-16, 4-15, 4-14, 4-13, 4-12, 4-11, 4-10, 4-9, 4-8, 4-7, 4-6 or 4-5 glycine residues) (e.g., 4-200, 6-200, 8-200, 10-200, 12-200, 14-200, 16-200, 18-200, 20-200, 30-200, 40-200, 50-200, 60-200, 70-200, 80-200, 90-200, 100-200, 120-200, 140-200, 160-200, 180-200, 190-200 or 20 glycine residues). In certain embodiments, a spacer has 4-30 glycine residues (e.g., 4, 5, 6, 7, 8, 9, 10, 11, 12, 13, 14, 15, 16, 17, 18, 19, 20, 21, 22, 23, 24, 25, 26, 27, 28, 29, or 30 glycine residues). In some embodiments, a spacer containing only glycine residues may not be glycosylated (e.g., O-linked glycosylation, also referred to as O-glycosylation) or may have a decreased level of glycosylation (e.g., a decreased level of O-glycosylation) (e.g., a decreased level of O-glycosylation with glycans such as xylose, mannose, sialic acids, fucose (Fuc), and/or galactose (Gal) (e.g., xylose)) as compared to, e.g., a spacer containing one or more serine residues (e.g., SGGGSGGGSGGGSGGGSGGG (SEQ ID NO: 18)) (see Example 4).

In some embodiments, a spacer containing only glycine residues may not be 0-glycosylated (e.g., O-xylosylation) or may have a decreased level of O-glycosylation (e.g., a decreased level of 0-xylosylation) as compared to, e.g., a spacer containing one or more serine residues (e.g., SGGGSGGGSGGGSGGGSGGG (SEQ ID NO: 18)).

In some embodiments, a spacer containing only glycine residues may not undergo proteolysis or may have a decreased rate of proteolysis as compared to, e.g., a spacer containing one or more serine residues (e.g., SGGGSGGGSGGGSGGGSGGG (SEQ ID NO: 18)) (see Example 4).

In certain embodiments, a spacer can contain motifs of GGGG (SEQ ID NO: 19), e.g., GGGGGGGG (SEQ ID NO: 20), GGGGGGGGGGGG (SEQ ID NO: 21), GGGGGGGGGGGGGGGG (SEQ ID NO: 22), or GGGGGGGGGGGGGGGGGGGG (SEQ ID NO: 23). In certain embodiments, a spacer can contain motifs of GGGGG (SEQ ID NO: 24), e.g., GGGGGGGGGG (SEQ ID NO: 25), or GGGGGGGGGGGGGGG (SEQ ID NO: 26). In certain embodiments, a spacer is GGGGGGGGGGGGGGGGGGGG (SEQ ID NO: 27).

In other embodiments, a spacer can also contain amino acids other than glycine and serine, e.g., GENLYFQSGG (SEQ ID NO: 28), SACYCELS (SEQ ID NO: 29), RSIAT (SEQ ID NO: 30), RPACKIPNDLKQKVMNH (SEQ ID NO: 31), GGSAGGSGSGSSGGSS-GASGTGTAGGTGSGSGTGSG (SEQ ID NO: 32), AAANSSIDLISVPVDSR (SEQ ID NO: 33), or GGSGGGSEGGGSEGGGSEGGGSEGGGSEGGGSGGGS (SEQ ID NO: 34).

In certain embodiments in the present disclosure, a 12- or 20-amino acid peptide spacer is used to connect two Fc domain monomers in tandem series (e.g., polypeptides 102 and 108 in FIG. 1; polypeptides 202 and 208 in FIG. 2), the 12- and 20-amino acid peptide spacers consisting of sequences GGGSGGGSGGGS (SEQ ID NO: 35) and SGGGSGGGSGGGSGGGSGGG (SEQ ID NO: 18), respectively. In other embodiments, an 18-amino acid peptide spacer consisting of sequence GGSGGGSGGGSGGGSGGS (SEQ ID NO: 36) may be used.

In some embodiments, a spacer between two Fc domain monomers comprises, consists of, or consists essentially of a sequence that is at least 75% identical (e.g., at least 77%, 79%, 81%, 83%, 85%, 87%, 89%, 91%, 93%, 95%, 97%, 99%, or 99.5% identical) to the sequence of any one of SEQ ID NOs: 1-36 described above. In certain embodiments, a spacer between two Fc domain monomers comprises, consists of, or consists essentially of a sequence that is at least 80% identical (e.g., at least 82%, 85%, 87%, 90%, 92%, 95%, 97%, 99%, or 99.5% identical) to the sequence of any one of SEQ ID NOs: 17, 18, 26, and 27. In certain embodiments, a spacer between two Fc domain monomers comprises, consists of, or consists essentially of a sequence that is at least 80% identical (e.g., at least 82%, 85%, 87%, 90%, 92%, 95%, 97%, 99%, or 99.5%) to the sequence of SEQ ID NO: 18 or 27. In certain embodiments, a spacer between two Fc domain monomers comprises, consists of, or consists essentially of the sequence of any one of SEQ ID NOs: 1-36 described above.

VII. Serum Protein-Binding Peptides

Binding to serum protein peptides can improve the pharmacokinetics of protein pharmaceuticals, and in particular the Fc constructs described here may be fused with serum protein-binding peptides As one example, albumin-binding peptides that can be used in the methods and compositions described here are generally known in the art. In one embodiment, the albumin binding peptide includes the sequence DICLPRWGCLW (SEQ ID NO: 37). In some embodiments, the albumin binding peptide has a sequence that is at least 80% identical (e.g., 80%, 90%, or 100% identical) to the sequence of SEQ ID NO: 37.

In the present disclosure, albumin-binding peptides may be attached to the N- or C-terminus of certain polypeptides in the Fc construct. In one embodiment, an albumin-binding peptide may be attached to the C-terminus of one or more polypeptides in Fc constructs 1-4 (FIGS. 1 and 2). In another embodiment, an albumin-binding peptide can be fused to the C-terminus of the polypeptide encoding two Fc domain monomers linked in tandem series in Fc constructs 1-4 (e.g., polypeptide 102 and 108 in FIG. 1 and polypeptides 202 and 208 in FIG. 2). In yet another embodiment, an albumin-binding peptide can be attached to the C-terminus of Fc domain monomer (e.g., Fc domain monomers 114 and 116 in FIG. 1; Fc domain monomers 214 and 216 in FIG. 2) which is joined to the second Fc domain monomer in the polypeptide encoding the two Fc domain monomers linked in tandem series. Albumin-binding peptides can be fused genetically to Fc constructs or attached to Fc constructs through chemical means, e.g., chemical conjugation. If desired, a spacer can be inserted between the Fc construct and the albumin-binding peptide. Without being bound to a theory, it is expected that inclusion of an albumin-binding peptide in an Fc construct of the disclosure may lead to prolonged retention of the therapeutic protein through its binding to serum albumin.

VIII. Fc Constructs

In general, the disclosure features Fc constructs having Fc domains (e.g., an Fc construct having three Fc domains). These may have greater binding affinity and/or avidity than a single wild-type Fc domain for an Fc receptor, e.g., FcγRIIIa. The disclosure discloses methods of engineering amino acids at the interface of two interacting $C_H3$ antibody constant domains such that the two Fc domain monomers of an Fc domain selectively form a dimer with each other, thus preventing the formation of unwanted multimers or aggregates. An Fc construct includes an even number of Fc domain monomers, with each pair of Fc domain monomers forming an Fc domain. An Fc construct includes, at a minimum, one functional Fc domain formed from a dimer of two Fc domain monomers. In some embodiments, the Fc constructs described herein do not include an antigen-recognition region, e.g., a variable domain (e.g., $V_H$, $V_L$, a hypervariable region (HVR)) or a complementarity determining region (CDR). In some embodiments, the Fc constructs described herein include an antigen-recognition region, e.g., a variable domain (e.g., $V_H$, $V_L$, a HVR) or a CDR.

An Fc construct containing three Fc domains may form from four polypeptides (FIGS. 1 and 2). The first and second polypeptides (e.g., polypeptides 102 and 108 in FIG. 1; polypeptides 202 and 208 in FIG. 2) can be the same or different, as can the third and fourth polypeptides (e.g., polypeptides 114 and 116 in FIG. 1; polypeptides 214 and 216 in FIG. 2). In FIG. 1, the first and second polypeptides both encode two Fc domain monomers (e.g., Fc domain monomers 104, 106, 110, and 112) connected by way of a linker in tandem series, wherein one Fc domain monomer contains charged amino acid substitutions in the $C_H3$ antibody constant domain (e.g., Fc domain monomers 104 and 110) while the other Fc domain monomer contains a protuberance in the $C_H3$ antibody constant domain (e.g., Fc domain monomers 106 and 112). The third and fourth polypeptides both encode an Fc domain monomer with a cavity (e.g., Fc domain monomers 114 and 116). A stem homodimeric Fc domain may be formed by combining Fc domain monomers 104 and 110, each of which contains the same reverse charge mutations in its $C_H3$ antibody constant domain (e.g., each of Fc domain monomers 104 and 110 contains D399K and K409D. A first branch heterodimeric Fc domain may be formed by combining Fc domain monomers 106 and 114 (e.g., Fc domain monomer 106 contains engineered protuberances S354C and T366W, and Fc domain monomer 114 contains engineered cavities Y349C, T366S, L368A, and Y409V). A second heterodimeric Fc domain may be formed by combining Fc domain monomers 112 and 116 (e.g., Fc domain monomer 112 contains engineered protuberances S354C and T366W, and Fc domain monomer 116 contains engineered cavities Y349C, T366S, L368A, and Y409V).

In FIG. 2, the first and second polypeptides both encode two Fc domain monomers (e.g., Fc domain monomers 204, 206, 210, and 212) connected by way of a linker in tandem series, wherein one Fc domain monomer contains charged amino acid substitutions in the $C_H3$ antibody constant domain (e.g., Fc domain monomers 204 and 210) while the other Fc domain monomer contains a protuberance and charged amino acid substitutions in the $C_H3$ antibody constant domain (e.g., Fc domain monomers 206 and 212). The third and fourth polypeptides both encode an Fc domain monomer with a cavity and charged amino acid substitutions (e.g., Fc domain monomers 214 and 216). A stem homodimeric Fc domain may be formed by combining Fc domain monomers 204 and 210, each of which contains the same reverse charge mutations in its $C_H3$ antibody constant domain (e.g., each of Fc domain monomers 204 and 210 contains D399K and K409D. A first branch heterodimeric Fc domain may be formed by combining Fc domain monomers 206 and 214 (e.g., Fc domain monomer 206 contains engineered protuberances S354C and T366W and reverse charge mutation E357K, and Fc domain monomer 214 contains engineered cavities Y349C, T366S, L368A, and Y409V and reverse charge mutation K370D). A second heterodimeric Fc domain may be formed by combining Fc domain monomers 212 and 216 (e.g., Fc domain monomer 212 contains engineered protuberances S354C and T366W and reverse charge mutation E357K, and Fc domain monomer 216 contains engineered cavities Y349C, T366S, L368A, and Y409V and reverse charge mutation K370D).

In further embodiments, an Fc domain monomer containing (i) at least one reverse charge mutation and (ii) at least one engineered cavity or at least one engineered protuberance may selectively combine with another Fc domain monomer containing (i) at least one reverse charge mutation and (ii) at least one engineered protuberance or at least one engineered cavity to form an Fc domain. For example, an Fc domain monomer containing reversed charge mutation K370D and engineered cavities Y349C, T366S, L368A, and Y407V and another Fc domain monomer containing reversed charge mutation E357K and engineered protuberances S354C and T366W may selectively combine to form an Fc domain.

In some embodiments, in an Fc construct including: a) a first polypeptide having the formula A-L-B; wherein i) A includes a first Fc domain monomer; ii) L is a linker; and iii) B includes a second Fc domain monomer; b) a second polypeptide having the formula A'-L'-B'; wherein i) A' includes a third Fc domain monomer; ii) L' is a linker; and iii) B' includes a fourth Fc domain monomer; c) a third polypeptide that includes a fifth Fc domain monomer; and d) a fourth polypeptide that includes a sixth Fc domain monomer; wherein B and B' combine to form a first Fc domain, A and the fifth Fc domain monomer combine to form a second Fc domain, and A' and the sixth Fc domain monomer combine to form a third Fc domain, examples of some amino acid mutations that can be incorporated into the Fc domain monomers in the Fc construct are shown in Tables 3A-3D. In some embodiments, each of the first, second, third, and fourth polypeptides in the Fc construct lacks a C-terminal lysine. In some embodiments, the N-terminal Asp in each of the first, second, third, and fourth polypeptides in the Fc construct is mutated to Gln. In some embodiments, each of L and L' comprises, consists of, or consists essentially of the sequence GGGGGGGGGGGGGGGGGGGG (SEQ ID NO: 27).

TABLE 3A

| Fc domain monomer | Amino acid mutations (each column represents a set of mutations in an Fc construct having three Fc domains) | | | | | | | | |
|---|---|---|---|---|---|---|---|---|---|
| A and A' | Engineered protuberance reversed charge mutation(s) | S354C T366W E357K | S354C T366W E357R | S354C T366W E357K | S354C T366W E357R | S354C T366W E357K | S354C T366W E357R | S354C T366W E357K | S354C T366W E357R |

TABLE 3A-continued

| | | | | | | | | | |
|---|---|---|---|---|---|---|---|---|---|
| L and L' | | GGGGGGGGGGGGGGGGGGGG (SEQ ID NO: 27) | | | | | | | |
| B and B' | reversed charge mutation(s) | D399K K409D | D399K K409D | D399K K409D | D399K K409E | D399R K409D | D399K K409E | D399R K409E | D399R K409E |
| 5th and 6th Fc domain monomers | Engineered cavity | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V |
| | reversed charge mutation(s) | K370D | K370D | K370D | K370D | K370D | K370D | K370D | K370D |

| Fc domain monomer | Amino acid mutations (each column represents a set of mutations in an Fc construct having three Fc domains) | | | | | | | | |
|---|---|---|---|---|---|---|---|---|---|
| A and A' | | S354C T366W E357K | S354C T366W E357R | S354C T366W E357K | S354C T366W E357K | S354C T366W E357R | S354C T366W E357R | S354C T366W E357K | S354C T366W E357R |
| L and L' | | GGGGGGGGGGGGGGGGGGGG (SEQ ID NO: 27) | | | | | | | |
| B and B' | | D399K K409D | D399K K409D | D399K K409D | D399K K409E | D399R K409D | D399K K409E | D399R K409E | D399R K409E |
| 5th and 6th Fc domain monomers | | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E |

TABLE 3B

| Fc domain monomer | Amino acid mutations (each column represents a set of mutations in an Fc construct having three Fc domains) | | | | | | | | |
|---|---|---|---|---|---|---|---|---|---|
| A and A' | Engineered protuberance reversed charge mutation(s) | S354C T366W K370D | S354C T366W K370D | S354C T366W K370D | S354C T366W K370D | S354C T366W K370D | S354C T366W K370D | S354C T366W K370D | S354C T366W K370D |
| L and L' | | GGGGGGGGGGGGGGGGGGGG (SEQ ID NO: 27) | | | | | | | |
| B and B' | reversed charge mutation(s) | D399K K409D | D399K K409D | D399R K409D | D399K K409E | D399R K409D | D399K K409E | D399R K409E | D399R K409E |
| 5th and 6th Fc domain monomers | Engineered cavity | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V |
| | reversed charge mutation(s) | E357K | E357R | E357K | E357K | E357KR | E357K | E357K | E357R |

| Fc domain monomer | Amino acid mutations (each column represents a set of mutations in an Fc construct having three Fc domains) | | | | | | | | |
|---|---|---|---|---|---|---|---|---|---|
| A and A' | | S354C T366W K370E | S354C T366W K370E | S354C T366W K370E | S354C T366W K370E | S354C T366W K370E | S354C T366W K370E | S354C T366W K370E | S354C T366W K370E |
| L and L' | | GGGGGGGGGGGGGGGGGGGG (SEQ ID NO: 27) | | | | | | | |
| B and B' | | D399K K409D | D399K K409D | D399R K409D | D399K K409E | D399R K409D | D399K K409E | D399R K409E | D399R K409E |
| 5th and 6th Fc domain monomers | | Y349C T366S L368A Y407V E357K | Y349C T366S L368A Y407V E357R | Y349C T366S L368A Y407V E357K | Y349C T366S L368A Y407V E357R | Y349C T366S L368A Y407V E357R | Y349C T366S L368A Y407V E357K | Y349C T366S L368A Y407V E357K | Y349C T366S L368A Y407V E357R |

TABLE 3C

| Fc domain monomer | | Amino acid mutations (each column represents a set of mutations in an Fc construct having three Fc domains) | | | | | | | |
|---|---|---|---|---|---|---|---|---|---|
| A and A' | Engineered cavity | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V |
| | reversed charge mutation(s) | E357K | E357R | E357K | E357R | E357K | E357R | E357K | E357R |
| L and L' | | GGGGGGGGGGGGGGGGGGGG (SEQ ID NO: 27) | | | | | | | |
| B and B' | reversed charge mutation(s) | D399K K409D | D399K K409D | D399R K409D | D399R K409D | D399R K409E | D399K K409E | D399R K409E | D399R K409E |
| 5th and 6th Fc domain monomers | Engineered protuberance | S354C T366W | S354C T366W | S354C T366W | S354C T366W | S354C T366W | S354C T366W | S354C T366W | S354C T366W |
| | reversed charge mutation(s) | K370D | K370D | K370D | K370D | K370D | K370D | K370D | K370D |

| Fc domain monomer | Amino acid mutations (each column represents a set of mutations in an Fc construct having three Fc domains) | | | | | | | |
|---|---|---|---|---|---|---|---|---|
| A and A' | Y349C T366S L368A Y407V E357K | Y349C T366S L368A Y407V E357R | Y349C T366S L368A Y407V E357K | Y349C T366S L368A Y407V E357R | Y349C T366S L368A Y407V E357K | Y349C T366S L368A Y407V E357R | Y349C T366S L368A Y407V E357K | Y349C T366S L368A Y407V E357R |
| L and L' | GGGGGGGGGGGGGGGGGGGG (SEQ ID NO: 27) | | | | | | | |
| B and B' | D399K K409D | D399K K409D | D399R K409D | D399R K409E | D399R K409E | D399K K409E | D399R K409E | D399R K409E |
| 5th and 6th Fc domain monomers | S354C T366W K370E | S354C T366W K370E | S354C T366W K370E | S354C T366W K370E | S354C T366W K370E | S354C T366W K370E | S354C T366W K370E | S354C T366W K370E |

TABLE 3D

| Fc domain monomer | | Amino acid mutations (each column represents a set of mutations in an Fc construct having three Fc domains) | | | | | | | |
|---|---|---|---|---|---|---|---|---|---|
| A and A' | Engineered cavity | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V |
| | reversed charge mutation(s) | K370D | K370D | K370D | K370D | K370D | K370D | K370D | K370D |
| L and L' | | GGGGGGGGGGGGGGGGGGGG (SEQ ID NO: 27) | | | | | | | |
| B and B' | reversed charge mutation(s) | D399K K409D | D399K K409D | D399R K409D | D399R K409E | D399R K409D | D399K K409E | D399R K409E | D399R K409E |
| 5th and 6th Fc domain monomers | Engineered protuberance | S354C T366W | S354C T366W | S354C T366W | S354C T366W | S354C T366W | S354C T366W | S354C T366W | S354C T366W |
| | reversed charge mutation(s) | E357K | E357R | E357K | E357R | E357K | E357R | E357K | E357R |

| Fc domain monomer | Amino acid mutations (each column represents a set of mutations in an Fc construct having three Fc domains) | | | | | | | |
|---|---|---|---|---|---|---|---|---|
| A and A' | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E |
| L and L' | GGGGGGGGGGGGGGGGGGGG (SEQ ID NO: 27) | | | | | | | |
| B and B' | D399K K409D | D399K K409D | D399R K409D | D399R K409E | D399R K409D | D399K K409E | D399R K409E | D399R K409E |
| 5th and 6th Fc domain monomers | S354C T366W E357K | S354C T366W E357R | S354C T366W E357K | S354C T366W E357R | S354C T366W E357K | S354C T366W E357R | S354C T366W E357K | S354C T366W E357R |

Figure 13:
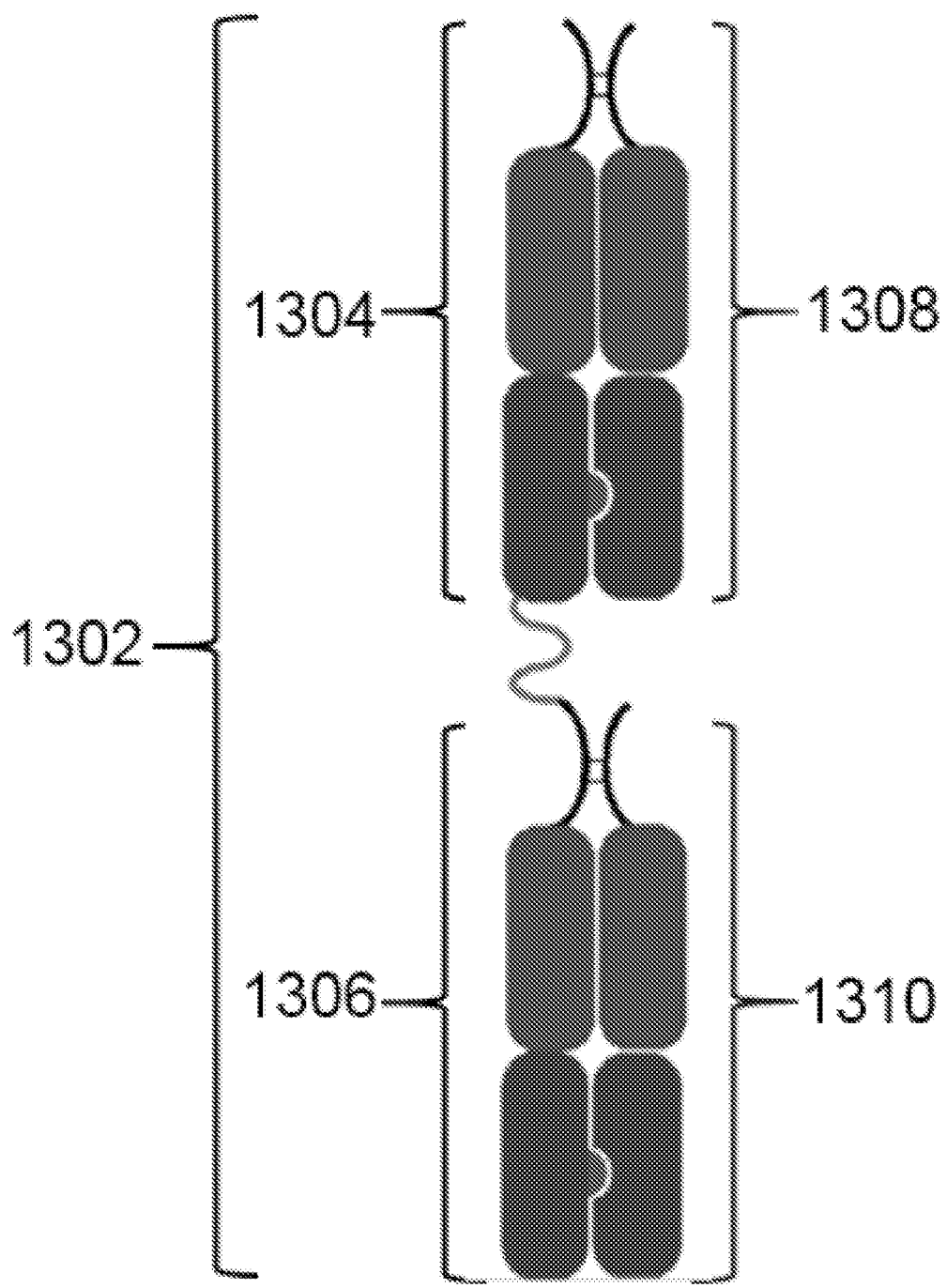
FIG. 13 is an illustration of an Fc construct containing two Fc domains formed from three polypeptides.

In some embodiments, an Fc construct contains two Fc domains formed from three polypeptides. The first polypeptide contains two Fc domain monomers joined in tandem series joined by way of a linker (e.g., a glycine spacer; SEQ ID NOs: 26 and 27), and the second and third polypeptides contain one Fc domain monomer. The second and third polypeptides may be the same polypeptide or may be different polypeptides. FIG. 13 depicts an example of such an Fc construct. The first polypeptide (1302) contains two Fc domain monomers (1304 and 1306) joined in tandem series by way of a linker (e.g., a glycine spacer; SEQ ID NOs: 26 and 27). Both Fc domain monomers 1304 and 1306 contain engineered protuberances in the $C_H3$ antibody constant domains. The second and third polypeptides (1308 and 1310) each contain one Fc domain monomer having engineered cavities in the $C_H3$ antibody constant domain. One of the Fc domain monomers (1304) in the first polypeptide forms a first heterodimeric Fc domain with the second polypeptide (1308), while the other Fc domain monomer (1306) in the first polypeptide forms a second heterodimeric Fc domain with the third polypeptide (1310). The second and third polypeptides are not attached or linked to each other. The engineered protuberance-into-cavity $C_H3$-$C_H3$ interface favors the formation of heterodimers of Fc domain monomers and prevents the uncontrolled formation of unwanted multimers. In some embodiments, each of the Fc domain monomers may further contain reverse charge mutations to promote heterodimerization. For example, Fc domain monomer 1304 having engineered protuberances and reverse charge mutations (e.g., E357K) may favorably form a heterodimeric Fc domain with Fc domain monomer 1308 having engineered cavities and reverse charge mutations (e.g., K370D).

Figure 14:
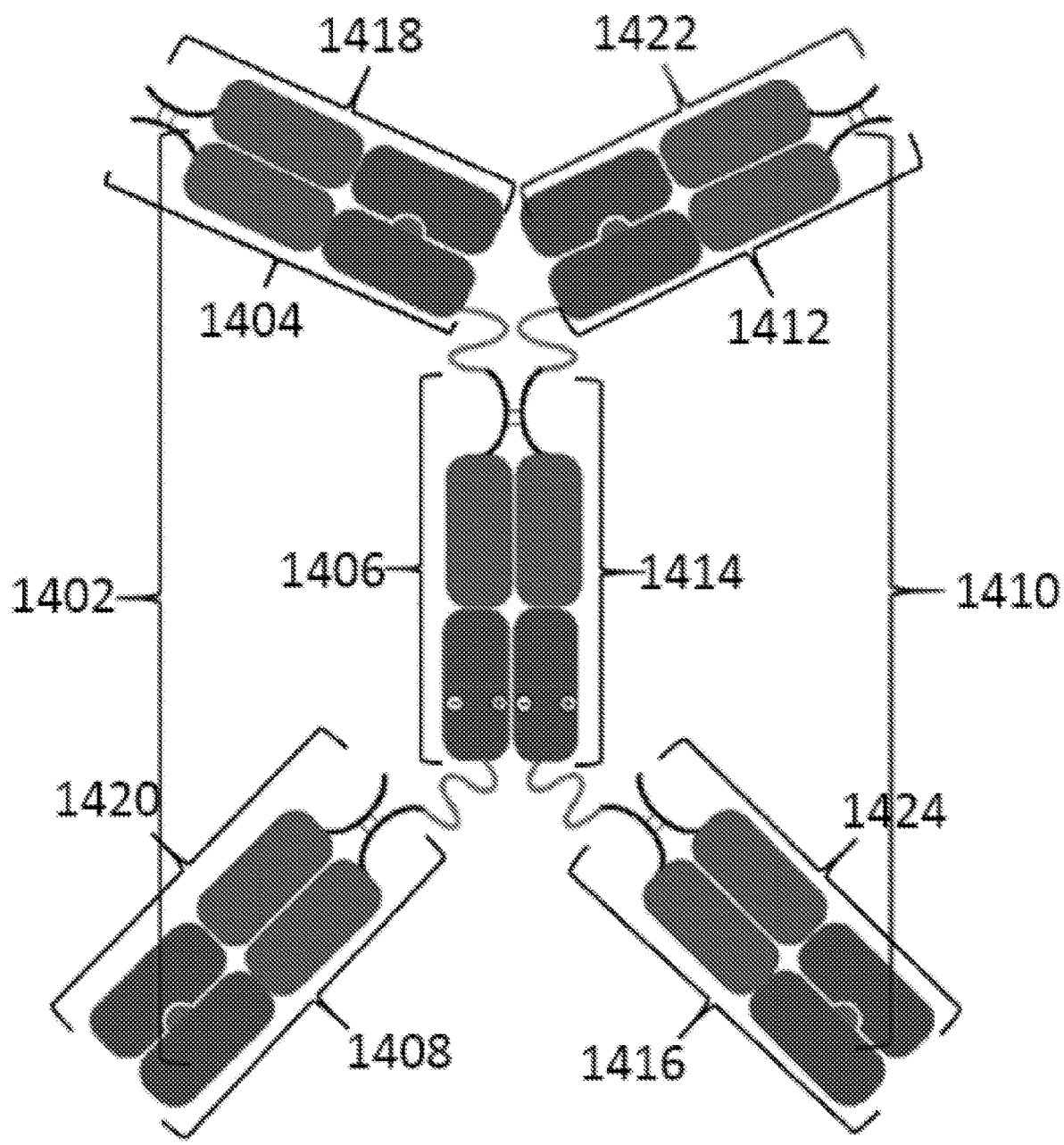
FIG. 14 is an illustration of an Fc construct containing five Fc domains formed from six polypeptides (Fc5X).
Figure 15:
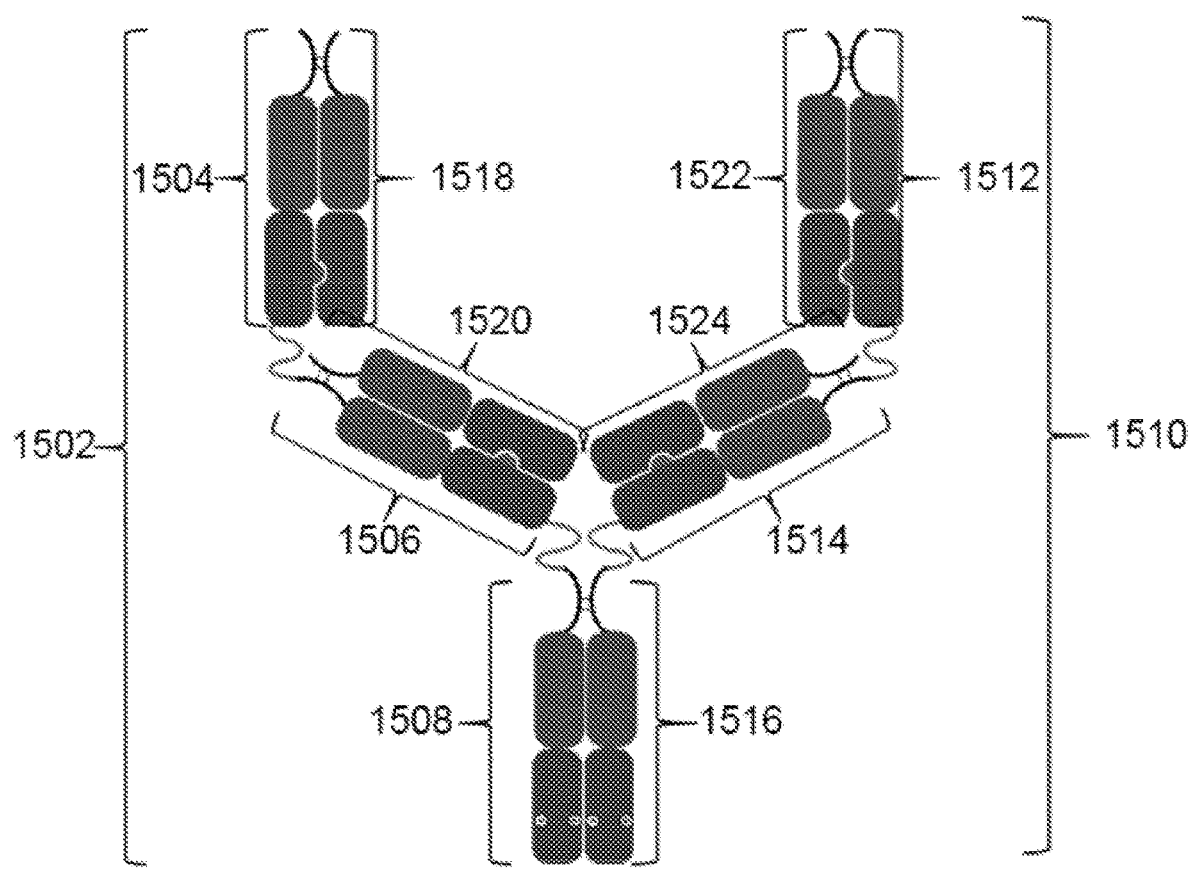
FIG. 15 is an illustration of an Fc construct containing five Fc domains formed from six polypeptides (Fc5Y).

In yet other embodiments, Fc constructs can contain five Fc domains formed from six polypeptides. Two examples are depicted in FIGS. 14 and 15. While these depicted Fc constructs are comprised of six polypeptides, four of the polypeptides can be encoded by the same nucleic acid, and the remaining two polypeptides can also be encoded by the same nucleic acid. As a result, these Fc constructs can be produced by the expression of two nucleic acids in a suitable host cell.

FIG. 14 is an illustration of an Fc construct containing five Fc domains formed from six polypeptides. The first and second polypeptides (1402 and 1410) each contain three Fc domain monomers (1404, 1406, 1408, and 1412, 1414, 1416, respectively) joined in a tandem series by way of a linker (e.g., a glycine spacer; SEQ ID NOs: 26 and 27). Specifically, in polypeptide 1402 or 1410, a first protuberance-containing Fc domain monomer (1404 or 1412) is connected to a second Fc domain monomer containing different charged amino acids at the $C_H3$-$C_H3$ interface (1406 or 1414) than the wild-type sequence, which is connected to a third protuberance-containing Fc domain monomer (1408 or 1416). Fc domain monomers 1406 and 1414 may each contain the same reverse charge mutations (e.g., D399K/K409D) that promote formation of a homodimeric Fc domain. The third through sixth polypeptides (1418, 1420, 1422, and 1424) each contain a cavity-containing Fc domain monomer and form a heterodimeric Fc domain with each of Fc domain monomers 1404, 1408, 1412 and 1416, respectively. In some embodiments, each of the Fc domain monomers 1404, 1408, 1412, 1416, 1418, 1420, 1422, and 1424 may further contain reverse charge mutations to promote heterodimerization. For example, Fc domain monomer 1408 having engineered protuberances and reverse charge mutations (e.g., E357K) may favorably form a heterodimeric Fc domain with Fc domain monomer 1420 having engineered cavities and reverse charge mutations (e.g., K370D).

FIG. 15 is an illustration of an Fc construct containing five Fc domains formed from six polypeptides. The first and second polypeptides (1502 and 1510) each contain three Fc domain monomers (1504, 1506, 1508, and 1512, 1514, 1516, respectively) joined in a tandem series by way of a linker (e.g., a glycine spacer; SEQ ID NOs: 26 and 27). Specifically, in polypeptide 1502 or 1510, a first protuberance-containing Fc domain monomer (1504 or 1512) is connected to a second protuberance-containing Fc domain monomer (1506 or 1514), which is connected to a third Fc domain monomer containing different charged amino acids at the $C_H3$-$C_H3$ interface (1508 or 1516) than the wild-type sequence. Fc domain monomers 1508 and 1516 may each contain the same reverse charge mutations (e.g., D399K/K409D) that promote formation of a homodimeric Fc domain. The third through sixth polypeptides (1518, 1520, 1522, and 1524) each contain a cavity-containing Fc domain monomer and form a heterodimeric Fc domain with each of Fc domain monomers 1504, 1506, 1512 and 1514, respectively. In some embodiments, each of the Fc domain monomers 1504, 1506, 1512, 1514, 1518, 1520, 1522, and 1524 may further contain reverse charge mutations to promote heterodimerization. For example, Fc domain monomer 1504 having engineered protuberances and reverse charge mutations (e.g., E357K) may favorably form a heterodimeric Fc domain with Fc domain monomer 1518 having engineered cavities and reverse charge mutations (e.g., K370D).

Figure 16:
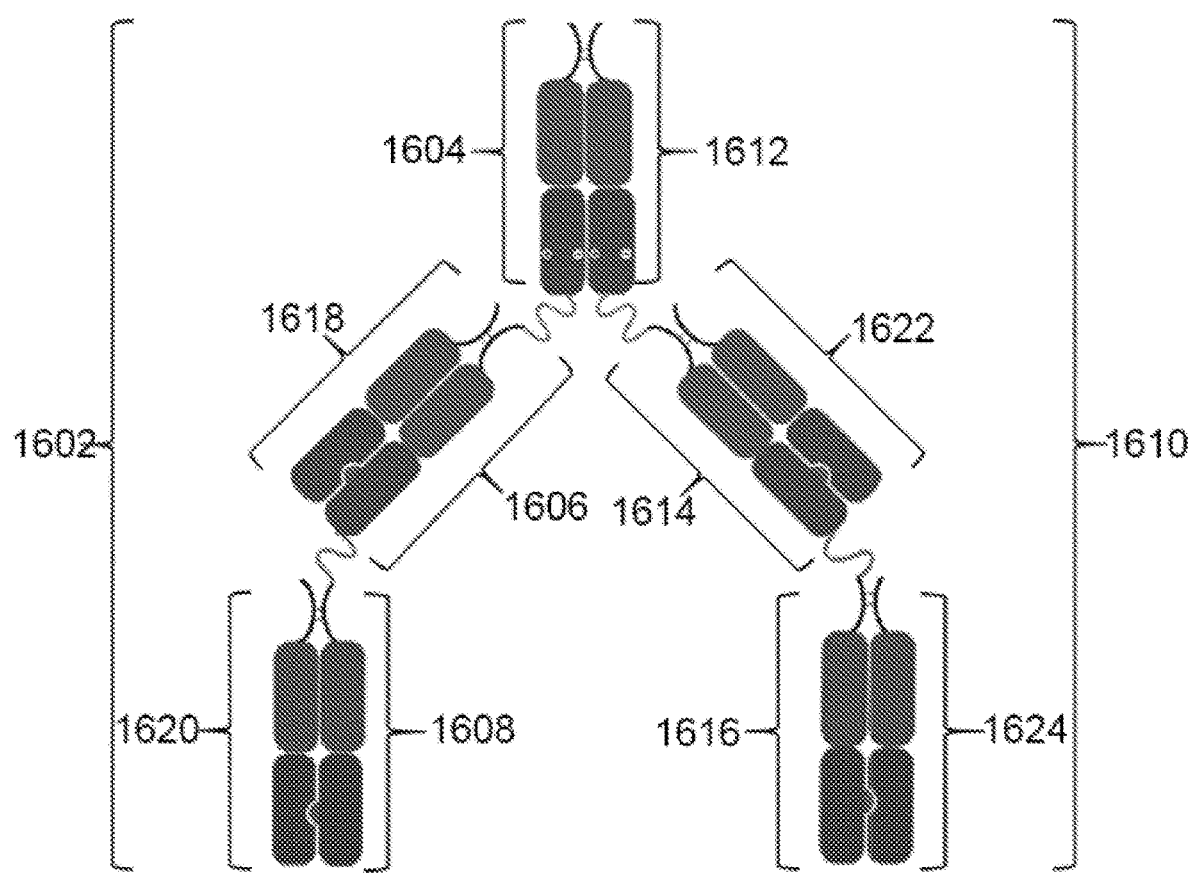
FIG. 16 is an illustration of an Fc construct containing five Fc domains formed from six polypeptides (Fc5Y-invert).

FIG. 16 is an illustration of another Fc construct containing five Fc domains formed from six polypeptides. The first and second polypeptides (1602 and 1610) each contain three Fc domain monomers (1604, 1606, 1608, and 1612, 1614, 1616, respectively) joined in a tandem series by way of a linker (e.g., a glycine spacer; SEQ ID NOs: 26 and 27). Specifically, in polypeptide 1602 or 1610, a first Fc domain monomer containing different charged amino acids at the $C_H3$-$C_H3$ interface (1604 or 1612) is connected to a second protuberance-containing Fc domain monomer (1606 or 1614), which is connected to a third protuberance-containing Fc domain monomer (1608 or 1616) than the wild-type sequence. Fc domain monomers 1604 and 1612 may each contain the same reverse charge mutations (e.g., D399K/K409D) that promote formation of a homodimeric Fc domain. The third through sixth polypeptides (1618, 1620, 1622, and 1624) each contain a cavity-containing Fc domain monomer and form a heterodimeric Fc domain with each of Fc domain monomers 1606, 1608, 1614 and 1616, respectively. In some embodiments, each of the Fc domain monomers 1606, 1608, 1614, 1616, 1618, 1620, 1622, and 1624 may further contain reverse charge mutations to promote heterodimerization. For example, Fc domain monomer 1608 having engineered protuberances and reverse charge mutations (e.g., E357K) may favorably form a heterodimeric Fc domain with Fc domain monomer 1620 having engineered cavities and reverse charge mutations (e.g., K370D).

Figure 17:
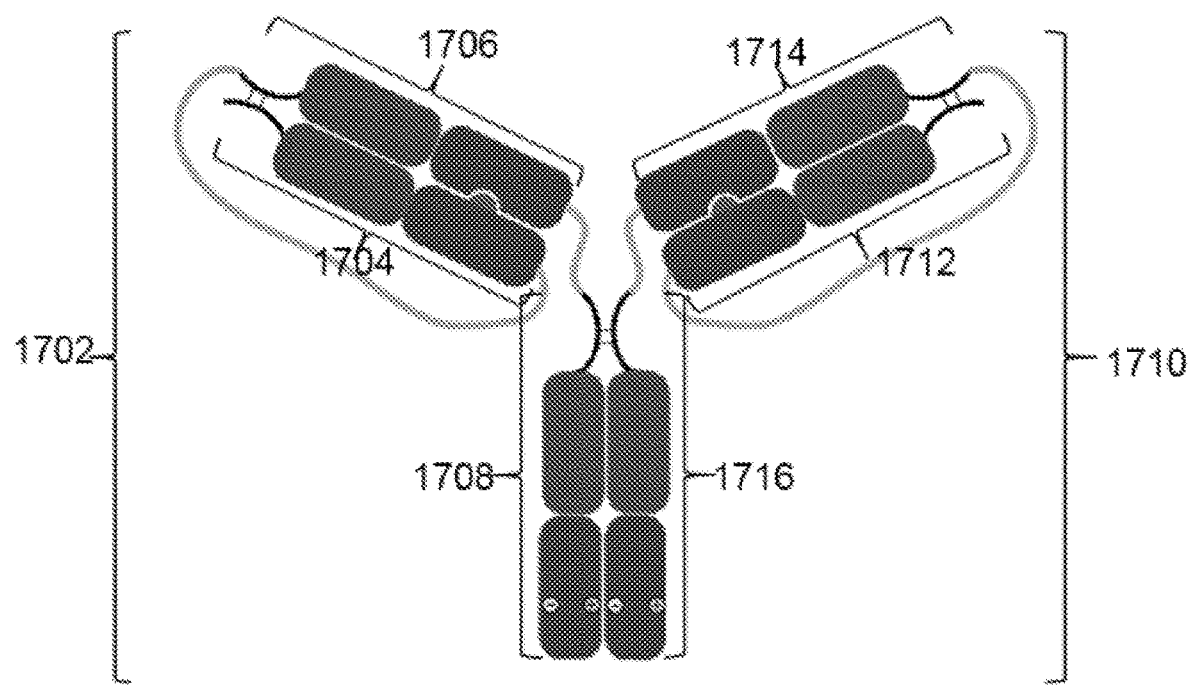
FIG. 17 is an illustration of an Fc construct containing three Fc domains formed from two polypeptides.

In another embodiment, an Fc construct containing two or more Fc domains can be formed from two polypeptides having the same primary sequence. Such a construct can be formed from expression of a single polypeptide sequence in a host cell. An example is depicted in FIG. 17. In this example, a single nucleic acid is sufficient to encode an Fc construct containing three Fc domains. Two Fc domain monomers that are part of the same polypeptide are permitted to form a heterodimeric Fc domain by the inclusion of a flexible linker of a sufficient length and flexibility. This same polypeptide also contains a third Fc domain monomer joined by way of a flexible linker (e.g., a glycine spacer; SEQ ID NOs: 26 and 27). This third Fc domain monomer (1708) is capable of joining to another Fc domain monomer (1716) to form a homodimeric Fc domain and to produce the Y-shaped Fc construct depicted in FIG. 17. Formation of Fc domains can be controlled through the use of dimerization selectivity modules, as is also depicted in FIG. 17. In some embodiments, each of the Fc domain monomers 1704, 1706, 1712, and 1714 may further contain reverse charge mutations to promote heterodimerization. For example, Fc domain monomer 1704 having engineered protuberances and reverse charge mutations (e.g., E357K) may favorably form a heterodimeric Fc domain with Fc domain monomer 1706 having engineered cavities and reverse charge mutations (e.g., K370D).

In some embodiments, one or more Fc polypeptides in an Fc construct (e.g., Fc construct 1-3 in FIG. 1; Fc construct 4 in FIG. 2) lack a C-terminal lysine residue. In some embodiments, all of the Fc polypeptides in an Fc construct lack a C-terminal lysine residue. In some embodiments, the absence of a C-terminal lysine in one or more Fc polypeptides in an Fc construct may improve the homogeneity of a population of an Fc construct (e.g., an Fc construct having three Fc domains), e.g., a population of an Fc construct having three Fc domains that is substantially homogeneous (see Example 8). In one example, the C-terminal lysine residue in an Fc polypeptide having the sequence of any one of SEQ ID NOs: 43 and 44 (see Example 1, Table 6) may be removed to generate a corresponding Fc polypeptide that does not contain a C-terminal lysine residue.

In some embodiments, one or more Fc polypeptides in an Fc construct include the S267E/L328F mutations. In some cases, the Fc construct is Fc construct 4 and the construct includes the S267E/L328F mutations. This mutation increases the Fc construct's binding affinity to FcγRIIb.

In some embodiments, an Fc domain monomer in an Fc construct described herein (e.g., an Fc construct having three Fc domains) may have a sequence that is at least 95% identical (e.g., at least 97%, 99%, or 99.5% identical) to the sequence of a wild-type Fc domain monomer (e.g., SEQ ID NO: 42). In some embodiments, an Fc domain monomer in an Fc construct described herein (e.g., an Fc construct having three Fc domains) may have a sequence that is at least 95% identical (e.g., at least 97%, 99%, or 99.5% identical) to the sequence of any one of SEQ ID NOs: 44, 46, 48, and 50-53. In certain embodiments, an Fc domain monomer in the Fc construct may have a sequence that is at least 95% identical (e.g., at least 97%, 99%, or 99.5% identical) to the sequence of SEQ ID NO: 48, 52, and 53.

In some embodiments, a polypeptide having two Fc domain monomers in an Fc construct described herein (e.g., polypeptides 102 and 108 in FIG. 1; polypeptides 202 and 208 in FIG. 2) may comprise, consist of, or consist essentially of a sequence that is at least 95% identical (e.g., at least 97%, 99%, or 99.5% identical) to the sequence of any one of SEQ ID NOs: 43, 45, 47, and 49 (see Example 1, Table 6). In certain embodiments, a polypeptide having two Fc domain monomers in an Fc construct described herein may comprise, consist of, or consist essentially of a sequence that is at least 95% identical (e.g., at least 97%, 99%, or 99.5% identical) to the sequence of SEQ ID NOs: 49. In some embodiments, the amino acid mutations in a polypeptide having two Fc domain monomers in an Fc construct described herein (e.g., polypeptides 102 and 108 in FIG. 1; polypeptides 202 and 208 in FIG. 2) occur only in the Fc domain monomers (e.g., Fc domain monomers 104, 106, 110, and 112 in FIG. 1; Fc domain monomers 204, 206, 210, and 212 in FIG. 2) and do not occur in the spacer. For example, in the polypeptides shown in Table 8, additional amino acid mutations may be made in the Fc domain monomers comprising, consisting of, or consisting essentially of the sequences of SEQ ID NOs: 50-53 while the spacers having the sequences of SEQ ID NOs: 18, 26, and 27 do not change.

In some embodiments, the N-terminal Asp in one or more of the first, second, third and fourth polypeptides in an Fc construct described herein (e.g., polypeptides 102, 108, 114, and 116 in FIG. 1; 202, 208, 214, and 216 in FIG. 2) may be mutated to Gln. In some embodiments, the N-terminal Asp in each of the first, second, third, and fourth polypeptides in an Fc construct described herein is mutated to Gln. In other embodiments, an Fc construct described herein (e.g., an Fc construct having three Fc domains) may include one or more Fc domain monomers having N-terminal Asp be mutated to Gln. In some embodiments, the mutation of N-terminal Asp to Gln in one or more of the first, second, third and fourth polypeptides in an Fc construct described herein may improve the homogeneity of a population of an Fc construct (e.g., an Fc construct having three Fc domains), e.g., a population of an Fc construct having three Fc domains that is substantially homogeneous. For example, Table 4 shows amino acid sequences of first, second, third, and fourth polypeptides that have N-terminal Asp mutated to Gln in an Fc construct having three Fc domains.

TABLE 4

| | Fc construct with N-terminal Asp mutated to Gln in all four polypeptides |
|---|---|
| First and second polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVYTLPPCRDELTKNQVSLWCLVKGFYPSDIAVEWESNGQPENN YKTTPPVLDSDGSFFLYSKLTVDKSRWQQGNVFSCSVMHEALHNHYTQKSLSLSPG KSGGGSGGGSGGGSGGGSGGGDKTHTCPPCPAPELLGGPSVFLFPPKPKDTLMIS RTPEVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKNQVSLTC LVKGFYPSDIAVEWESNGQPENNYKTTPPVLKSDGSFFLYSDLTVDKSRWQQGNVF SCSVMHEALHNHYTQKSLSLSPGK (SEQ ID NO: 54) |
| Third and fourth polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVCTLPPSRDELTKNQVSLSCAVKGFYPSDIAVEWESNGQPENNY KTTPPVLDSDGSFFLVSKLTVDKSRWQQGNVFSCSVMHEALHNHYTQKSLSLSPGK (SEQ ID NO: 55) |

TABLE 4-continued

Fc construct with N-terminal Asp mutated to Gln in all four polypeptides

| | |
|---|---|
| First and second polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVYTLPPCRDELTKNQVSLWCLVKGFYPSDIAVEWESNGQPENN YKTTPPVLDSDGSFFLYSKLTVDKSRWQQGNVFSCSVMHEALHNHYTQKSLSLSPG KSGGGSGGGSGGGSGGGSGGGDKTHTCPPCPAPELLGGPSVFLFPPKPKDTLMIS RTPEVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKNQVSLTC LVKGFYPSDIAVEWESNGQPENNYKTTPPVLKSDGSFFLYSDLTVDKSRWQQGNVF SCSVMHEALHNHYTQKSLSLSPG (SEQ ID NO: 56) |
| Third and fourth polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVCTLPPSRDELTKNQVSLSCAVKGFYPSDIAVEWESNGQPENNY KTTPPVLDSDGSFFLVSKLTVDKSRWQQGNVFSCSVMHEALHNHYTQKSLSLSPG (SEQ ID NO: 57) |
| First and second polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVYTLPPCRDELTKNQVSLWCLVKGFYPSDIAVEWESNGQPENN YKTTPPVLDSDGSFFLYSKLTVDKSRWQQGNVFSCSVMHEALHNHYTQKSLSLSPG KGGGGGGGGGGGGGGGDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCLVKGFY PSDIAVEWESNGQPENNYKTTPPVLKSDGSFFLYSDLTVDKSRWQQGNVFSCSVMH EALHNHYTQKSLSLSPG (SEQ ID NO: 58) |
| Third and fourth polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVCTLPPSRDELTKNQVSLSCAVDGFYPSDIAVEWESNGQPENNY KTTPPVLDSDGSFFLVSKLTVDKSRWQQGNVFSCSVMHEALHNHYTQKSLSLSPG (SEQ ID NO: 59) |
| First and second polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVYTLPPCRDLTKNQVSLWCLVKGFYPSDIAVEWESNGQPENN YKTTPPVLDSDGSFFLYSKLTVDKSRWQQGNVFSCSVMHEALHNHYTQKSLSLSPG KGGGGGGGGGGGGGGGGGGDKTHTCPPCPAPELLGGPSVFLFPPKPKDTLMI SRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDELTKNQVSLT CLVKGFYPSDIAVEWESNGQPENNYKTTPPVLKSDGSFFLYSDLTVDKSRWQQGNV FSCSVMHEALHNHYTQKSLSLSPG (SEQ ID NO: 60) |
| Third and fourth polypeptides | QKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVCTLPPSRDELTKNQVSLSCAVDGFYPSDIAVEWESNGQPENNY KTTPPVLDSDGSFFLVSKLTVDKSRWQQGNVFSCSVMHEALHNHYTQKSLSLSPG (SEQ ID NO: 59) |

IX. Host Cells and Protein Production

In the present disclosure, a host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (transformation, transfection, electroporation, calcium phosphate precipitation, direct microinjection, etc.). Host cells can be of mammalian, bacterial, fungal, or insect origin. Mammalian host cells include, but are not limited to, CHO (or CHO-derived cell strains, e.g., CHO-K1, CHO-DXB11 CHO-DG44), murine host cells (e.g., NSO, Sp2/0), VERY, HEK (e.g., HEK293), BHK, HeLa, COS, MDCK, 293, 3T3, W138, BT483, Hs578T, HTB2, BT20 and T47D, CRL7O3O and HsS78Bst cells. Host cells can also be chosen that modulate the expression of the protein constructs, or modify and process the protein product in the specific fashion desired. Different host cells have characteristic and specific mechanisms for the post-translational processing and modification of protein products. Appropriate cell lines or host systems can be chosen to ensure the correct modification and processing of the protein expressed.

For expression and secretion of protein products from their corresponding DNA plasmid constructs, host cells may be transfected or transformed with DNA controlled by appropriate expression control elements known in the art, including promoter, enhancer, sequences, transcription terminators, polyadenylation sites, and selectable markers. Methods for expression of therapeutic proteins are known in the art. See, for example, Paulina Balbas, Argelia Lorence (eds.) *Recombinant Gene Expression: Reviews and Protocols* (*Methods in Molecular Biology*), Humana Press; 2nd ed. 2004 edition (Jul. 20, 2004); Vladimir Voynov and Justin A. Caravella (eds.) *Therapeutic Proteins: Methods and Protocols* (*Methods in Molecular Biology*) Humana Press; 2nd ed. 2012 edition (Jun. 28, 2012).

X. Purification

An Fc construct can be purified by any method known in the art of protein purification, for example, by chromatography (e.g., ion exchange, affinity (e.g., Protein A affinity), and size-exclusion column chromatography), centrifugation, differential solubility, or by any other standard technique for the purification of proteins. For example, an Fc construct can be isolated and purified by appropriately selecting and combining affinity columns such as Protein A column with chromatography columns, filtration, ultra filtration, salting-out and dialysis procedures (see, e.g., *Process Scale Purification of Antibodies*, Uwe Gottschalk (ed.) John Wiley & Sons, Inc., 2009; and Subramanian (ed.) *Antibodies—Volume I—Production and Purification*, Kluwer Academic/Plenum Publishers, New York (2004)).

In some instances, an Fc construct can be conjugated to one or more purification peptides to facilitate purification and isolation of the Fc construct from, e.g., a whole cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be joined to an Fc construct include, but are not limited to, a hexa-histidine peptide, a FLAG peptide, a myc peptide, and a hemagglutinin (HA) peptide. A hexa-histidine peptide (HHHHHH (SEQ ID NO: 38)) binds to nickel-functionalized agarose affinity column with micromolar affinity. In some embodiments, a FLAG peptide includes the sequence DYKDDDDK (SEQ ID NO: 39). In some embodiments, a FLAG peptide includes integer multiples of the sequence DYKDDDDK in tandem series, e.g., 3×DYKDDDDK. In some embodiments, a myc peptide includes the sequence EQKLISEEDL (SEQ ID NO: 40). In some embodiments, a myc peptide includes integer multiples of the sequence EQKLISEEDL in tandem series, e.g., 3×EQKLISEEDL. In some embodiments, an HA peptide includes the sequence YPYDVPDYA (SEQ ID NO: 41). In some embodiments, an HA peptide includes integer multiples of the sequence YPYDVPDYA in tandem series, e.g., 3×YPYDVPDYA. Antibodies that specifically recognize and bind to the FLAG, myc, or HA purification peptide are well-known in the art and often commercially available. A solid support (e.g., a matrix, a resin, or agarose beads) functionalized with these antibodies may be used to purify an Fc construct that includes a FLAG, myc, or HA peptide.

For the Fc constructs, Protein A column chromatography may be employed as a purification process. Protein A ligands interact with Fc constructs through the Fc region, making Protein A chromatography a highly selective capture process that is able to remove most of the host cell proteins. In the present disclosure, Fc constructs may be purified using Protein A column chromatography as described in Example 2.

XI. Pharmaceutical Compositions/Preparations

The disclosure features pharmaceutical compositions that include one or more Fc constructs described herein. In one embodiment, a pharmaceutical composition includes a substantially homogenous population of Fc constructs. In various examples, the pharmaceutical composition includes a substantially homogenous population of any one of Fc constructs 1-4.

A therapeutic protein construct, e.g., an Fc construct described herein (e.g., an Fc construct having three Fc domains), of the present disclosure can be incorporated into a pharmaceutical composition. Pharmaceutical compositions including therapeutic proteins can be formulated by methods know to those skilled in the art. The pharmaceutical composition can be administered parenterally in the form of an injectable formulation including a sterile solution or suspension in water or another pharmaceutically acceptable liquid. For example, the pharmaceutical composition can be formulated by suitably combining the Fc construct with pharmaceutically acceptable vehicles or media, such as sterile water for injection (WFI), physiological saline, emulsifier, suspension agent, surfactant, stabilizer, diluent, binder, excipient, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™ HCO-50, and the like commonly known in the art. Formulation methods for therapeutic protein products are known in the art, see e.g., Banga (ed.) *Therapeutic Peptides and Proteins: Formulation, Processing and Delivery Systems* (2d ed.) Taylor & Francis Group, CRC Press (2006).

XII. Dosage

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, oral dosage forms such as ingestible solutions, drug release capsules, and the like. The appropriate dosage for the individual subject depends on the therapeutic objectives, the route of administration, and the condition of the patient. Generally, recombinant proteins are dosed at 1-200 mg/kg, e.g., 1-100 mg/kg, e.g., 20-100 mg/kg. Accordingly, it will be necessary for a healthcare provider to tailor and titer the dosage and modify the route of administration as required to obtain the optimal therapeutic effect.

XIII. Indications

The pharmaceutical compositions of the disclosure (e.g., those containing Fc constructs having 2, 3, or 4 Fc domains) are useful to reduce inflammation in a subject, to promote clearance of autoantibodies in a subject, to suppress antigen presentation in a subject, to reduce the immune response, e.g., to block immune complex-based activation of the immune response in a subject, and to treat immunological and inflammatory conditions or diseases in a subject. Exemplary conditions and diseases include rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; clearance of anti-allo in transplant, anti-self in GVHD, anti-replacement, IgG therapeutics, IgG paraproteins; dermatomyositis; Goodpasture's Syndrome; organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease; idiopathic thrombocytopenia purpura; Myasthenia Gravis, neuromyelitis optica; pemphigus and other autoimmune blistering disorders; Sjogren's Syndrome; autoimmune cytopenias and other disorders mediated through antibody-dependent phagocytosis; other FcR-dependent inflammatory syndromes e.g., synovitis, dermatomyositis, systemic vasculitis, glomerulitis, and vasculitis.

In some embodiments, the pharmaceutical compositions of the disclosure containing Fc constructs having 5-10 Fc domains are also useful, e.g., to induce immune cell activation of the immune response in a subject, to increase phagocytosis of a target cell (i.e., a cancer cell or an infected cell) in a subject, and to treat diseases such as cancers and infections in a subject. Fc constructs and homogenous pharmaceutical compositions of the disclosure may bind to activating Fcγ receptors (e.g., FcγRI, FcγRIIa, FcγRIIc, FcγRIIIa, and FcγRIIIb) to induce an immune response. Fc constructs and homogenous pharmaceutical compositions of the disclosure may activate Syk phosphorylation and calcium flux from primary THP-1 monocytes. Activated monocytes and their differentiated macrophages have the ability to phagocytose or kill target cells. The disclosure therefore provides methods of treatment that may be used to treat subjects who are suffering from diseases and disorders such as cancers and infections. In some embodiments, Fc constructs and homogenous pharmaceutical compositions described herein may be administered to a subject in a therapeutically effective amount to phagocytose or kill cancer cells or infected cells in the subject.

Cancers that are amenable to treatment according to the methods of the disclosure include, but are not limited to, bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, squamous cell carcinoma, anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor cancer, and soft tissue tumor cancer.

Infections that are amenable to treatment according to the methods of the disclosure include, but are not limited to, a bacterial infection, a viral infection, a fungal infection, a helmintic infection, and a protozoal infection.

Examples of infection-causing bacteria are well-known in the art and include, but are not limited to, bacteria in the genus *Streptococcus* (e.g., *Streptococcus pyogenes*), bacteria in the genus *Escherichia* (e.g., *Escherichia coli*), bacteria in the genus *Vibrio* (e.g., *Vibrio cholerae*), bacteria in the genus Enteritis (e.g., Enteritis *salmonella*), and bacteria in the genus *Salmonella* (e.g., *Salmonella typhi*). Examples of infection-causing viruses are well-known in the art and include, but are not limited to, viruses in the family Retroviridae (e.g., human immunodeficiency virus (HIV)), viruses in the family Adenoviridae (e.g., adenovirus), viruses in the family Herpesviridae (e.g., herpes simplex virus types 1 and 2), viruses in the family Papillomaviridae (e.g., human papillomavirus (HPV)), viruses in the family Poxviridae (e.g., smallpox), viruses in the family Picornaviridae (e.g., hepatitis A virus, poliovirus, rhinovirus), viruses in the family Hepadnaviridae (e.g., hepatitis B virus), viruses in the family Flaviviridae virus (e.g., hepatitus C virus, yellow fever virus, West Nile virus), viruses in the family Togaviridae (e.g., rubella virus), viruses in the family Orthomyxoviridae (e.g., influenza virus), viruses in the family Filoviridae (e.g., ebola virus, marburg virus), and viruses in the family Paramyxoviridae (e.g., measles virus, mumps virus). Examples of infection-causing fungi are well-known in the art and include, but are not limited to, fungi in the genus *Aspergillus* (e.g., *Aspergillus fumigatus, A. flavus, A. terreus. A. niger, A. candidus, A. clavatus, A. ochraceus*), fungi in the genus *Candida* (e.g., *Candida albicans, C. parapsilosis, C. glabrata, C. guilliermondii, C. krusei, C. lusitaniae, C. tropicalis*), fungi in the genus *Cryptococcus* (e.g., *Cryptococcus neoformans*), and fungi in the genus *Fusarium* (e.g., *Fusarium solani, F. verticillioides, F. oxysporum*). Examples of helminths include, but are not limited to, tapeworms (cestodes), roundworms (nematodes), flukes (trematodes), and monogeneans.

Examples of protozoans include, but are not limited to, protozoans in the genus *Entamoeba* (e.g., *Entamoeba histolytica*), protozoans in the genus *Plasmodium* (e.g., *Plasmodium falciparum, P. malariae*), protozoans in the genus *Giardia* (e.g., *Giardia lamblia*), and protozoans in the genus *Trypanosoma* (e.g., *Trypanosoma brucei*).

EXAMPLES

Example 1. Fc Constructs Design

Desirably, Fc constructs are designed to increase folding efficiencies, to minimize uncontrolled association of subunits, which may create unwanted high molecular weight oligomers and multimers, and to generate compositions that are substantially homogenous. With these goals in mind, we designed four Fc constructs (FIGS. 1 and 2), each including a long polypeptide including two Fc domain monomers separated by a spacer (polypeptides 102 and 108 in FIG. 1 and polypeptides 202 and 208 in FIG. 2) and a short polypeptide including a single Fc domain monomer (polypeptides 114 and 116 in FIG. 1 and polypeptides 214 and 216 in FIG. 2). Each is based on the IgG1 Fc sequence, with the inclusion of engineered cavity, engineered protuberance, and/or electrostatic steering modifications to control assembly of the polypeptides. DNA sequences encoding the long and short polypeptides were optimized for expression in mammalian cells and cloned into the pcDNA3.4 mammalian expression vector. The DNA plasmid constructs were transfected via liposomes into human embryonic kidney (HEK) 293 cells. A total of eight DNA plasmid constructs were used to assemble four Fc constructs each having three Fc domains.

For each Fc construct, the long and short polypeptides, when co-expressed, produce a branched molecule containing three Fc domains, with the C-terminal Fc monomers of the long polypeptides specifically associating with each other to form one C-terminal Fc domain and with the N-terminal Fc monomers of the long polypeptides specifically associating with the short polypeptides to form two N-terminal Fc domains. Fc constructs 1-4 and their design are described in Table 5 and FIGS. 1 and 2. The sequences utilized in each Fc construct are shown Table 6. Table 7 below further summarizes the characteristics of the long and short polypeptides in each of constructs 1-4.

TABLE 5

| Fc construct | Long Polypeptide #s (SEQ ID NO) | Short Polypeptide #s (SEQ ID NO) | FIG. |
|---|---|---|---|
| Fc construct 1 | 102 and 108 (SEQ ID NO: 43) | 114 and 116 (SEQ ID NO: 44) | FIG. 1 |
| Fc construct 2 | 102 and 108 (SEQ ID NO: 45) | 114 and 116 (SEQ ID NO: 46) | FIG. 1 |
| Fc construct 3 | 102 and 108 (SEQ ID NO: 47) | 114 and 116 (SEQ ID NO: 48) | FIG. 1 |
| Fc construct 4 | 202 and 208 (SEQ ID NO: 49) | 214 and 216 (SEQ ID NO: 48) | FIG. 2 |

TABLE 6

| SEQ ID NO | Amino Acid Sequence |
|---|---|
| SEQ ID NO: 43 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGKSGGGSGGGSGGGSGGGSGGGGDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLKSDGSFFLYSDLTVDKSRWQQGNVFSCSVMHEALHNHYTQKSLSLSPGK |
| SEQ ID NO: 44 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK |
| SEQ ID NO: 45 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGKSGGGSGGGSGGGSGGGSGGGGDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLKSDGSFFLYSDLTVDKSRWQQGNVFSCSVMHEALHNHYTQKSLSLSPG |
| SEQ ID NO: 46 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPG |
| SEQ ID NO: 47 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLKSDGSFFLYSDLTVDKSRWQQGNVFSCSVMHEALHNHYTQKSLSLSPG |
| SEQ ID NO: 48 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVDGFYPSDIAVEWESNGQPENNYKTTPPVLDSDGSFFLVSKLTVDKSRWQQGNVFSCSVMHEALHNHYTQKSLSLSPG |
| SEQ ID NO: 49 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDKLTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGGGGGGGGGGGGGGGGGDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLKSDGSFFLYSDLTVDKSRWQQGNVFSCSVMHEALHNHYTQKSLSLSPG |

TABLE 7

| | Fc construct 1 | Fc construct 2 | Fc construct 3 | Fc construct 4 |
|---|---|---|---|---|
| Spacer in Long Polypeptide (102/202 and 108/208) | SGGGSGGGSGGGSGGGSGG (SEQ ID NO: 18) | SGGGSGGGSGGGSGGGSGG (SEQ ID NO: 18) | GGGGGGGGGGGGGGG (SEQ ID NO: 26) | GGGGGGGGGGGGGGGG (SEQ ID NO: 27) |
| C-terminal Lysine in Long Polypeptide (102/202 and 108/208)? | Y | N | N | N |
| C-terminal Lysine in Short Polypeptide (114/214 and 116/216)? | Y | N | N | N |
| Amino acid mutations in 106/206 and 108/208 | S354C* T366W | S354C T366W | S354C E357K T366W | S354C E357K T366W |
| Amino acid mutations in 104/204 and 110/210 | D399K K409D | D399K K409D | D399K K409D | D399K K409D |
| Amino acid mutations in 114/214 and 116/216 | Y349C T366S L368A Y407V | Y349C T366S L368A Y407V | Y349C T366S L368A K370D Y407V | Y349C T366S L368A K370D Y407V |
| FIG. | FIG. 1 | FIG. 1 | FIG. 1 | FIG. 2 |

*Sequence positions are numbered according to the Kabat numbering system (Kabat et al., Sequences of Proteins of Immunological Interest, National Institutes of Health, Bethesda, Md., ed 5, 1991).

Each of the long polypeptides 102 and 108 in Fc constructs 1-3 (FIG. 1) and long polypeptides 202 and 208 in Fc construct 4 (FIG. 2) contains two Fc domain monomers joined in a tandem series by way of a spacer. Table 8 below provides the sequences of the Fc domain monomers in the long polypeptides and the spacers in Fc constructs 1-4.

TABLE 8

| Fc construct 1 polypeptides 102/108 |
|---|

| | |
|---|---|
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 50) |
| spacer | SGGGSGGGSGGGSGGGSGGG (SEQ ID NO: 18) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPGK (SEQ ID NO: 51) |

| Fc construct 2 polypeptides 102/108 |
|---|

| | |
|---|---|
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 50) |
| spacer | SGGGSGGGSGGGSGGGSGGG (SEQ ID NO: 18) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPG (SEQ ID NO: 52) |

TABLE 8-continued

Fc construct 3 polypeptides 102/108

| | |
|---|---|
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDKLTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 53) |
| spacer | GGGGGGGGGGGGGGG (SEQ ID NO: 26) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPG (SEQ ID NO: 52) |

Fc construct 4 polypeptides 202/208

| | |
|---|---|
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDKLTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 53) |
| spacer | GGGGGGGGGGGGGGGGGGG (SEQ ID NO: 27) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPG (SEQ ID NO: 52) |

Example 2. Expression of Fc Constructs

The expressed proteins were purified from the cell culture supernatant by Protein A-based affinity column chromatography, using a Poros MabCapture A (LifeTechnologies) column. Captured Fc constructs were washed with phosphate buffered saline (low-salt wash) and eluted with 100 mM glycine, pH 3. The eluate was quickly neutralized by the addition of 1 M TRIS pH 7.4 and sterile filtered through a 0.2 µm filter.

The proteins were further fractionated by ion exchange chromatography using Poros XS resin (Applied Biosciences). The column was pre-equilibrated with 50 mM MES, pH 6 (buffer A), and the sample was eluted with a step gradient using 50 mM MES, 400 mM sodium chloride, pH 6 (buffer B) as the elution buffer.

After ion-exchange, the target fraction was buffer exchanged into PBS buffer using a 10 kDa cutoff polyether sulfone (PES) membrane cartridge on a tangential flow filtration system. The samples were concentrated to approximately 30 mg/mL and sterile filtered through a 0.2 µm filter.

Example 3. Experimental Assays Used to Characterize Fc Constructs

Peptide and Glycopeptide Liquid Chromatography-MS/MS

The proteins were diluted to 1 µg/µL in 6M guanidine (Sigma). Dithiothreitol (DTT) was added to a concentration of 10 mM, to reduce the disulfide bonds under denaturing conditions at 65° C. for 30 min. After cooling on ice, the samples were incubated with 30 mM iodoacetamide (IAM) for 1 h in the dark to alkylate (carbamidomethylate) the free thiols. The protein was then dialyzed across a 10-kDa membrane into 25 mM ammonium bicarbonate buffer (pH 7.8) to remove IAM, DTT and guanidine. The protein was digested with trypsin in a Barocycler (NEP 2320; Pressure Biosciences, Inc.). The pressure was cycled between 20,000 psi and ambient pressure at 37° C. for a total of 30 cycles in 1 h. LC-MS/MS analysis of the peptides was performed on an Ultimate 3000 (Dionex) Chromatography System and an Q-Exactive (Thermo Fisher Scientific) Mass Spectrometer. Peptides were separated on a BEH PepMap (Waters) Column using 0.1% FA in water and 0.1% FA in acetonitrile as the mobile phases. The singly xylosylated linker peptide was targeted based on the doubly charged ion (z=2) m/z 842.5 with a quadrupole isolation width of ±1.5 Da.

Intact Mass Spectrometry

The protein was diluted to a concentration of 2 µg/µL in the running buffer consisting of 78.98% water, 20% acetonitrile, 1% formic acid (FA), and 0.02% trifluoroacetic acid. Size exclusion chromatography separation was performed on two Zenix-C SEC-300 (Sepax Technologies, Newark, Del.) 2.1×350 mm in tandem for a total length column length of 700 mm. The proteins were eluted from the SEC column using the running buffer described above at a flow rate of 80 µL/min. Mass spectra were acquired on an QSTAR Elite (Applied Biosystems) Q-ToF mass spectrometer operated in positive mode. The neutral masses under the individual size fractions were deconvoluted using Bayesian peak deconvolution by summing the spectra across the entire width of the chromatographic peak.

Capillary Electrophoresis-Sodium Dodecyl Sulfate (CE-SDS) Assay

Samples were diluted to 1 mg/mL and mixed with the HT Protein Express denaturing buffer (PerkinElmer). The mixture was incubated at 40° C. for 20 min. Samples were diluted with 70 µL of water and transferred to a 96-well plate. Samples were analyzed by a Caliper GXII instrument (PerkinElmer) equipped with the HT Protein Express LabChip (PerkinElmer). Fluorescence intensity was used to calculate the relative abundance of each size variant.

Non-Reducing SDS-PAGE

Samples were denatured in Laemmli sample buffer (4% SDS, Bio-Rad) at 95° C. for 10 min. Samples were run on a Criterion TGX stain-free gel (4-15% polyacrylamide, Bio-Rad). Protein bands were visualized by UV illumination or Coommassie blue staining. Gels were imaged by Chemi-Doc MP Imaging System (Bio-Rad). Quantification of bands was performed using Imagelab 4.0.1 software (Bio-Rad).

Complement Dependent Cytotoxicity (CDC)

CDC was evaluated by a colorimetric assay in which Raji cells (ATCC) were coated with serially diluted Rituximab, Fc construct 4, or IVIg. Human serum complement (Quidel) was added to all wells at 25% v/v and incubated for 2 h at 37° C. Cells were incubated for 12 h at 37° C. after addition of WST-1 cell proliferation reagent (Roche Applied Science). Plates were placed on a shaker for 2 min and absorbance at 450 nm was measured.

Example 4. O-Glycosylation and Proteolysis of Linker Serine Residues

O-Glycosylation at Linker Serine Residues

As described in Example 1, we designed the Fc constructs to increase folding efficiencies, to minimize uncontrolled association of subunits, and to generate compositions for pharmaceutical use that are substantially homogenous. In an effort to achieve these goals, we investigated different linkers between the two Fc domain monomers in the long polypeptide (102 and 108 in FIG. 1; 202 and 208 in FIG. 2). Fc construct 1 and Fc construct 2 each has a serine-glycine linker (SGGGSGGGSGGGSGGGSGGG (SEQ ID NO: 18)) between the two Fc domain monomers in the long polypeptide.

Figure 3:
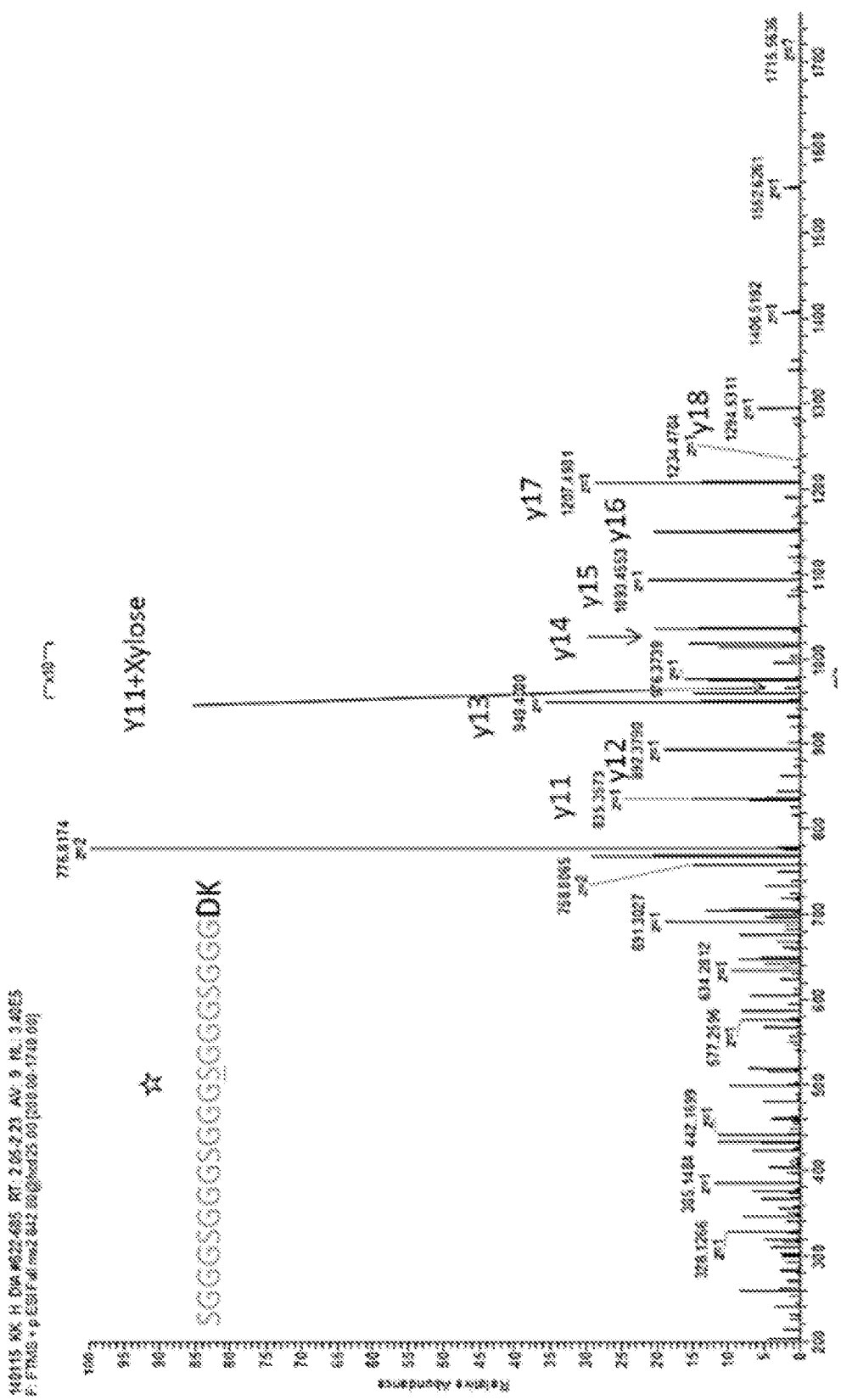
FIG. 3 shows identification of O-xylosylated Ser in the Fc construct 2 linker (SGGGSGGGSGGGSGGGSGGG (SEQ ID NO: 18)) by LC-MS/MS.

When Fc construct 2, which contains the linker SGGGSGGGSGGGSGGGSGGG (SEQ ID NO: 18) between the two Fc domain monomers in the long polypeptide, was analyzed by peptide LC-MS/MS, O-xylosylation was observed (FIG. 3). However, as fragments y2 to y9 do not contain xylose, the fifth serine in the linker is not O-xylosylated. There may be multiple sites that are O-xylosylated, but each peptide is only singly O-xylosylated. The extent and location of this post-translational modification may depend on both sequence and expression system.

Figure 4:
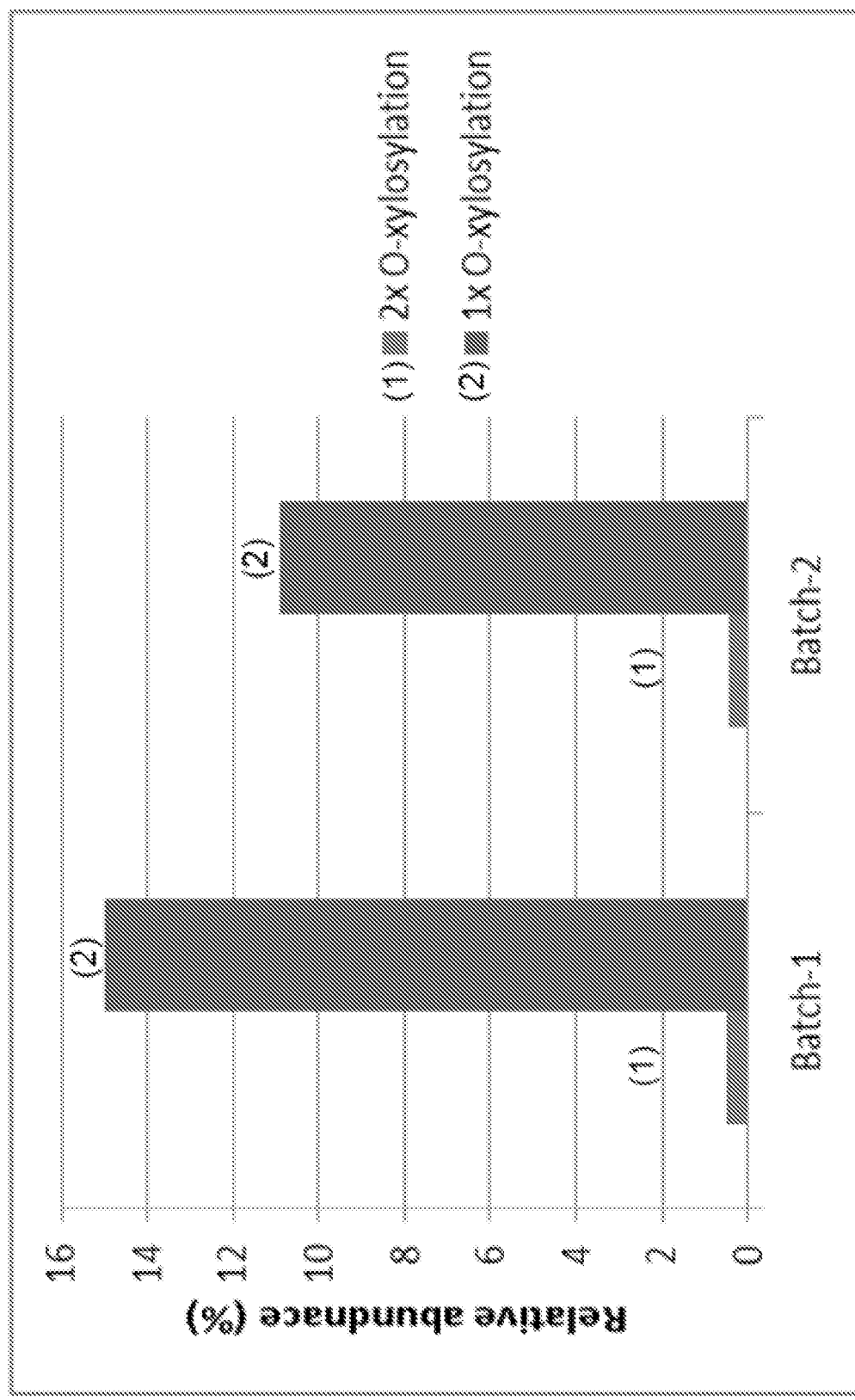
FIG. 4 shows the abundance of linker O-xylosylation in an Fc construct having two Fc domains (the Fc construct shown in FIG. 13) as determined by LC-MS/MS.

Likewise, O-xylosylation was observed in an Fc construct having two Fc domains (the Fc construct shown in FIG. 13) containing the same $(SG_3)_5$ linker (FIG. 4). Modification was observed at multiple sites, with up to two xylose modifications in each linker. Moreover, the level of modification was variable between batches.

After observing O-xylosylation at serine residues in the serine-glycine linker, we investigated alternative linkers that contained only glycine residues in order to further optimize linker sequence and improve the homogeneity of the Fc construct. As a result, an all-glycine spacer was selected for use in Fc construct 3 and Fc construct 4. Fc construct 3 has a 15-mer all-glycine spacer (GGGGGGGGGGGGGGG (SEQ ID NO: 26)) between the two Fc domain monomers in the long polypeptide. Fc construct 4 has a 20-mer all-glycine spacer (GGGGGGGGGGGGGGGGGGGG (SEQ ID NO: 27)) between the two Fc domain monomers in the long polypeptide.

Proteolysis at Linker Serine Residues

Figure 5:
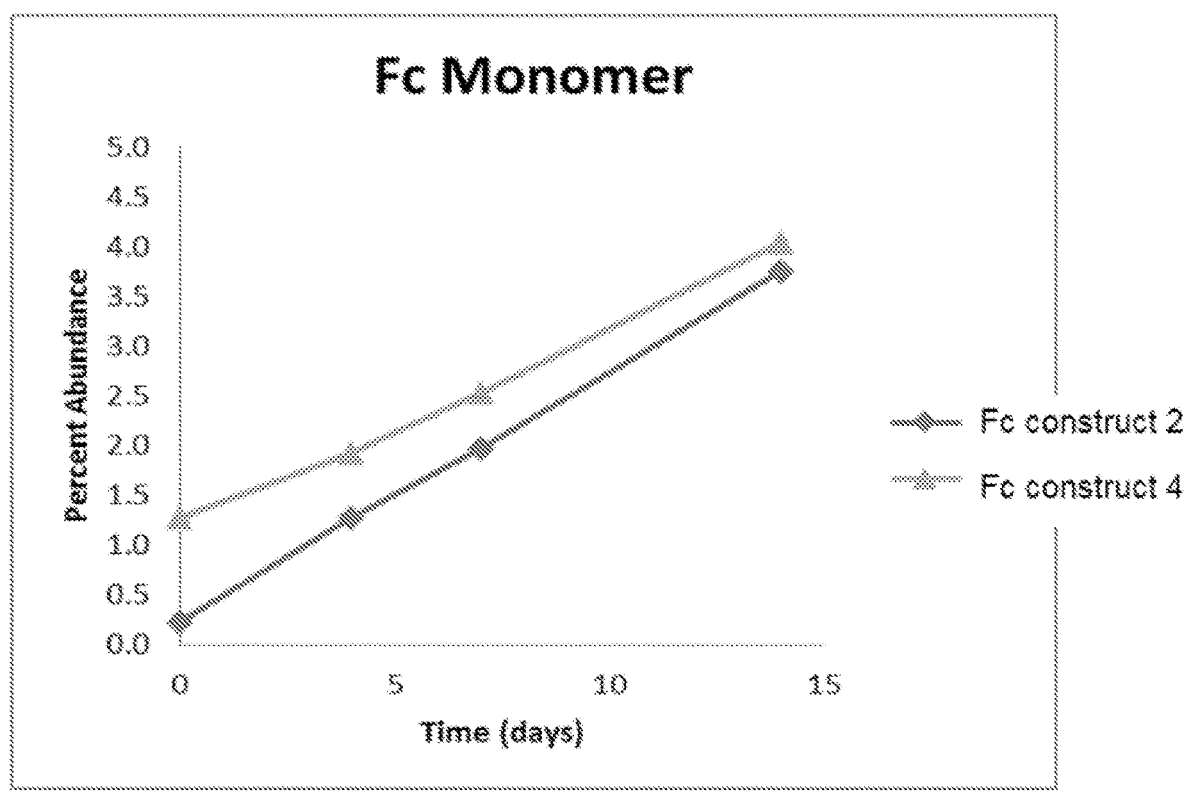
FIG. 5 shows the formation of monomeric Fc species from Fc constructs 2 and 4 upon storage at 45° C. as determined by CE-SDS.

In some embodiments, Fc constructs were found to undergo proteolysis in the linkers upon incubation at 45° C. in phosphate buffered saline, generating monomeric Fc products. The rate of monomer formation in Fc construct 2 (which contains the linker SGGGSGGGSGGGSGGGSGGG in each of the polypeptides 102 and 108) was faster than in Fc construct 4 (which contains the all-glycine spacer GGGGGGGGGGGGGGGGGGGG in each of the polypeptides 202 and 208) (FIG. 5), indicating that the all-glycine spacer is less susceptible to proteolysis. This effect was found to be general amongst branched Fc constructs having three Fc domains for multiple linker lengths; all-glycine spacers were proteolyzed more slowly than serine-glycine linkers (Table 9).

TABLE 9

| Linker Sequence | Rate of monomer formation (% monomer/day) |
| --- | --- |
| $G_8$ | 0.17 |
| $G_{15}$ | 0.21 |
| $G_{20}$ | 0.24 |
| $(SG_4)_4$ | 0.33 |
| $(SG_3)_5$ | 0.34 |

Figure 6:
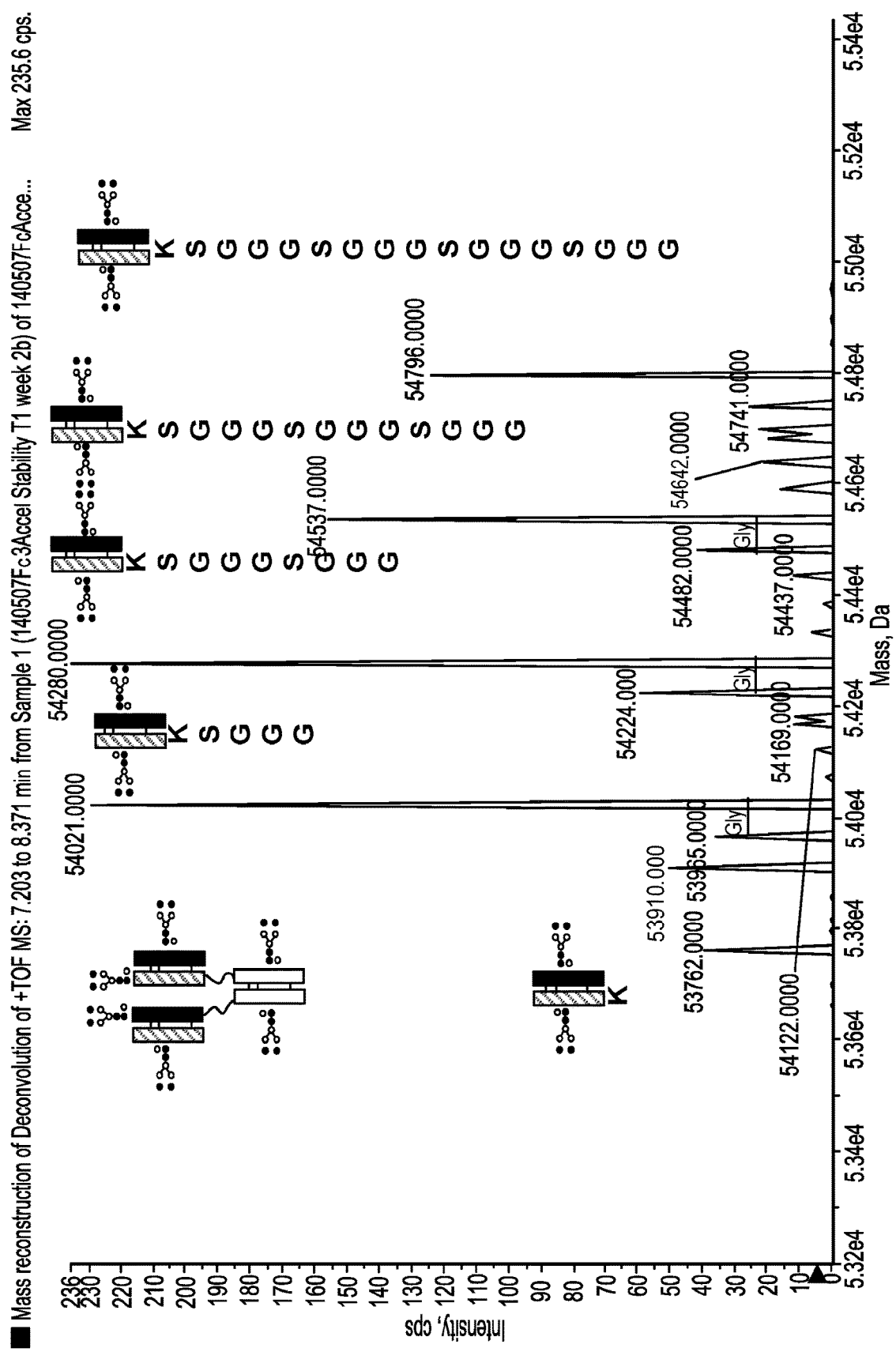
FIG. 6 shows proteolysis products of Fc construct 2 upon two weeks of storage at 45° C. as determined by LC-MS.
Figure 7:
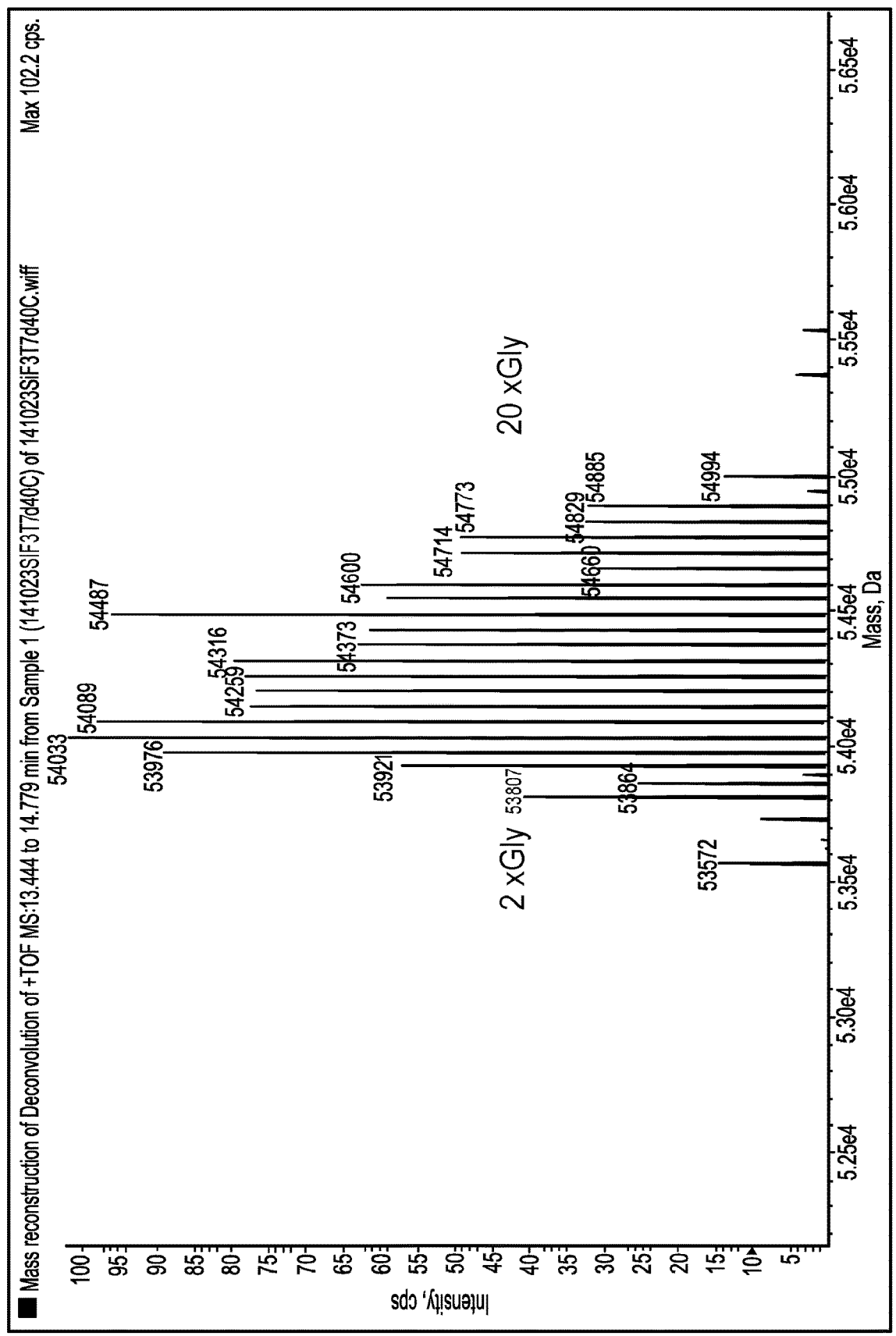
FIG. 7 shows proteolysis products of Fc construct 4 upon two weeks of storage at 45° C. as determined by LC-MS.

Furthermore, analyses by mass spectrometry of the monomeric Fc products in Fc construct 2, with an $(SG_3)_5$ linker in each of polypeptides 102 and 108, demonstrated that the dominant products were cleaved to the N-terminal side of serine, with all but the first serines susceptible to proteolysis (FIG. 6). In contrast, the cleavage products of Fc construct 4, with a $G_{20}$ spacer in each of polypeptides 202 and 208, did not show strong specificity for any particular spacer residue (FIG. 7). Together, these results indicated that the all-glycine spacer had a decreased susceptibility to proteolysis. To limit proteolysis, a serine-free spacer may be used, such as the $G_{20}$ spacer used in Fc construct 4. Use of such a glycine spacer substantially improves the homogeneity of the final Fc construct composition.

Example 5. Optimization of the Linker Length

To further optimized homogeneity, linker length was explored by preparing variations on the Fc construct 2 sequence in which the $(SG_3)_5$ linker was replaced with a $G_8$, $G_{15}$, or $G_{20}$ spacer. Analyses by in vitro assays indicated that the linker length impacted biological activity, presumably by altering the ability of the Fc construct to interact with Fcγ receptors.

Figure 8:
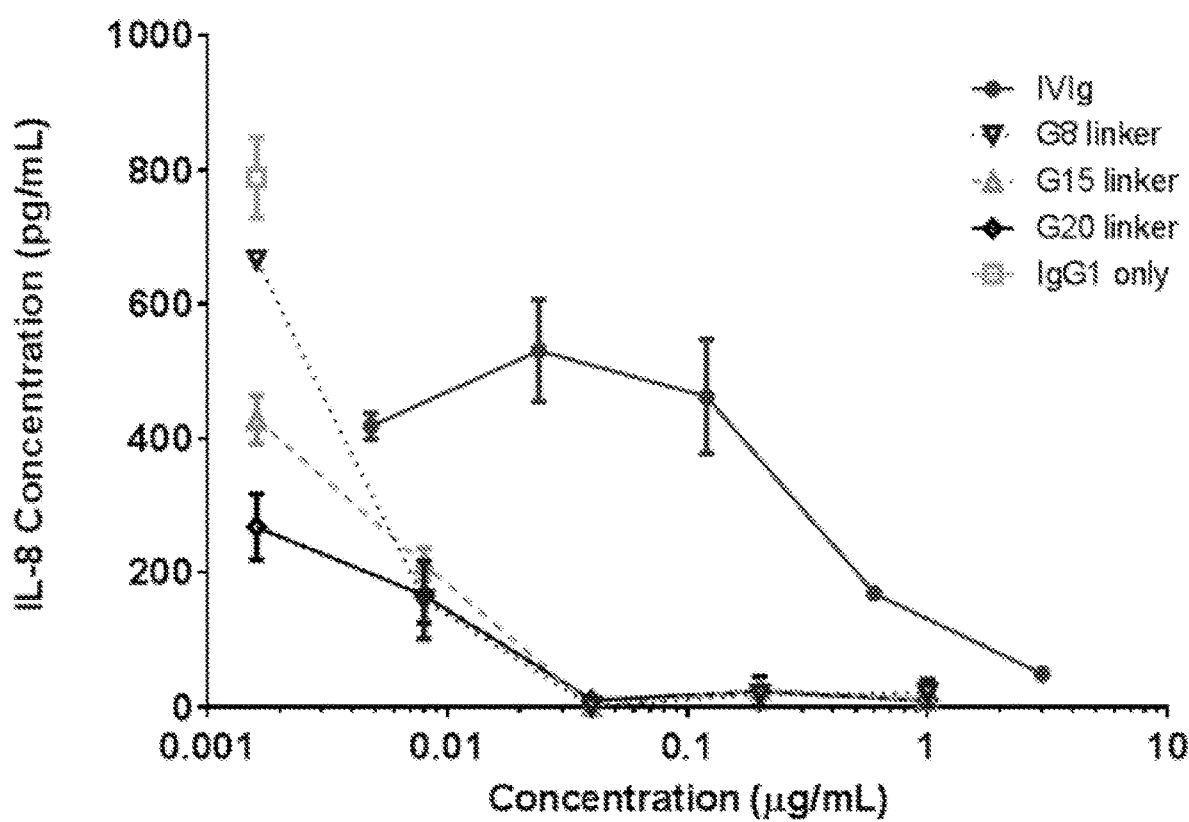
FIG. 8 shows the inhibition of IL-8 release by THP-1 cells by Fc construct 2 with varying linker lengths.

Inhibition of IL-8 release by THP-1 cells stimulated by plate-bound IgG was found to depend on linker length (FIG. 8). Inhibition at low Fc construct concentrations followed the order $G_8<G_{15}<G_{20}$, with Fc construct 2 having a $G_{20}$ spacer most strongly inhibiting IL-8 release by THP-1 cells.

Figure 9:
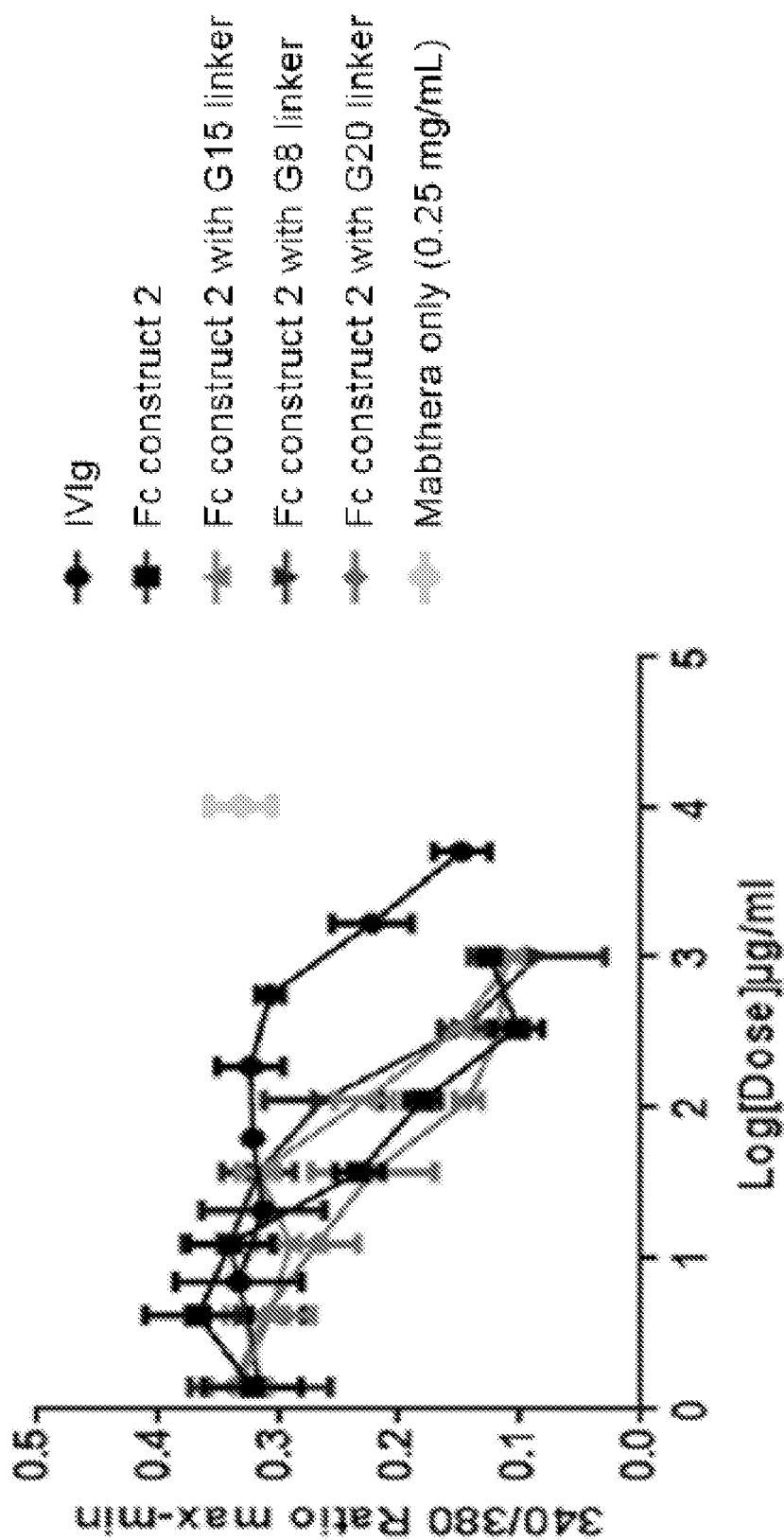
FIG. 9 shows the inhibition of calcium flux in neutrophils by Fc construct 2 with varying linker lengths.

Further, the inhibition of calcium flux in neutrophils was found to be dependent upon linker length (FIG. 9). Inhibition followed the order $G_8<G_{15}<G_{20}$, with Fc construct 2 having the $G_{20}$ spacer exhibiting the greatest inhibition of calcium flux in neutrophils.

Example 6. Optimization of Heterodimerization by Knob-into-Hole Technology

Figure 10:
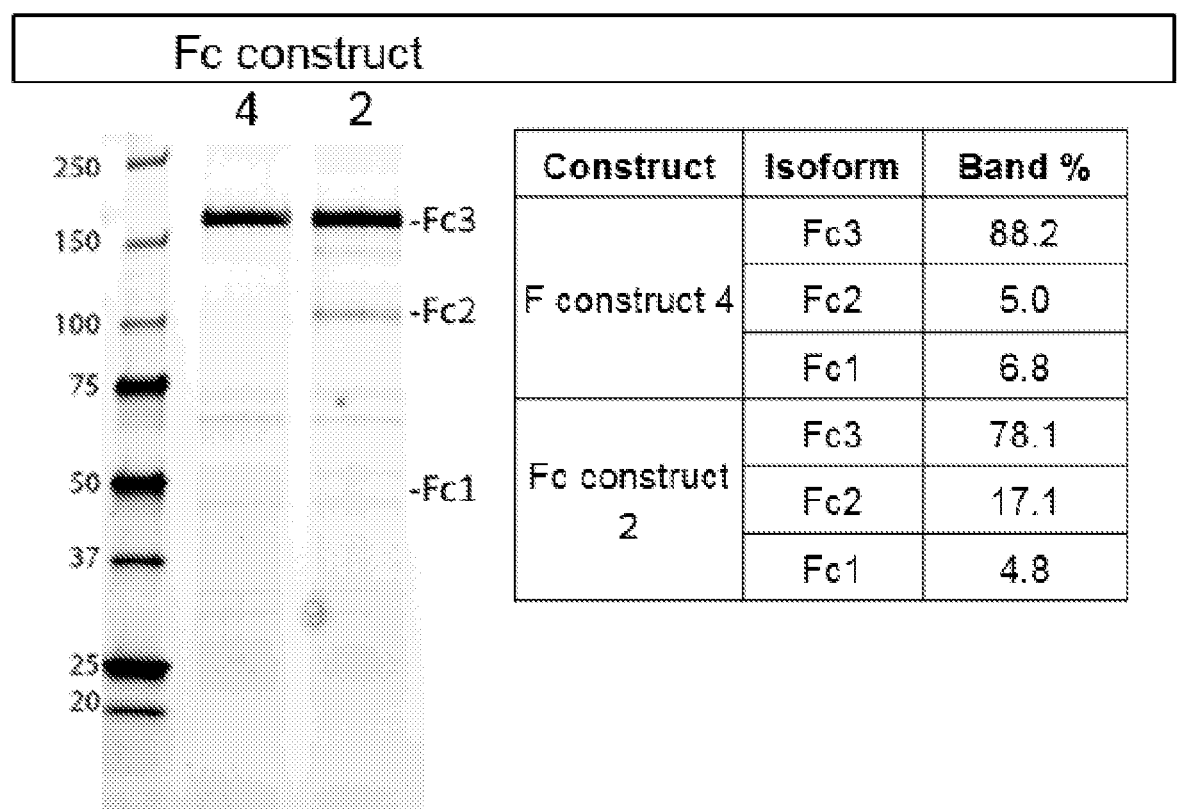
FIG. 10 shows the size distribution by non-reducing SDS-PAGE of Fc construct 2 and Fc construct 4 in unpurified media.

Plasmids expressing the Fc construct 2 long and short polypeptides (polypeptides 102, 108, 114, and 116 in FIG. 1) or Fc construct 4 long and short polypeptides (polypeptides 202, 208, 214, and 216 in FIG. 2) were transfected into HEK293 cells. Following seven days in culture, cells were cleared by centrifugation and raw media supernatants were separated by non-reducing SDS-PAGE (FIG. 10). Densitometric analysis of the visualized protein bands revealed that Fc construct 2 having three Fc domains and Fc construct 4 having three Fc domains (Fc3) are expressed at similar levels. However, the constructs for Fc construct 2 expressed significantly higher levels of contaminating dimer (Fc2) species (FIG. 10). Both sets of constructs expressed similar levels of the monomer species (Fc1). Additional bands present in the image represent media components that are present in mock transfected controls.

These results indicate that having both electrostatic steering mutations that promote heterodimerization and knob-into-hole mutations that promote heterodimerization in the "branch" subunits (e.g., Fc domain monomers 106, 114, 112, and 116 in FIG. 1; Fc domain monomers 206, 214, 212, and 216 in FIG. 2) enhances formation of a heterodimeric Fc domain in an Fc construct, optimizes the assembly of an Fc construct having three Fc domains, and improves the homogeneity of the composition containing the Fc construct.

Example 7. Electrostatic Steering for Control of Homodimerization

To minimize off-register association of subunits, which generates unwanted high molecular weight oligomers and multimers, mutations that favor heterodimerization (e.g., knobs and holes) were introduced into the "branch" subunits (e.g., Fc domain monomers 106, 112, 114, and 116 in FIG. 1; Fc domain monomers 206, 212, 214, and 216 in FIG. 2). These amino acid substitutions preserve the attraction of knobs subunits (e.g., Fc domain monomers 106 and 112 in FIG. 1; Fc domain monomers 206 and 212 in FIG. 2) for the holes counterparts (e.g., Fc domain monomers 114 and 116 in FIG. 1; Fc domain monomers 214 and 216 in FIG. 2) and at the same time hinder association between knobs subunits. Because the knobs mutations also inhibit assembly with wild-type Fc sequences, it calls into question the necessity of including additional mutations to further reduce affinity of the "stem" Fc subunits (e.g., Fc domain monomers 104 and 110 in FIG. 1; Fc domain monomers 204 and 210 in FIG. 2) for the knobs and holes "branch" subunits. To address this question, an Fc construct long polypeptide was generated which contained a wild-type Fc domain monomer sequence in the carboxyl terminal "stem" subunit and an Fc domain monomer carrying knob mutations in the amino terminal "branch" subunit. The corresponding short polypeptide was the Fc domain monomer carrying hole mutations. This Fc construct is based on the sequences of the polypeptides in Fc construct 2, but has a wild-type Fc domain monomer sequence in the carboxyl terminal "stem" subunit in each of the long polypeptides.

Figure 11:
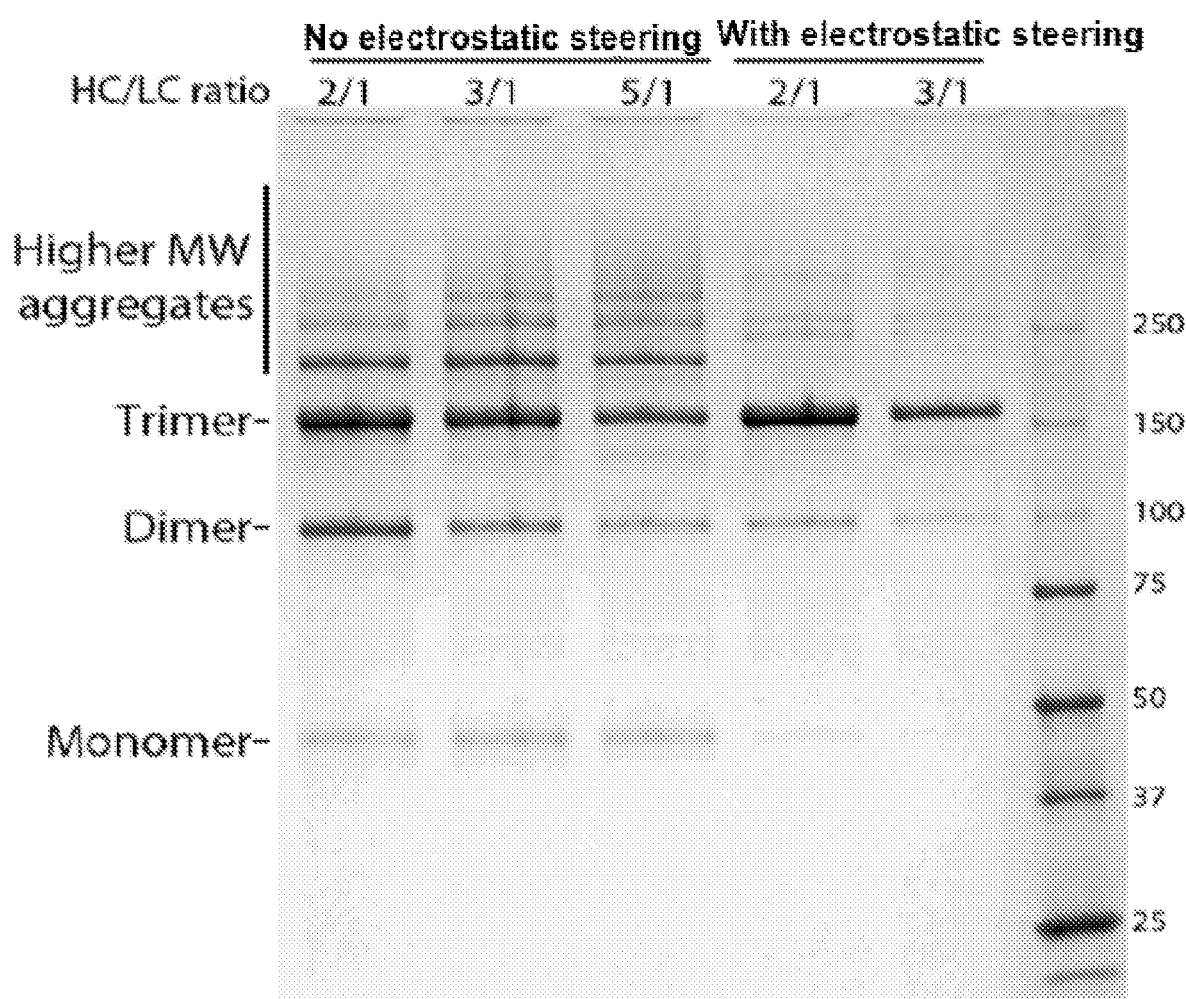
FIG. 11 shows the expression and assembly of Fc construct 2 ("With electrostatic steering") and another Fc construct having three Fc domains but without electrostatic steering mutations in the "stem" subunits ("No electrostatic steering").

HEK293 cells were co-transfected with plasmids expressing Fc construct 2 (which has homodimerizing electrostatic steering mutations in the Fc domain monomer in the carboxyl terminal "stem" subunit in each of the long polypeptides; see Tables 5 and 6 in Example 1), or an Fc construct based on Fc construct 2 in which the Fc domain monomer in the carboxyl terminal "stem" subunit in each of the long polypeptides was replaced with a wild-type Fc domain monomer sequence (SEQ ID NO: 42) (as described above). Following seven days in culture, cells were cleared by centrifugation and raw media supernatants were separated by non-reducing SDS-PAGE. Imaging of stained proteins revealed that the Fc construct without electrostatic steering mutations in the "stem" subunits (labeled "No electrostatic steering" (lanes 1-3) in FIG. 11) contained much higher levels of monomer (Fc1) and dimer (Fc2) than the Fc construct 2 counterpart (labeled "With electrostatic steering" (lanes 4 and 5) in FIG. 11). Furthermore, a much larger number of bands higher in molecular weight than the trimer can be detected (lanes 1-3 in FIG. 11).

These results confirm that having electrostatic steering mutations that promote homodimerization in the "stem" subunits (e.g., Fc domain monomers 104 and 110 in FIG. 1; Fc domain monomers 204 and 210 in FIG. 2) further enhances formation of a homodimeric Fc domain in the Fc construct, optimizes the assembly of an Fc construct having three Fc domains, and improves the homogeneity of the composition containing the Fc construct.

Figure 12:
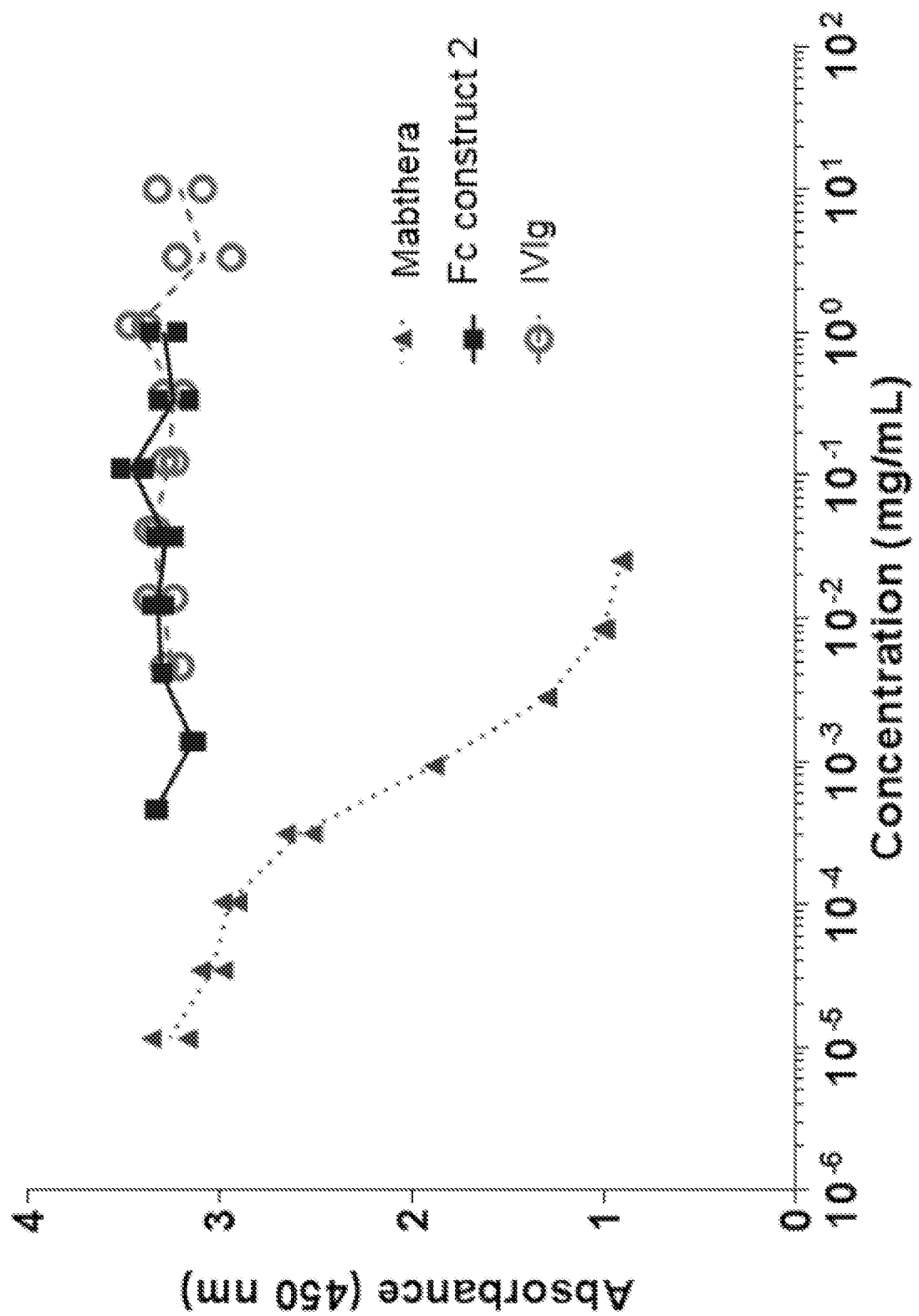
FIG. 12 shows that the removal of the C-terminal lysine to generate Fc construct 2 did not induce complement dependent cytotoxicity (CDC) in vitro.

Example 8. Optimization of Composition Homogeneity by Elimination of C-Terminal Lysine Residues The C-terminal lysine residue of immunoglobulins is highly conserved across many species. In some instances, C-terminal lysines in polypeptides are removed by the cellular machinery during protein production. We aimed to further improve the uniformity of the Fc constructs in the composition and to achieve a more homogenous composition containing an Fc construct described herein by removing the C-terminal lysine from the each of the polypeptides in the Fc construct. Fc construct 2 does not contain any C-terminal lysine residues in either its long polypeptides (102 and 108; see Example 1, Tables 5-7; FIG. 1) or short polypeptides (114 and 116). FIG. 12 shows that the removal of the C-terminal lysine to generate Fc construct 2 did not induce complement dependent cytotoxicity (CDC) in vitro. Thus, by removal of the C-terminal lysine residue, we were able to improve homogeneity of the Fc construct pharmaceutical composition without triggering adverse immunological side effects.

Example 9. Efficacy of Fc Constructs in a Chronic Idiopathic Thrombocytopenic Purpura (ITP) Model Female C57BL/6 mice weighing 18-22 grams were purchased from Charles River Labs and used in the studies after one week of acclimation. Mice were treated i.p. with rat anti-mouse CD41 antibody (anti-CD41; 1.5 µg/mouse) for 4 days. Saline, IVIg, Construct 2, and Construct 4 were given i.v. one to two h after the 3rd antibody injection on Day 3. Platelet levels were measured on Day 5, 24 h after the 4th anti-CD41 antibody injection, in blood taken by submandibular bleeds.

Figure 18:
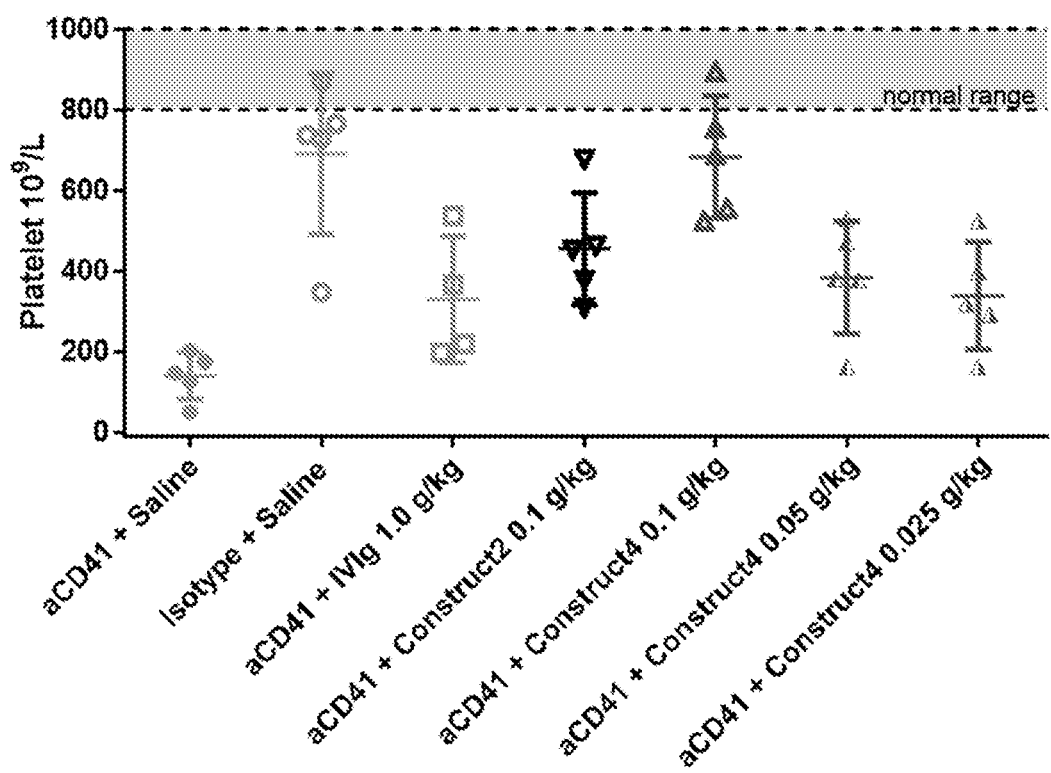
FIG. 18 shows the platelet levels comparing IVIG, Construct 2, and Construct 4 in a chronic ITP model.
Figure 19:
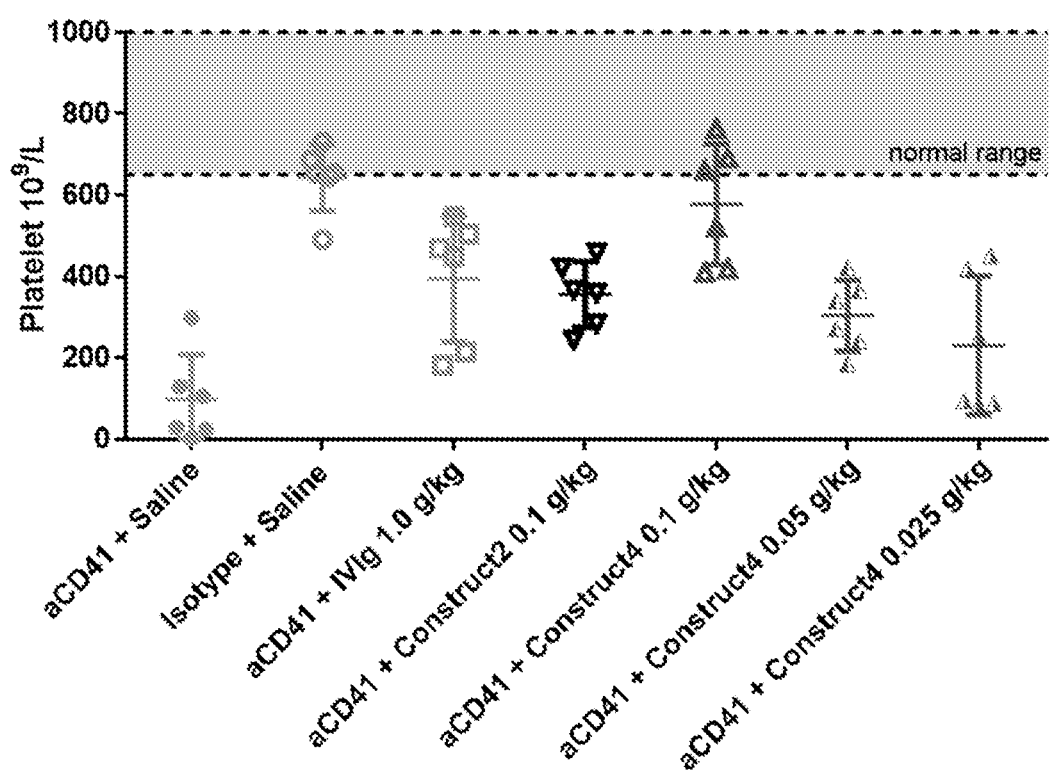
FIG. 19 shows the platelet levels comparing IVIG, Construct 2, and Construct 4 in a chronic ITP model.
Figure 20:
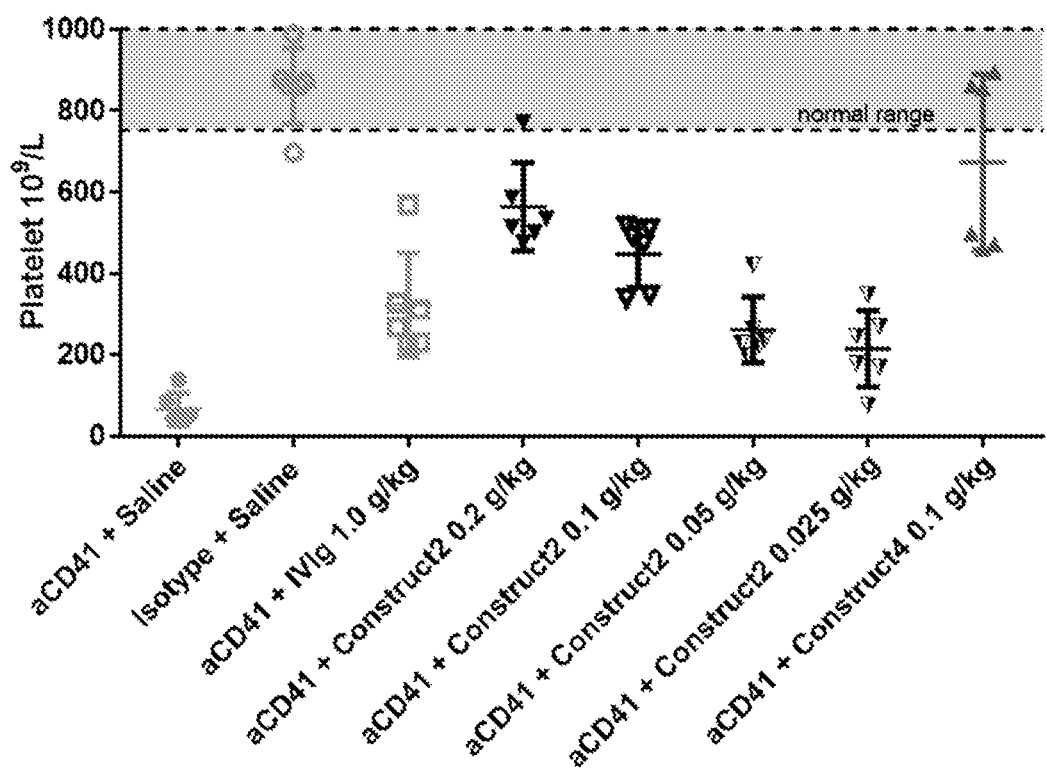
FIG. 20 shows the platelet levels comparing IVIG, Construct 2, and Construct 4 in a chronic IPT model.

Multiple studies comparing Construct 2 and Construct 4 were performed in the ITP model (FIG. 18, FIGS. 19, and 20). In all three studies, Construct 4 showed higher efficacy than Construct 2 dosed at 0.1 g/kg.

Example 10. Pharmacokinetic Behavior of Construct 4 in Comparison to Fc Multimer Constructs Fc multimers were generated as described in (Strome et al, US 2010/0239633 A1; Jain et al, Arthritis Res. Ther. 14, R192 (2012)). Specifically, the wild type IgG1 Fc was fused at the C-terminus to an IgG2 hinge sequence (construct X1). The DNA plasmid construct was transfected via liposomes into HEK293 cells. Following seven days in culture, cells were cleared by centrifugation.

The expressed proteins were purified from the cell culture supernatant by Protein A-based affinity column chromatography, using a Poros MabCapture A column. Captured constructs were washed with phosphate buffered saline (low-salt wash) and eluted with 100 mM glycine, pH 3. The eluate was quickly neutralized by the addition of 1 M TRIS pH 7.4 and sterile filtered through a 0.2 μm filter.

The proteins were further fractionated by ion exchange chromatography using Poros XS resin. The column was pre-equilibrated with 50 mM MES, pH 6 (buffer A), and the sample was diluted in the equilibration buffer before loading. The sample was eluted using a multi-step gradient with 50 mM MES, 400 mM sodium chloride, pH 6 (buffer B) as the elution buffer. The gradient steps included 0-40% B for 2 column volumes (CV) to remove low molecular weight species, a step hold at 40% B (4 CV), followed by 40-80% B (4 CV) to isolate the target species and then increased linearly to 100% B. All protein-containing fractions were screened by analytical size exclusion chromatography and components quantified by absorbance at 280 nm. Fractions with no more than 8% total content of Fc (approximately 50 kDa) plus Fc dimer (approximately 100 kDa) were combined to produce the purified Fc multimer.

After ion-exchange, the target fraction was buffer exchanged into PBS buffer using a 30 kDa cutoff polyether sulfone (PES) membrane cartridge on a tangential flow filtration system. The samples were concentrated to approximately 30 mg/mL and sterile filtered through a 0.2 μm filter.

Figure 21:
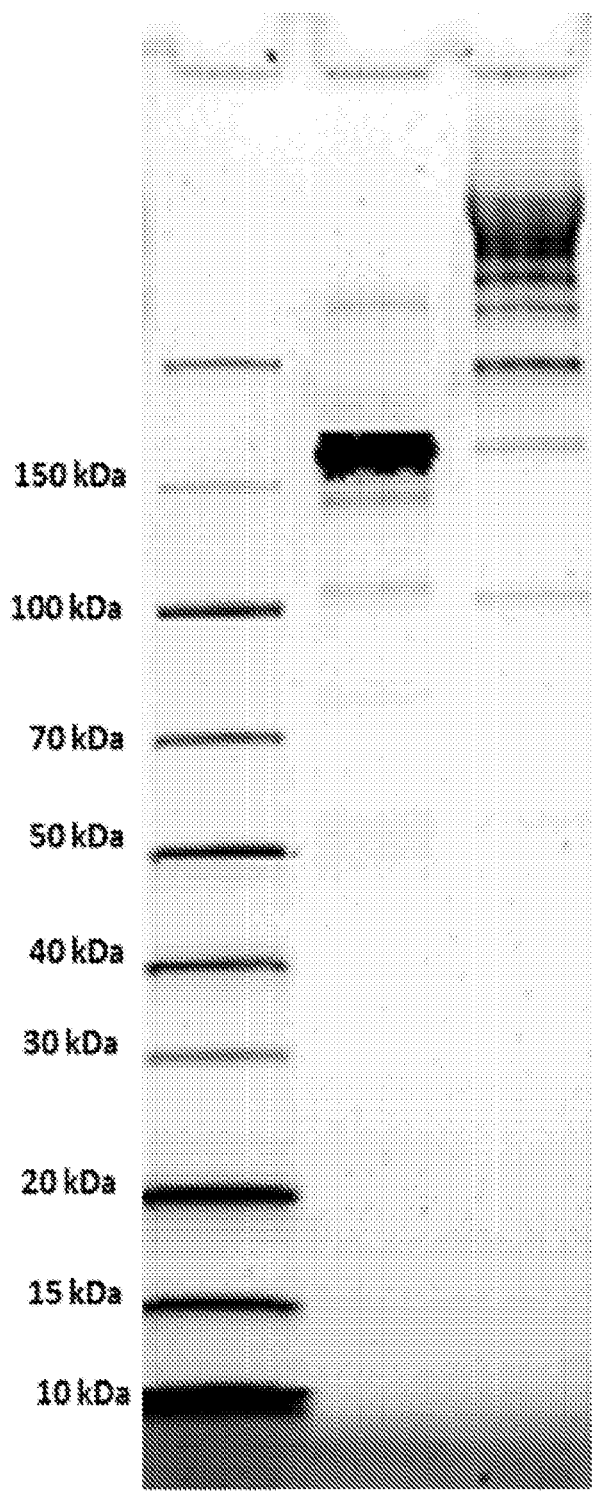
FIG. 21 shows the size distribution by non-reducing SDS-PAGE of purified Fc Construct 4 (middle) and purified Construct X1 (right). Molecular weight standard shown on left.

The molecular weight distributions of Construct 4 and Construct X1 were compared by sodium dodecyl sulfate-polyacrylamide gel electrophoresis (FIG. 21). Construct 4 is principally comprised of an ~150 kDa species (three Fc domains). In contrast, Construct X1 is comprised of multiple species ranging from ~100 kDa (two Fc domains) with numerous bands above 250 kDa and with no single component in the majority.

Female C57BL/6 mice (n=15, 8 weeks old), were dosed intravenously (i.v.) with 0.1 g/kg each of construct X1 or construct 4. Blood (25 μL) was collected from the submandibular vein and was processed for serum. Five mice per group were bled at alternating time points through day 5, while for all remaining time points all fifteen mice were bled in each group. Time points collected included 15 and 30 min; 1, 2, 4, 6, 8, and 24 h; 2, 3, 4, 5, 7, 9, 11, 14, 16, 18, 21, and 24 days. Fc multimer serum concentrations were determined by an anti-human IgG ELISA with an Fc specific detection antibody.

Figure 22:
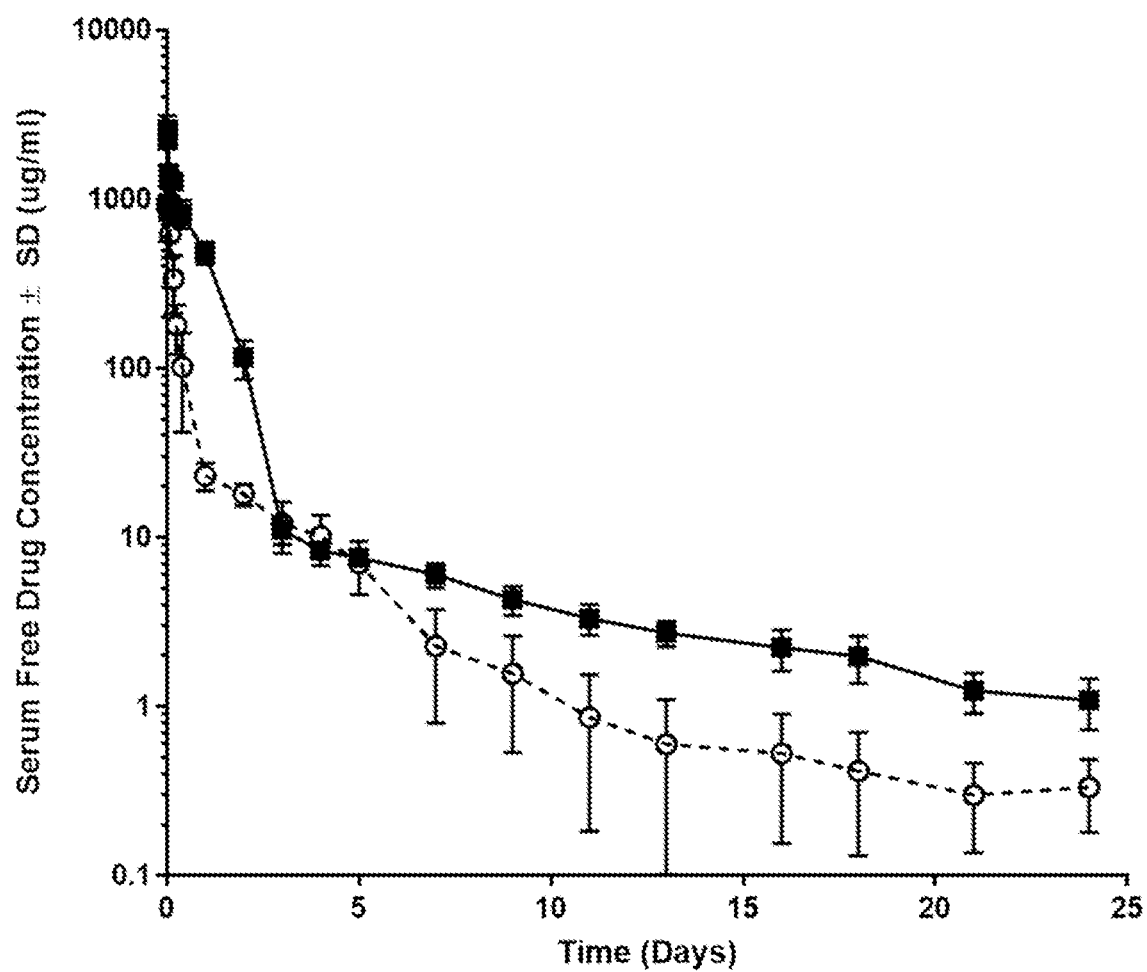
FIG. 22 shows the pharmacokinetic behavior over 24 hours for Construct 4 (black squares with solid line) and construct X1 (open circles with dashed lines).
Figure 23:
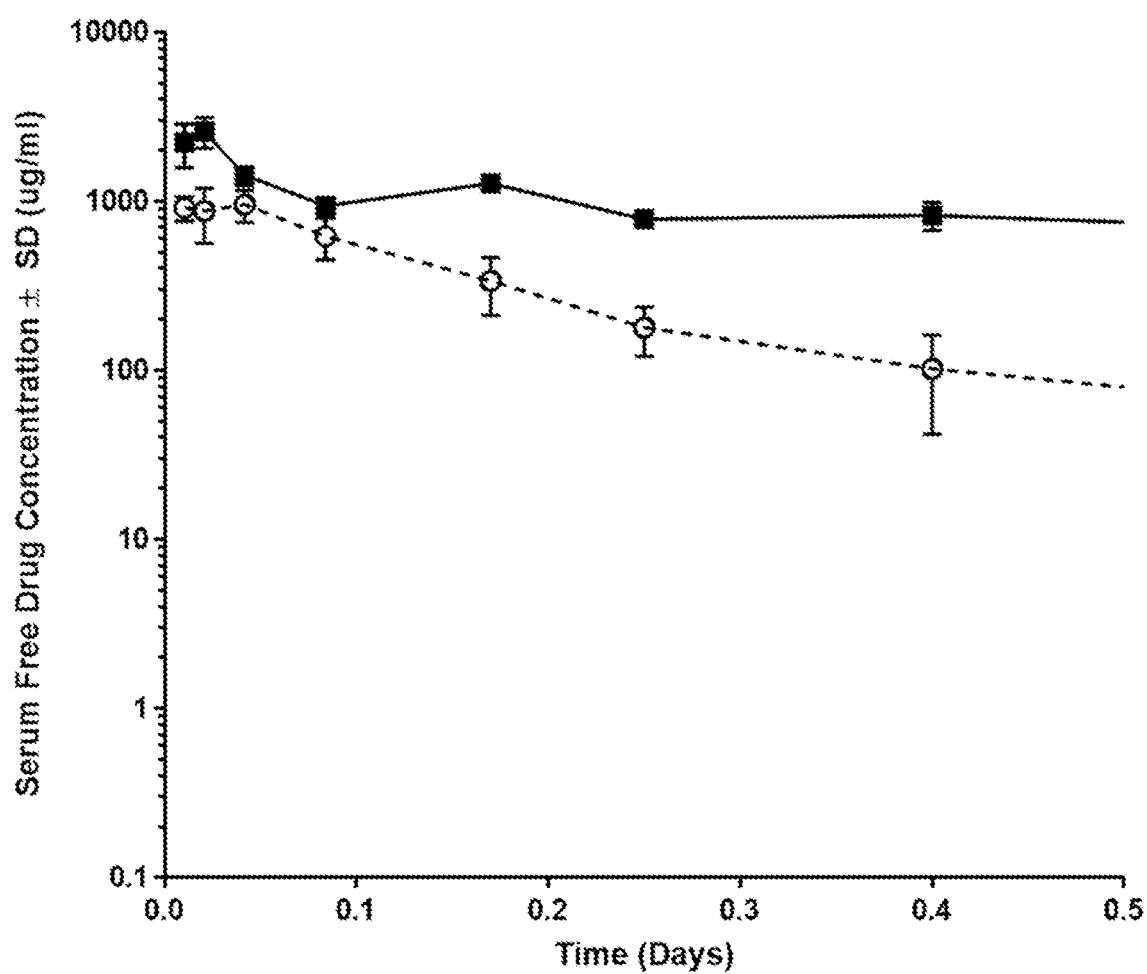
FIG. 23 shows the pharmacokinetic behavior over 12 hours for Construct 4 (black square with solid line) and construct X1 (open circles with dashed lines).

As demonstrated in FIG. 22, the serum levels of construct X1 are lower than those of construct 4 at most time points, although the curves cross briefly between days 3 and 5. In FIG. 22, Construct 4 is shown with black squares and solid line, and construct X1 is show with open circles, dashed lines. An expansion of the early time points is shown in FIG. 23 with Construct 4 (black square with solid line) and construct X1 (open circles with dashed lines).

Example 11. Efficacy of Fc Construct in a Collagen Antibody-induced Arthritis (CAIA) Model Male C57BL/6 mice were injected i.p. with an arthritogenic monoclonal antibody cocktail of four antibodies to collagen II (ArthritoMab, MDBiosciences; 8 mg). On Day 4, animals were injected i.p. with lipopolysaccharide (100 μg). Animals were dosed i.v. with vehicle or test compound on a single day ranging from Day 1 to Day −14 (days were numbered omitting zero). Clinical scoring parameters were as follows: 0=normal, no swelling, redness, or distortion; complete joint flexibility. 1=mild arthritis: mild swelling and/or distortion; complete joint flexibility. 2=moderate arthritis: moderate swelling and/or distortion; reduced joint flexibility or grip strength. 3=severe arthritis: severe swelling and/or distortion; severely reduced joint flexibility or grip strength. 4=ankylosed joints; no joint flexibility and severely impaired movement; moribund. Animals were sacrificed after 12 days.

Figure 24:
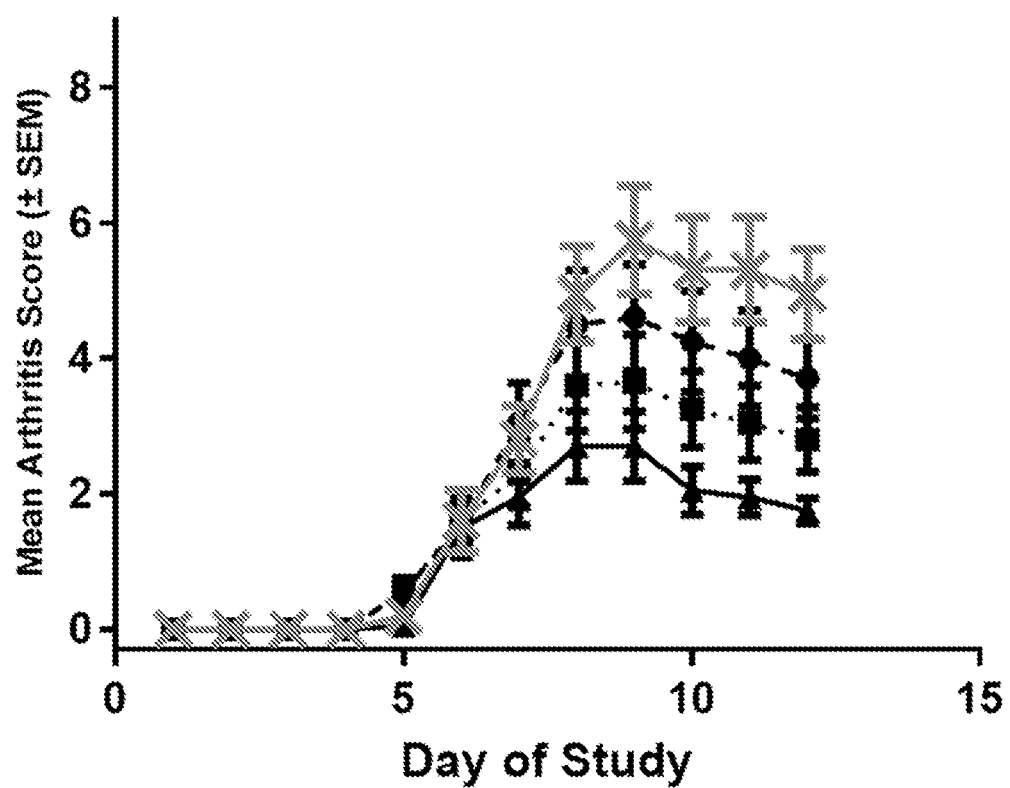
FIG. 24 shows construct 4 dosed therapeutically in a collagen antibody-induced arthritis (CAIA) model on day 6 at 50 mg/kg (black triangles, solid black line), 25 mg/kg (black squares, dotted black line), or 12.5 mg/kg (black circles, dashed black line). An equivalent volume of saline (gray exes, solid gray line) was dosed on day 6 as the vehicle control. Mean and standard error of the mean are shown for each time point.

FIG. 24 is a graph comparing the efficacy of construct 4 dosed therapeutically in a collagen antibody-induced arthritis (CAIA) model on day 6 at 50 mg/kg (black triangles, solid black line), 25 mg/kg (black squares, dotted black line), or 12.5 mg/kg (black circles, dashed black line). An equivalent volume of saline (gray exes, solid gray line) was dosed on day 6 as the vehicle control. Mean and standard error of the mean are shown for each time point.

Figure 25:
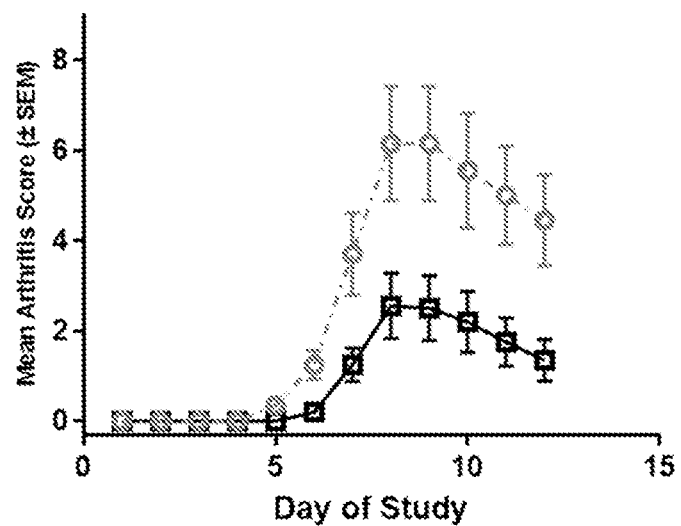
FIG. 25 comparing the efficacy of construct 4 (AA: black squares, solid line) or saline (gray circles, dash-dot line) dosed prophylactically at 100 mg/kg on day 1 in a collagen antibody-induced arthritis (CAIA) model. An equivalent volume of saline (gray circles, dash-dot line) was dosed on day 1. Mean and standard error of the mean are shown for each time point.

Prophylactic dosing in the CAIA model was performed with 100 mg/kg of construct 4 on Day 1 (FIG. 25). The vehicle control (saline) was dosed only on Day 1.

FIG. 25 is a graph comparing the efficacy of construct 4 (AA: black squares, solid line) or saline (gray circles, dash-dot line) dosed prophylactically at 100 mg/kg on day 1 in a collagen antibody-induced arthritis (CAIA) model. An equivalent volume of saline (gray circles, dash-dot line) was dosed on day 1. Mean and standard error of the mean are shown for each time point.

Construct 4 was found to reduce the disease severity compared to the vehicle control when dosed therapeutically (FIG. 24) or prophylactically (FIG. 25).

Example 12. Enhancement of Fc Construct Binding to FcγRIIb

Figure 26:
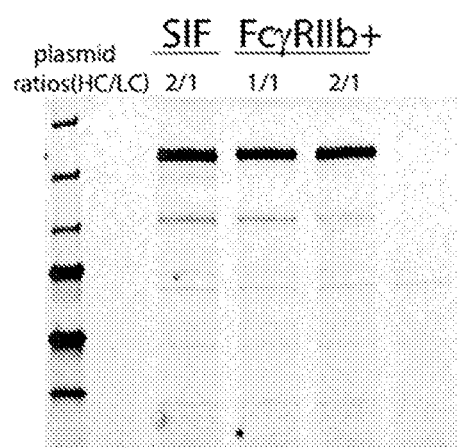
FIG. 26 shows the size distribution by non-reducing SDS-PAGE of clarified media obtained from expression of Construct 4 (SIF) and Construct 4-FcγRIIb+ mutant.

S267E/L328F mutations have been previously shown to significantly and specifically enhance IgG1 binding to the FcγRIIb receptor (Chu et al. Molecular Immunology 45 2008). The S267E/L328F mutations were incorporated into the Construct 4 (SIF) backbone. This Construct 4-FcγRIIb+ mutant expresses and assembles well (see FIG. 26)(SIF: construct 4; FcγRIIb+: Construct 4-FcγRIIb+ mutant). FIG. 26 is an image of the non-reduced sodium dodecyl sulfate polyacrylamide gel electrophoreses results for the clarified media obtained from transient expression of Construct 4 (SIF) and Construct 4-FcγRIIb+ mutant. The plasmids encoding the long and short chains of the Construct 4-FcγRIIb were tranfected into HEK293 cells at 1/1 (w/w) or 2/1 ratios.

Binding of the Construct 4-FcγRIIb+ mutant to the inhibitory FcγRIIb receptor was greatly enhanced when compared to the Construct 4 (SIF3) control (over 300 fold increase in binding). Conversely, binding to the activating FcγRIIa is relatively unaffected, whereas binding to FcγRIIIa is reduced (see FIG. 27).

Figure 27:
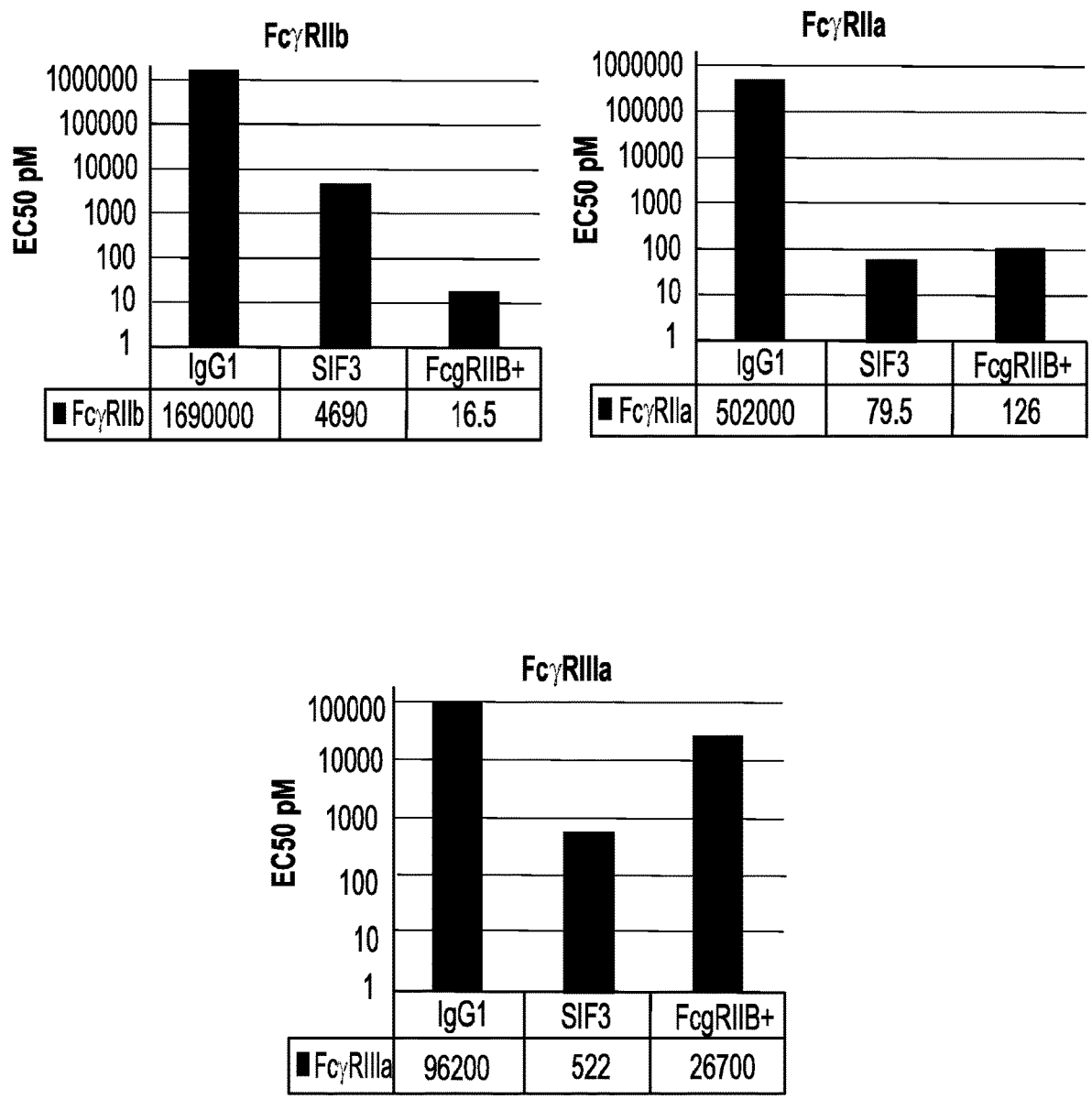
FIG. 27 shows relative binding to Fc gamma receptors of an IgG1 control, Construct 4 (SIF3), and the Construct 4-FcγRIIb+ mutant (FcfRIIB+).

FIG. 27 are graphs that summarize results of experiments which compare binding to Fc gamma receptors of an IgG1 control, Construct 4 and the Construct 4-FcγRIIb+ mutant. Relative binding was measured using cell based, competitive Time Resolved Fluorescence Resonance Energy Transfer assays (CisBio Bioassays, Bedford, Mass.). Results are expressed as EC50 values, indicating the concentration of proband needed to displace a fluorescently labeled antibody bound to the specific cell surface Fc gamma receptor. The higher the number the lower the binding or affinity.

Example 13. Inhibition of Monocyte Derived Dendritic Cells (moDCs) Activation

Figure 28:
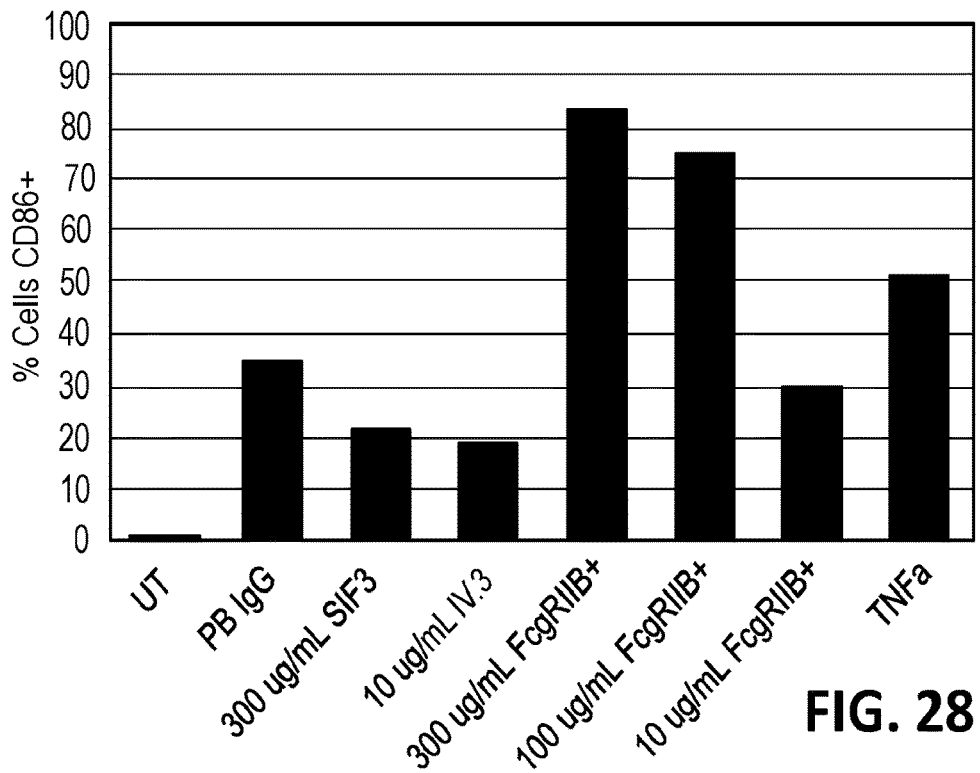
FIG. 28 shows CD86 surface expression on monocyte derived dendritic cells (moDCs).

Construct 4-FcγRIIb+ mutant greatly potentiates activation of monocyte derived dendritic cells (moDCs). Dendritic cells (DCs), which are the most important population of professional antigen presenting cells, process antigen material and present it on the cell surface with the aim of initiating T-cell responses. FcγRs can play a major role in regulating moDC function. Immune complex engagement of activating FcγRs can trigger maturation and activation of immature human moDCs. Conversely, engagement of inhibitory FcγRIIb can suppress maturation and activation (Boruchov A M et al. J Clin Invest. 2005 115(10)). We had previously shown that Fc constructs can inhibit maturation and activation of moDCs (Ortiz et al Sci Transl Med 2016 and see FIG. 3). On the other hand, Fc constructs (e.g., Construct 4/SIF3) with the FcγRIIb+ mutations can significantly potentiate moDC activation in response to exposure to an immune complex surrogate such as plate bound IgG1 (FIG. 28). Incubation with Construct 4-FcγRIIb+ alone does not induce moDC activation (FIG. 29).

Immature human moDCs were generated from negatively selected CD14+ monocytes in the presence of 100 ng/mL GM-CSF and 50 ng/mL IL-4. Harvested DCs were incubated with either PBS, anti-CD32a antibody IV.3, Construct 4 (SIF3), or Construct 4-FcγRIIb+ at 37° C. for 20 min in medium. After blocking, the cell suspension was transferred to the IgG1 coated plates and an additional GM-CSF and IL-4 supplemented medium was added. After a 48 h incubation, lightly adherent cells were harvested by washing plates twice with ice cold PBS. Harvested cells were stained with anti-HLA-DR FITC and anti-CD86-PE Cy7 Abs. Cells were analyzed with a FACSCanto (BD) and FlowJo Software (TreeStar).

FIG. 28: Construct 4 inhibits moDC activation by plate bound IgG whereas Construct 4-FcγRIIb+ enhances activation. Representative histograms show CD86 surface expression on moDCs that were cultured on untreated plates as negative controls (UT) or were pre-treated for 20 min with an antibody blocking activating FcγRIIa (IV.3), with Construct 4 or with increasing concentrations of Construct 4-FcγRIIB+. Treated cells were then transferred to plates containing immobilized IgG1 (PB IgG). Tumor Necrosis Factor alpha (TNFa) treatment was used as a positive control. Surface expression of CD86 was assessed by flow cytometry. Histograms of CD86 expression were gated using unstimulated cells as a control. Percentage of cells positive for CD86 for the treatment conditions are plotted on the y-axis.

Figure 29:
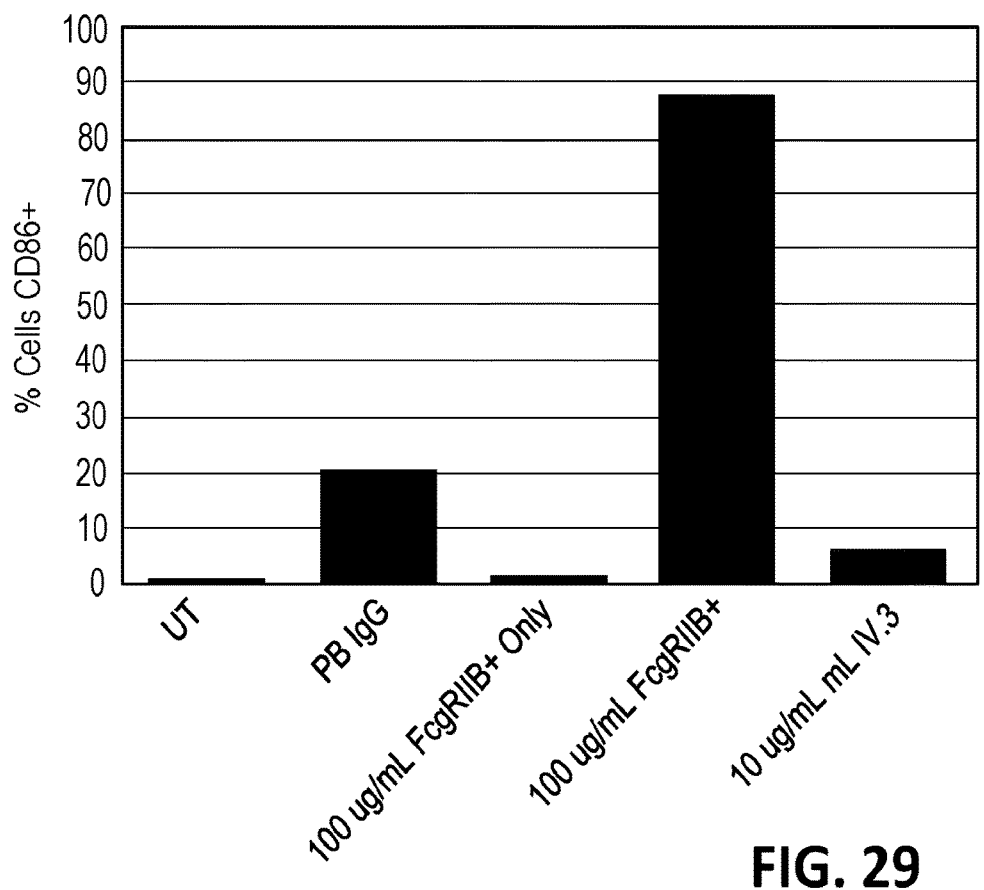
FIG. 29 shows CD86 surface expression on monocyte derived dendritic cells (moDCs).

FIG. 29: Construct 4-FcγRIIb+ does not by itself induce moDC activation but does enhance activation by plate bound IgG. Representative histograms show CD86 surface expression on moDCs that were cultured on untreated plates as negative controls (UT) or pre-treated for 20 min with Construct 4-FcγRIIB+ and then transferred to untreated plates (FcγRIIb+ only). MoDCs pre-treated with PBS (PB IgG), with an antibody that blocks the activating FcγRIIa (IV.3), or with Construct 4-FcγRIIB+(FcgRIIb+) were transferred to plates containing immobilized IgG1. Surface expression of CD86 was assessed by flow cytometry. Histograms of CD86 expression were gated using unstimulated cells as a control. Percentage of cells positive for CD86 for the treatment conditions are plotted on the y-axis.

Other Embodiments

All publications, patents, and patent applications mentioned in this specification are incorporated herein by reference to the same extent as if each independent publication or patent application was specifically and individually indicated to be incorporated by reference.

While the disclosure has been described in connection with specific embodiments thereof, it will be understood that it is capable of further modifications and this application is intended to cover any variations, uses, or adaptations of the disclosure following, in general, the principles of the disclosure and including such departures from the disclosure that come within known or customary practice within the art to which the disclosure pertains and may be applied to the essential features hereinbefore set forth, and follows in the scope of the claims.

Other embodiments are within the claims.

What is claimed is:

1. An Fc construct comprising:
   a). a first polypeptide having the formula A-L-B; wherein
      i). A comprises a first Fc domain monomer;
      ii). L is a linker; and
      iii). B comprises a second Fc domain monomer;
   b). a second polypeptide having the formula A'-L'-B'; wherein
      i). A' comprises a third Fc domain monomer;
      ii). L' is a linker; and
      iii). B' comprises a fourth Fc domain monomer;
   c). a third polypeptide comprises a fifth Fc domain monomer; and
   d). a fourth polypeptide comprises a sixth Fc domain monomer;
   wherein A of first polypeptide and A' of second polypeptide combine to form a first Fc domain, B of first polypeptide and fifth Fc domain monomer combine to form a second Fc domain, and B' of second polypeptide and sixth Fc domain monomer combine to form a third Fc domain; and
   wherein the first and second polypeptide comprise the sequence of SEQ ID NO: 49, and the third and fourth polypeptide comprise the sequence of SEQ ID NO: 48.

2. A pharmaceutical composition comprising the Fc construct of claim 1.

* * * * *

UNITED STATES PATENT AND TRADEMARK OFFICE
CERTIFICATE OF CORRECTION

| | | |
|---|---|---|
| PATENT NO. | : 11,155,640 B2 | Page 1 of 1 |
| APPLICATION NO. | : 16/303793 | |
| DATED | : October 26, 2021 | |
| INVENTOR(S) | : Carlos J. Bosques et al. | |

It is certified that error appears in the above-identified patent and that said Letters Patent is hereby corrected as shown below:

In the Specification

Column 1, Line 11, delete "and or" and insert -- and --, therefor.

Signed and Sealed this
Second Day of August, 2022

Katherine Kelly Vidal
*Director of the United States Patent and Trademark Office*